United States Patent [19]
Marquez et al.

[11] Patent Number: 5,874,464
[45] Date of Patent: Feb. 23, 1999

[54] CONFORMATIONALLY CONSTRAINED DIACYLGLYCEROL ANALOGUES

[75] Inventors: Victor E. Marquez, Gaithersburg; Jeewoo Lee, Rockville; Rajiv Sharma, Rockville; Shaomeng Wang, Rockville; George W. A. Milne, Bethesda; Marc C. Nicklaus, Elkridge; Peter M. Blumberg, Frederick; Nancy E. Lewin, Rockville, all of Md.

[73] Assignee: The United States of America as represented by the Department of Health and Human Services, Washington, D.C.

[21] Appl. No.: 372,602

[22] Filed: Jan. 13, 1995

[51] Int. Cl.[6] .......................... A61K 31/34; C07D 307/34
[52] U.S. Cl. .......................... 514/473; 514/372; 514/424; 514/439; 514/471; 549/40; 549/321; 549/323; 548/214; 548/550; 548/551
[58] Field of Search .......................... 549/40, 321, 323; 548/214, 550, 551; 514/439, 471, 473, 372, 424

[56] References Cited

PUBLICATIONS

Gescher et al., "Protein Kinase C–A Novel Target for Rational Anti–Cancer Drug Design?" *Anti–Cancer Drug Design*, 4:93–105 (1989).

Lee et al., "Conformationally Constrained Analogues of Diacylglycerol (DAG)—II. Differential Interaction of δ–Lactones and γ–Lactones with Protein Kinase C (PK–C)," *Bioorganic & Medicinal Chemistry*, 1(2):119–123 (1993).

Lee et al., "Conformationally Constrained Analogues of Diacylglycerol (DAG).3. Interaction of α–Alkyl–γ–Lactones With Protein Kinase C (PK–C)," *Bioorganic & Medicinal Chemistry Letters*, 3(6):1101–1106 (1993).

Lee et al., "Conformationally Constrained Analogues of Diacylglycerol (DAG).4. Interaction of α–Alkylidene–γ–Lactones With Protein Kinase C (PK–C)," *Bioorganic & Medicinal Chemistry Letters*, 3(6):1107–1110 (1993).

Lee et al., "Conformationally Constrained Analogues of DAG.7. Interaction Of A Medium–Sized ε–Lactone With Protein Kinase C (PK–C)," *Bioorganic & Medicinal Chemistry Letters*, 4(4):543–548 (1994).

Lee et al., "Conformationally Constrained Analogues of DAG.8. Changes In PK–C Binding Affinity Produced By Isosteric Groups Of The 3–O–Acyl Function In 2–Deoxy–L–Ribonolactones," *Bioorganic & Medicinal Chemistry Letters*, 4(11):1369–1374 (1994).

Lee et al., "Synthesis Of Two Rigid Diacylglycerol Analogues Having A Bis–Butyrolactone Skeleton," *Tetrahedron Letters*, 33(12):1539–1542 (1992).

Lee et al., "Synthesis Of Two Rigid Diacylglycerol Analogues Having A Perhydro Furo[3,4–b]Furan Bis–γ–Butyrolactone Skeleton.2.," *Tetrahedron Letters*, 34(27):4314–4316 (1993).

Lee et al., "Synthesis Of Two Rigid Diacylglycerol Analogues Having A Perhydro Furo[3,2–b]Furan Bis–γ–Butyrolactone Skeleton. 3.," *Tetrahedron Letters*, 34(27):4317–4320 (1993).

Marquez et al., "Conformationally Constrained Analogues of Diacylglycerol. 6. Changes in PK–C Binding Affinity For 3–O–Acyl–2–Deoxy–L–Ribonolactones Bearing Different Acyl Chains," *Bioorganic & Medicinal Chemistry Letters*, 4(2):355–360 (1994).

Marquez et al., "The Design Of Potent PK–C Agonists Based On A Constrained Diacylglycerol Template," Abstract 14, American Chemical Society, Division of Medicinal Chemistry, 208th ACS National Meeting, Washington, Aug. 21–25 (1994).

Sharma et al., "Conformationally Constrained Analogues Of Diacylglycerol.5. 2,5–Dideoxy–3–O–Tetradecanoyl–D–Galactono–1,4–Lactone: A Superior Homologue of 3–O–Tetradecanoyl–1–2–Deoxy–L–Ribonolactone With PK–C Binding Affinity," *Bioorangic & Medicinal Chemistry Letters*, 3(10):1993–1998 (1993).

Sharma et al., "4–Bis(Hydroxymethyl)–4–Butanolide: A promising Template For The Construction Of Conformationally Constrained Diacylglycerols," Abstract 67, American Chemical Society, Division of Medicinal Chemistry, 207th ACS National Meeting, San Diego, CA, Mar. 13–17 (1994).

Lee et al., "Synthesis Of Two Rigid Diacylglycerol Analogues Having A 1,7–Dioxaspiro[4,4]Nonane Bis–γ–Butyrolactone Skeleton.4.," *Synlett*, (3):206–208, Mar. (1994).

Teng et al., "Conformationally Constrained Analogues Of Diacylglycerol. Interaction Of γ–Lactones With The Phorbol Ester Receptor Of Protein Kinase C," *J. Am. Chem. Soc.*, 114(3):1059–1070 (1992).

Wang et al., "Protein Kinase C. Modeling Of The Binding Site And Prediction Of Binding Constants," *Journal of Medicinal Chemistry*, 37(9):1326–1338 (1994).

*Primary Examiner*—Amelia Owens
*Attorney, Agent, or Firm*—Leydig, Voit & Mayer, Ltd.

[57] ABSTRACT

Conformationally constrained diacylglycerol analogues, pharmaceutical compositions comprising such analogues, and methods of using such analogues as agonists and antagonists of protein kinase C.

12 Claims, No Drawings

CONFORMATIONALLY CONSTRAINED DIACYLGLYCEROL ANALOGUES

TECHNICAL FIELD OF THE INVENTION

The present invention relates to conformationally constrained diacylglycerol analogues, pharmaceutical compositions comprising such analogues, and methods of using such analogues as protein kinase C agonists and antagonists.

BACKGROUND OF THE INVENTION

Cells respond to certain external stimuli through the production of specific compounds referred to as "second messengers." One family of second messengers is the group of compounds known as diacyl glycerols (DAGs). DAGs are released from cell membrane phospholipids in response to the binding of agonists, such as hormones and growth factors, to cell-surface receptors, which triggers the hydrolysis of phosphatidyl inositol, phosphatidyl choline or phosphatidyl ethanolamine. DAG binds to the regulatory domain of the inactive cytoplasmic enzyme protein kinase C (PK-C), simultaneously increasing its affinity for calcium while causing it to translocate to the cell membrane, where, in the presence of membrane phospholipids, such as phosphatidyl serine, it becomes fully activated. PK-C then catalyzes phosphorylation of serine and threonine residues of enzyme substrates involved in many cellular processes, including growth, cell differentiation, inflammation, nerve function, tumor promotion, and oncogenic expression, by transfer of the γ-phosphate group of ATP.

Given that PK-C represents a central element that transduces signals generated by a broad range of cell signaling pathways that produce DAGs either directly or indirectly and many dominant oncogenes have proven to function, at least in part, through DAG-generating pathways, PK-C has been identified as a potential target enzyme for therapeutic applications, such as anticancer therapy (Gescher et al., Anti-Cancer Drug Design 4: 93–105 (1989)).

Compounds have been developed that bind either to the catalytic site or the DAG binding site of PK-C (see Wang et al., J. Med. Chem. 37(9): 1326–1338 (1994)). UCN-01, staurosporine and Ro-31-8830 are examples of compounds that bind to the catalytic site of PK-C and inhibit PK-C activity. Phorbol-12-myristate-13-acetate and phorbol-12,13-dibutyrate bind to the DAG binding site as activators of PK-C activity. In contrast, bryostatin-1, 12-deoxyphorbol-13-acetate and 12-deoxyphorbol-13-phenylacetate act as partial antagonists of PK-C activity upon binding to the DAG binding site. All of these agents have proven to have therapeutic potential. For example, promising results have been obtained in clinical trials for treatment of melanoma with bryostatin-1. 12-deoxyphorbol-13-acetate has been shown to inhibit mouse skin tumor promotion by 97%. Staurosporine has been shown to be a potent inhibitor of tumor graft proliferation in a mouse model. Ro-31-8830 has been shown to be active orally in a rat model of inflammation and in cultured human T-cells.

Tumor promoters, such as phorbol esters, e.g., 12-O-tetradecanoylphorbol-13-acetate (TPA), and aplysiatoxins, have been shown to activate PK-C by acting as stable, highly potent DAG equivalents. Unlike DAGS, whose presence in the cell membrane is transient, phorbol esters are not metabolized and are, therefore, able to activate PK-C chronically, bypassing the DAG pathway. Chronic constitutive activation of PK-C is associated with resistance of cancerous cells to antitumor drugs.

Compounds that modulate the PK-C pathway by way of the DAG binding site enable selective binding to PK-C, given that the catalytic sites of the thousand or so kinases are structurally homologous and cross-react. The existence of a number of isoforms of PKC and regiospecific expression of PKC mRNAs enable the further selective activation or inhibition of different isoforms of PKC by different agonists or antagonists, respectively.

Unfortunately, ligands currently available for use in targeting the DAG binding site on PK-C, namely the phorbol esters, bryostatins and ingenols, are extremely complex structures with multiple chiral centers, making synthesis and structural modification not only impractical but extremely problematic. Similarly, the indole alkaloids have proven difficult to assess structurally, in terms of homology to the other classes of compounds, so that rational drug design has proven to be elusive. In contrast, DAGs are synthetically accessible but so low in potency as to be unsuitable for use as drugs. However, in view of their structural accessibility, much focus has been placed on DAG analogues in the hopes of obtaining compounds that are not only easily synthesized but sufficiently active to be pharmacologically useful.

In particular, various compounds comprising a conformationally constrained lactone ring system have been synthesized. For example, bis-butyrolactones (Lee et al., Tetrahedron Letters 33(12): 1539–1542 (1992); Lee et al., Tetrahedron Letters 34(27): 4313–4316 (1993); Lee et al., Tetrahedron Letters 34(27): 4317–4320 (1993); Lee et al., SYNLETT 3:206–208 (1994)), γ- and δ-lactones (Teng et al., JACS 114(3): 1059–1070 (1992); Lee et al., Biorg. & Med. Chem. 1(2): 119–123 (1993)), including α-alkyl-γ-lactones (Lee et al., Biorg. & Med. Chem Letters 3(6): 1101–1106 (1993)), α-alkylidene-γ-lactones (Lee et al., Biorg. & Med. Chem. Letters 3(6): 1107–1110 (1993)), D-galactono-1,4-lactones (Sharma et al., Bioorg. & Med. Chem. Letters 3(10): 1993–1998 (1993)), 2-deoxy-L-ribonolactones (Marquez et al., Bioorg. & Med. Chem. Letters 4(2): 355–360 (1994); Lee et al., Bioorg. & Med. Chem. Letters 4(11): 1369–1374 (1994)), and ε-lactones (Lee et al., Bioorg. & Med. Chem. Letters 4(4): 543–548 (1994)) were synthesized to function as DAG analogues but binding of these compounds to PK-C was too low to be pharmacologically useful.

There remains a need, therefore, for DAG analogues with pharmacologically useful activity levels which can be synthesized easily and are not rapidly degraded in vivo. Accordingly, it is an object of the present invention to provide such analogues. It is also an object of the present invention to provide pharmaceutical compositions comprising such analogues and methods of using such analogues as PK-C agonists, including partial agonists, and antagonists, including partial antagonists.

These and other objects and advantages of the present invention, as well as additional inventive features, will be apparent from the description of the invention provided herein.

BRIEF SUMMARY OF THE INVENTION

The present invention provides compounds of:

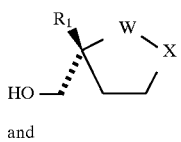

Formula A and

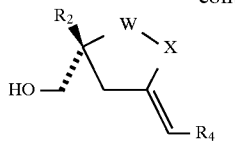

Formula B wherein W is oxygen or nitrogen, X is C(O) or $SO_2$, $R_1$ is $CH=CHSO_2R_3$, $CH=CHSO_2NHR_3$, $CH=CHC(O)OR_3$, $CH=CHC(O)NHR_3$ or $CH=CHC(O)N(OH)R_3$, $R_2$ is $CH=CHSO_2R_3$, $CH=CHSO_2NHR_3$, $CH=CHC(O)OR_3$, $CH=CHC(O)NHR_3$, $CH=CHC(O)N(OH)R_3$, $CH_2CH(OH)C(O)OR_3$, $CH_2CH(OH)SO_2R_3$, $CH_2CH(OH)SO_2NHR_3$ or $CH_2CH(OH)C(O)NHR_3$, and $R_3$ and $R_4$ are the same or different and are selected from the group consisting of a $C_{1-18}$ alkyl, a $C_{2-18}$ alkenyl, a $C_{6-14}$ aryl, a $C_{1-18}$ alkyl-$C_{6-14}$ aryl, and a $C_{6-14}$ aryl-$C_{1-18}$ alkyl. Preferred compounds include those wherein $R_3$ is a $C_{1-4}$ alkyl and $R_4$ is a $C_{2-18}$ alkenyl. Especially preferred compounds include those wherein $R_3$ is methyl. Examples of such preferred compounds are those of Formula B, wherein $R_2$ is $CH=CHC(O)OCH_3$ and $R_4$ is $(CH_2)_7CH=CH(CH_2)_7CH_3$, namely (S)-5-hydroxymethyl-5-[2-(methoxycarbonyl)ethenyl]-3-{(E)-[(Z)-9-octadecenoylidene]}tetrahydro-2-furanone and (S)-5-hydroxymethyl-5-[2-(methoxycarbonyl)ethenyl]-3-{(Z)-[(Z)-9-octadecenoylidene]}tetrahydro-2-furanone. The compounds have pharmacologically useful activity levels, can be synthesized easily, and are not rapidly degraded in vivo.

Also provided are a pharmaceutical composition comprising one or more of the present inventive compounds in a pharmaceutically acceptable carrier and a method of administering a compound of the present invention to a mammal in need thereof.

DETAILED DESCRIPTION OF THE INVENTION

Applicants found that 4-bis(hydroxymethyl)-4-butanolides function as DAG analogues as determined by the ability of these compounds to inhibit the binding of [$^3$H]-phorbol-12,13-dibutyrate ([$^3$H]-PDBU) to PK-C, whether a mixture of isozymes or pure PK-C α. Binding affinities of these compounds are comparable to phorbol-12,13-diacetate, for example. The utility of these compounds is limited, however, because they are racemic, due to the rapid migration of acyl groups from one hydroxyl group to the other under extremely mild conditions. Such racemization is associated with a concomitant reduction in biological potency and makes isolation of the biologically active enantiomer very difficult.

Applicants surprisingly discovered that modification of 4-butanolides by reverse esterification and the introduction of a carbon double bond into the side chain off the lactone ring, e.g., $R_1$ of Formula A and $R_2$ and (=CH)$R_4$ of Formula B infra, enables the isolation of stable single enantiomers with very high affinity towards PK-C. The discovery is surprising for a number of reasons. First, the compounds, which comprise relevant hydrophilic pharmacophoric groups derived from DAG embedded in a lactone ring system and appropriate hydrophobic regions for proper orientation and partitioning in the cell membrane as well as interaction with PK-C, themselves embody the inactive or sn-2,3 configuration of DAG, rather than the active or sn-1,2 configuration. Second, although reverse esterification is occasionally used by organic chemists to reorient groups in a compound to study the effect of such reorientation on activity, it is not done for the purpose of preventing racemization. Accordingly, the use of reverse esterification to prevent the facile racemization of the 4-butanolides was unobvious. Furthermore, in spite of preventing their racemization, the compounds demonstrated a reduced level of PK-C agonistic activity. Third, it was surprising and unexpected that introduction of a carbon double bond into the side chain off the lactone ring of the compounds, e.g., $R_1$ of Formula A and $R_2$ and (=CH)$R_4$ of Formula B infra, not only restored their PK-C agonistic activity but actually increased their affinity for PK-C. Essentially, the carbon double bond served to stabilize the compounds in proper orientation for high affinity interaction with PK-C.

Accordingly, the present invention provides compounds of:

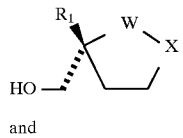

Formula A and

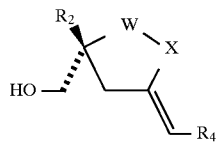

Formula B wherein W is oxygen or nitrogen, X is C(O) or $SO_2$, $R_1$ is $CH=CHSO_2R_3$, $CH=CHSO_2NHR_3$, $CH=CHC(O)OR_3$, $CH=CHC(O)NHR_3$ or $CH=CHC(O)N(OH)R_3$, $R_2$ is $CH=CHSO_2R_3$, $CH=CHSO_2NHR_3$, $CH=CHC(O)OR_3$, $CH=CHC(O)NHR_3$, $CH=CHC(O)N(OH)R_3$, $CH_2CH(OH)C(O)OR_3$, $CH_2CH(OH)SO_2R_3$, $CH_2CH(OH)SO_2NHR_3$ or $CH_2CH(OH)C(O)NHR_3$, and $R_3$ and $R_4$ are the same or different and are selected from the group consisting of a $C_{1-18}$ alkyl, a $C_{2-18}$ alkenyl, a $C_{6-14}$ aryl, a $C_{1-18}$ alkyl-$C_{6-14}$ aryl, and a $C_{6-14}$ aryl-$C_{1-18}$ alkyl. $R_3$ should be chosen so as to maintain proper lipophilic balance of the compound, e.g., as between $R_2$ and $R_4$. Preferred compounds include those wherein $R_3$ is a $C_{1-4}$ alkyl and $R_4$ is a $C_{2-18}$ alkenyl. Especially preferred compounds include those wherein $R_3$ is methyl. Examples of such preferred compounds are those of Formula B, wherein $R_2$ is $CH=CHC(O)OCH_3$ and $R_4$ is $(CH_2)_7CH=CH(CH_2)_7CH_3$, namely (S)-5-hydroxymethyl-5-[2-(methoxycarbonyl)ethenyl]-3-{(E)-[(Z)-9-octadecenoylidene]}tetrahydro-2-furanone and (S)-5-hydroxymethyl-5-[2-(methoxycarbonyl)ethenyl]-3-{(Z)-[(Z)-9-octadecenoylidene]}tetrahydro-2-furanone.

The compounds of the present invention can be synthesized by any one of a number of suitable methods. Preferred methods are set forth in the Examples.

The present invention also provides pharmaceutical compositions comprising one or more of the compounds of the present invention in a pharmaceutically acceptable carrier. Pharmaceutically acceptable carriers are also well-known to those who are skilled in the art. The choice of carrier will be determined in part by the particular composition, as well as by the particular method used to administer the composition. Accordingly, there is a wide variety of suitable formulations of the pharmaceutical composition of the present invention.

Formulations suitable for oral administration can consist of (a) liquid solutions, such as an effective amount of the compound dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The present invention also provides methods of using the present inventive compounds/compositions as PK-C agonists, including partial agonists, and antagonists, including partial antagonists. Whether a given compound functions as an agonist or an antagonist can be determined in accordance with assays described herein or in accordance with methods known to those of skill in the art.

Accordingly, the present invention provides a method of inhibiting a protein kinase C-mediated biological response in a mammal in need of such inhibition. The method comprises administering to the mammal a protein kinase C-antagonistic compound of the present invention in an amount sufficient to inhibit the protein kinase C-mediated biological response. Also provided is a method of promoting a protein kinase C-mediated biological response in a mammal in need of such promotion. The method comprises administering to the mammal a protein kinase C-agonistic compound of the present invention in an amount sufficient to promote the protein kinase C-mediated biological response.

One skilled in the art will appreciate that suitable methods of administering the compounds of the present invention to an animal are available, and that, although more than one route can be used to administer a particular composition, a particular route can provide a more immediate and more effective reaction than another route.

The dose administered to an animal, particularly a human, in the context of the present invention should be sufficient to effect a therapeutic response, i.e., inhibition or promotion of a protein kinase C-mediated biological response, in the animal over a reasonable time frame. The dose will be determined by the strength of the particular compound employed, the type of delivery means employed, the route of administration, the condition and weight of the animal to be treated, the timing of administration, and the length of time of administration. The size of the dose also will be determined by the existence, nature, and extent of any adverse side-effects that might accompany the administration of a particular composition. The dose may be administered acutely or chronically as dictated by the condition being treated, alleviated or prevented.

Examples of conditions that can be alleviated or ameliorated by administration of a PK-C agonist in accordance with the present inventive method include leukemia and melanoma. Similarly, examples of conditions that can be alleviated or ameliorated by administration of a PK-C antagonist in accordance with the present inventive method include inflammatory dermatoses, such as psoriasis, seborrheic dermatitis, chloracne, atopic dermatitis, allergic contact dermatitis, lichen simplex chronicus, eczematous dermatitis, erythema multiforme, cutaneous lupus erythematosus and panniculitis, inflammatory conditions, such as vasculitis, chronic bronchitis, chronic glomerulonephritis, chronic gastritis, Crohn's disease, chronic hepatitis and pancreatitis, prostatitis, thyroiditis, rheumatoid arthritis and myositis.

The compounds of the present invention also can be used as reagents in the in vitro and in vivo study of PK-C activation and inhibition.

The following examples serve to illustrate and not to limit the scope of the present invention.

EXAMPLES

All chemical reagents were commercially available. Melting points were determined on a Mel-Temp II apparatus, Laboratory Devices, USA, and are uncorrected. Silica gel column chromatography was performed on silica gel 60, 230–400 mesh (E. Merck). Proton and $^{13}C$ NMR spectra were recorded on a Bruker AC-250 instrument at 250 and 62.9 MHz, respectively. Spectra were referenced to the solvent in which they were run (7.24 ppm for $CDCl_3$). Infrared spectra were recorded on a Perkin-Elmer 1600 Series FTIR. Elemental analyses were performed by Atlantic Microlab, Inc., Atlanta, Ga.

Example 1

This example describes the synthesis of the compound of formula:

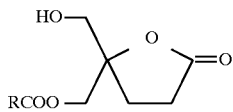

The above compound (referred to as template I) was synthesized according to the following reaction scheme (Scheme 1):

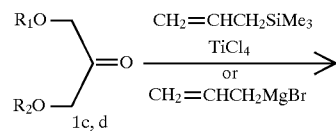

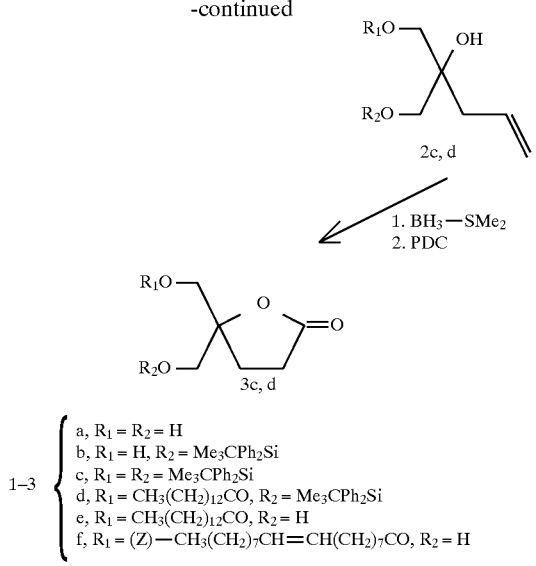

a, $R_1 = R_2 = H$
b, $R_1 = H$, $R_2 = Me_3CPh_2Si$
1–3 { c, $R_1 = R_2 = Me_3CPh_2Si$
d, $R_1 = CH_3(CH_2)_{12}CO$, $R_2 = Me_3CPh_2Si$
e, $R_1 = CH_3(CH_2)_{12}CO$, $R_2 = H$
f, $R_1 = (Z)-CH_3(CH_2)_7CH=CH(CH_2)_7CO$, $R_2 = H$

Two different approaches were followed. Initially, the monoprotected tert-butyldiphenylsilyl ether 1b was treated with myristoyl chloride to give 1d. Alternatively, 1a was fully protected as 1c. Conversion of 1c and 1d to the tertiary homoallylic alcohols 2c and 2d was achieved, respectively, with either allylmagnesium bromide or allyltrimethylsilane/ $TiCl_4$. Hydroboration of the double bond in 2c and 2d was immediately followed by oxidation with pyridinium dichromate (PDC). Under these reaction conditions, the ensuing cyclization to the lactol proceeded with further oxidation to give, respectively, the antepenultimate and penultimate intermediate lactones 3c and 3d. Removal of the silyl ether protection with tetrabutylammonium fluoride (TBAF) afforded the target lactone 3e and the free lactone 3a. Selective acylation of lactone 3a gave the oleate 3f.

1-O-(tert-Butyldiphenylsilyl)-1,3-dihydroxy-2-propanone (1b). tert-Butylchlorodiphenyl-silane (0.76 g, 2.7 mmol) was added over a period of 10 min to a chilled (0° C.) solution of 1,3-dihydroxyacetone (1a, 0.5 g, 2.7 mmol) and dimethylaminopyridine (DMAP, 0.085 g, 0.7 mmol) in dry pyridine (20 mL). The reaction mixture was allowed to reach room temperature, and stirring was continued for a total of 16 h. After the addition of ice-cold water (100 mL), the mixture was extracted with EtOAc (3×20 mL). The combined organic extract was washed with 1N HCl solution (3×10 mL) and water (15 mL), and dried over $Na_2SO_4$. The residue obtained after removing the organic solvent was purified by flash column chromatography over silica gel with mixtures of hexane:EtOAc (95:5 followed by 85:15) as eluants to give 1b (0.472 g, 52%) as an oil; IR (neat) 3443.6 and 1731.7 $cm^{-1}$; $^1H$ NMR ($CDCl_3$) δ 1.10 (s, 9 H, $C(CH_3)_3$), 4.30 (s, 2 H, $CH_2OSi$), 4.60 (s, 2 H, $CH_2OH$), 7.30–7.70 (m, 10 H, Ph); $^{13}C$ NMR δ 19.20, 26.71, 66.76, 68.30, 128.03, 130.23, 132.00, 135.44, 210.28. Anal. Calcd for $C_{19}H_{24}O_3Si$: C, 69.47; H, 7.36. Found: C, 69.36; H, 7.11.

1,3-bis-O-(tert-butyldiphenylsilyl)-1,3-dihydroxy-2-propanone (1c). tert-Butylchlorodiphenyl-silane (50 g, 181.9 mmol) was added over a period of 30 min to a chilled (0° C.) solution of 1,3-dihydroxyacetone (1a, 7.28 g, 0.42 mmol) and DMAP (2.47 g, 20.2 mmol) in dry pyridine (100 mL). The reaction mixture was allowed to reach room temperature, and stirring was continued for a total of 4 days. The reaction mixture was poured over crushed ice (500 g) and left overnight. The precipitated solid was filtered and washed with water (ca. 500 mL). The filtrate was extracted with EtOAc (3×150 mL) and the combined organic extract was washed with 1N HCl (3×100 mL), water (2×100 mL), dried ($Na_2SO_4$), and evaporated under reduced pressure to give a white solid. The solid was recrystallized from EtOAc/hexane to give 1c (41.7 g, 91%) as a white solid, mp 100°–101° C.; IR (KBr) 1749.7 $cm^{-1}$; $^1H$ NMR ($CDCl_3$) δ 1.05 (s, 18 H, $C(CH_3)_3$), 4.40 (s, 4 H, $CH_2OSi$), 7.30–7.60 (m, 20 H, Ph); $^{13}C$ NMR δ 19.17, 26.68, 68.53, 127.81, 129.91, 132.58, 135.46. Anal. Calcd for $C_{35}H_{42}O_3Si_2$: C, 74.15; H, 7.47. Found: C, 74.12; H, 7.50.

3-O-Tetradecanoyl-1-O-(tert-butyldiphenylsilyl)-1,3-dihydroxy-2-propanone (1d). A solution of 1b (0.170 g, 0.52 mmol), dry pyridine (0.204 g, 2.6 mmol), and DMAP (0.010 g, 0.08 mmol) in dry $CH_2Cl_2$ (12 mL) was treated with myristoyl chloride (0.255 g, 1.03 mmol), and the resulting mixture was stirred under argon for 24 h. After volatiles were removed, the residue was partitioned in a mixture of ether (20 mL) and 1N HCl (10 mL). The ether layer was washed consecutively with 1N HCl (10 mL) and water (10 mL), and dried ($Na_2SO_4$). The solvent was removed and the residue obtained was purified by flash column chromatography over silica gel with hexane:EtOAc (96:4) as eluant to provide 1d (0.215 g, 77%) as an oil; IR (neat) 1740.0 $cm^{-1}$; $^1H$ NMR ($CDCl_3$) δ 0.90 (distorted t, 3 H, $CH_3$), 1.10 (s, 9 H, $C(CH_3)_3$), 1.20–1.40 (m, 20 H, $CH_3(CH_2)_{10}CH_2CH_2CO$); 1.65 (m, 2 H, $CH_3(CH_2)_{10}CH_2CH_2CO$), 2.40 (t, J=7.5 Hz, 2 H, $CH_3(CH_2)_{10}CH_2CO$), 4.25 (s, 2 H, $CH_2OSi$), 5.02 (s, 2 H, $CH_2OCO$), 7.45–7.65 (m, 10 H, Ph); $^{13}C$ NMR δ 14.10, 19.17, 22.67, 24.85, 26.71, 29.07, 29.25, 29.33, 29.43, 29.59, 29.63, 29.65, 31.90, 33.82, 66.76, 68.78, 127.99, 130.16, 132.04, 135.44, 173.07, 203.31. Anal. Calcd for $C_{33}H_{50}O_4Si$: C, 73.56; H, 9.36. Found: C, 73.68; H, 9.33.

2-Hydroxy-2-[(tert-butyldiphenylsilyloxy)methyl]-1-tert-butyldiphenylsilyloxy-4-pentene (2c). A stirred solution of 1c (1.0 g, 1.76 mmol) in THF (12 mL) at 0° C. was treated with a solution of allylmagnesium bromide (2M, 1.76 mL), which was added dropwise over a period of 5 min. The reaction was stirred at 0° C. for 1 h, quenched with 1N HCl (5 mL), and concentrated under reduced pressure. The residue was extracted with EtOAc (2×20 mL) and the organic extract was washed with water (10 mL), dried ($NaSO_4$) and concentrated under vacuum. The residue obtained was purified by flash column chromatography using silica gel and hexane/EtOAc (98:2) to give 2c (0.99 g, 93%) as a colorless liquid; IR (neat) 3365.8, 1427 $cm^{-1}$; $^1H$ NMR ($CDCl_3$) δ 1.05 (s, 18 H, $C(CH_3)_3$), 2.35 (d, J=7.2 Hz, 2 H, $CH_2CH=CH_2$), 2.50 (s, 1 H, OH), 3.65 (AB q, J=9.8 Hz, 4 H, $CH_2OSi$), 5.00 (m, 2 H, $CH=CH_2$), 5.75 (m, 1 H, $CH=CH_2$), 7.30–7.70 (m, 20 H, Ph); $^{13}C$ NMR δ 19.28, 26.88, 38.40, 66.05, 74.39, 117.97, 127.70, 129.71, 133.08, 133.29, 135.62. Anal. Calcd for $C_{38}H_{48}O_3Si_2$: C, 74.96; H, 7.75. Found: C, 74.78; H, 7.82.

2-Hydroxy-2-[(tert-butyldiphenylsilyloxy)methyl]-1-tetradecanoyloxy-4-pentene (2d). A solution of $TiCl_4$ in $CH_2Cl_2$ (1M, 6.3 mL) was added to a stirred solution of 1d (2.25 g, 4.2 mmol) in $CH_2Cl_2$ (50 mL) at room temperature. After 5 min., neat allyltrimethylsilane (1.43 g, 12.5 mmol) was rapidly added and stirring was continued for 40 min. The reaction was quenched with ice-cold water (50 mL) and extracted with ether (3×50 mL). The combined ether extract was washed with water (3×25 mL), dried ($Na_2SO_4$) and evaporated under reduced pressure. The residue was chromatographed by flash column over silica gel. The appropriate fractions, eluted with hexane containing increasing proportions of EtOAc (3–4%), were combined and evaporated under reduced pressure to give 2d (1.87 g, 77%) as an oil;

IR (neat) 3486.9, 1742.1 cm$^{-1}$; $^1$H NMR (CDCl$_3$) δ 0.85 (distorted t, 3 H, CH$_3$), 1.10 (s, 9 H, C(CH$_3$)$_3$), 1.30 (m, 20 H, CH$_3$(C$\underline{H}_2$)$_{10}$CH$_2$CH$_2$CO), 1.60 (m, 2 H, CH$_3$(CH$_2$)$_{10}$C$\underline{H}_2$CH$_2$CO), 2.25 (t, J=7.4 Hz, 2 H, CH$_3$(CH$_2$)$_{10}$CH$_2$C$\underline{H}_2$CO), 2.35 (br d, J=8.3 Hz, 2 H, C$\underline{H}_2$CH=CH$_2$), 2.50 (s, 1 H, OH), 3.52 (s, 2 H, CH$_2$OSi), 4.10 (AB q, J=13.4 Hz, 2 H, CH$_2$OCO), 5.00–5.10 (m, 2 H, CH=C$\underline{H}_2$), 5.70–5.90 (m, 1 H, C$\underline{H}$=CH$_2$), 7.30–7.70 (m, 10 H, Ph); $^{13}$C NMR δ 14.10, 19.26, 22.67, 24.88, 26.84, 29.15, 29.25, 29.34, 29.45, 29.59, 29.63, 29.66, 31.90, 34.18, 38.88, 66.08, 66.12, 73.23, 118.91, 127.77, 129.87, 132.38, 135.58, 173.64. Anal. Calcd for C$_{36}$H$_{56}$O$_4$Si: C,74.43; H, 9.72. Found: C,74.49; H, 9.67.

5-bis-[(tert-Butyldipheylsilyloxy)methyl]-tetrahydro-2-furanone (3c). A stirred solution of 2c (1.92 g, 3.15 mmol) in dry THF (30 mL) at −78° C. was treated dropwise with a THF solution of BH$_3$·SMe$_2$ (2M, 3.15 mL) while maintained under a blanket of argon. The reaction mixture was allowed to reach room temperature during the course of 24 h and then it was concentrated under reduced pressure. The residue obtained was dissolved in dry CH$_2$Cl$_2$ (100 mL) and treated with pyridinium chlorochromate (PCC,15 g, 69.5 mmol). The dark reaction mixture was stirred at room temperature for 36 h and was diluted with dry ether (200 mL) before being filtered through a short silica gel column. The solution obtained was dried (Na$_2$SO$_4$), evaporated, and the residue was purified by flash column chromatography over silica gel using hexane:EtOAc (94:6) as eluant to give 3c (1.28 g, 65%) as a white solid, mp 125.5°–126.3° C. (EtOAc/hexane); IR (KBr) 1784.5 cm$^{-1}$; $^1$H NMR (CDCl$_3$) δ 1.05 (s, 18 H, C(CH$_3$)$_3$), 2.20 (distorted t, 2 H, H-4), 2.65 (distorted t, 2 H, H-3), 3.70 (AB q, J=10.9 Hz, 4 H, CH$_2$OSi), 7.30–7.70 (m, 10 H, Ph); $^{13}$C NMR δ 19.19, 25.69, 26.56, 27.39, 26.87, 29.41, 66.46, 88.23, 127.72, 127.82, 129.88, 132.52, 132.77, 135.55, 135.61, 177.14. Anal. Calcd for C$_{38}$H$_{46}$O$_4$Si$_2$: C,73.28; H,7.45. Found: C,73.14; H,7.49.

5-bis(Hydroxymethyl)tetrahydro-2-furanone (3a). A solution of 3c (0.62 g, 1 mmol) and ammonium fluoride (0.37 g, 10 mmol) in MeOH (30 mL) was stirred at room temperature for 4 days. The reaction mixture was concentrated under reduced pressure and the residue was purified by flash column chromatography over silica gel using EtOAc:MeOH (95:5) as eluant to give 3a (0.058 g, 40%) as a clear liquid; IR (neat) 3415.9, 1760.1 cm$^{-1}$; $^1$H NMR (CDCl$_3$) δ 2.15 (distorted t, 2 H, H-4), 2.65 (m, 4 H, H-3, 2×OH), 3.65 (dd, J=12.1, 6.0 Hz, 2 H, C$\underline{H}_2$OH), 3.80 (dd, J=12.1, 6.2 Hz, C$\underline{H}_2$OH); $^{13}$C NMR δ 25.10, 29.17, 65.24, 88.48, 177.57. Anal. Calcd for C$_6$H$_{10}$O$_4$: C,49.30; H, 6.90. Found: C, 49.08; H, 6.96.

5-[(tert-Butyldiphenylsilyloxy)methyl]-5-[(tetradecanoyloxy)methyl]-tetrahydro-2-furanone (3d). A stirred solution of 2d (1.04 g, 1.8 mmol) in dry THF (35 mL) at −78° C. was treated dropwise with a THF solution of BH$_3$·SMe$_2$ (2M, 1.8 mL) while maintained under a blanket of argon. The reaction mixture was allowed to reach room temperature during the course of 3 h and was stirred further for 12 h. Evaporation of the solvent under reduced pressure gave a residue that was dissolved in dry CH$_2$Cl$_2$ (100 mL) and treated with pyridinium chlorochromate (PCC, 15 g, 69.5 mmol). The dark reaction mixture was stirred at room temperature for 3 days and was diluted with dry ether (500 mL) before being filtered through a short silica gel column. The solution obtained was dried (Na$_2$SO$_4$) and reduced to dryness. The residue was purified by flash column chromatography over silica gel using 10% EtOAc in hexane as eluant to give 3d (0.758 g, 71%) as a pale yellow oil; IR (neat) 1785.6, 1743.5 cm$^{-1}$; $^1$H NMR (CDCl$_3$) δ 0.87 (distorted t, 3 H, CH$_3$), 1.05 (s, 9 H, C(CH$_3$)$_3$), 1.25 (m, 20 H, CH$_3$(C$\underline{H}_2$)$_{10}$CH$_2$CH$_2$CO); 1.55 (m, 2 H, CH$_3$(CH$_2$)$_{10}$C$\underline{H}_2$CH$_2$CO), 2.00–2.40 (m, 4 H, H-4, CH$_3$(CH$_2$)$_{10}$C$\underline{H}_2$CH$_2$CO), 2.60 (m, 2 H, H-3), 3.70 (AB q, J=10.8 Hz, 2 H, CH$_2$OSi), 4.20 (AB q, J=12.0 Hz, 2 H, CH$_2$OCO), 7.30–7.70 (m, 10 H, Ph); $^{13}$C NMR δ 14.10, 19.17, 22.67, 24.78. 25.91, 26.72, 28.87, 29.08, 29.20, 29.33, 29.41, 29.57, 29.62, 31.90, 34.03, 65.64, 66.15, 85.77, 127.88, 130.01, 132.25, 132.50, 135.52, 135.59, 173.15, 176.28. Anal. Calcd for C$_{36}$H$_{54}$O$_5$Si: C,72.68; H, 9.16. Found: C,72.76; H, 9.22.

5-[(tetradecanoyloxy)methyl]-5-hydroxymethyl-tetrahydro-2-furanone (3e). A solution of 3d (0.118 g, 0.2 mmol) in THF (3 mL) at room temperature was stirred with a solution of n-tetrabutylammonium fluoride in THF (1M, 0.3 mL) for 40 min. The solution was evaporated under vacuum, dissolved in EtOAc (20 mL), dried (Na$_2$SO$_4$) and concentrated. The residue obtained was purified by flash column chromatography over silica gel using hexane:EtOAc (7:3) as eluant to give 3e (0.051 g, 72%) as a white solid; mp 65°–66° C. (EtOAc/hexane); IR (KBr) 3448.1, 1763.2, 1728.1 cm$^{-1}$; $^1$H NMR (CDCl$_3$) δ 0.88 (distorted t, 3 H, CH$_3$), 1.30 (m, 20 H, CH$_3$(C$\underline{H}_2$)$_{10}$CH$_2$CH$_2$CO); 1.60 (m, 2 H, CH$_3$(CH$_2$)$_{10}$C$\underline{H}_2$CH$_2$CO), 2.00–2.12 (m, 2 H, H-4$_a$), 2.20–2.30 (m, 2 H, H-4$_b$), 2.33 (t, J=7.6 Hz, 2 H, CH$_3$(CH$_2$)$_{10}$CH$_2$C$\underline{H}_2$CO), 2.45 (t, J=6.4 Hz, 1 H, OH), 2.65 (m, 2 H, H-3), 3.60 (dd, J=12.1, 5.9 Hz, 1 H, C$\underline{H}$HOH), 3.75 (dd, J=12.1, 6.1 Hz, CH$\underline{H}$OH), 4.10 (d, J=12.0 Hz, 1 H, C$\underline{H}$HOCO), 4.30 (d, J=12.0 Hz, 1 H, CH$\underline{H}$OCO); $^{13}$C NMR δ 14.09, 22.65, 24.81, 25.47, 28.79, 29.07, 29.19, 29.32, 29.41, 29.56, 29.60, 31.89, 34.03, 64.82, 65.45, 86.02, 173.48, 176.47; FAB MS (m/z, relative intensity) 357 (MH$^+$, 100), 211 (C$_{13}$H$_{27}$CO$^+$, 35). Anal. Calcd for C$_{20}$H$_{36}$O$_5$: C,67.37; H,10.18. Found: C,67.30; H,10.17.

5-{[(Z)-9-octadecenoyloxy]methyl}-5-hydroxymethyl-tetrahydro-2-furanone (3f). A stirred solution of 3a (0.025 g, 0.17 mmol), dry pyridine (68 mg), and DMAP (2 mg) in dry CH$_2$Cl$_2$ (5 mL) at 0° C. was treated with oleoyl chloride (0.051 g, 0.17 mmol). After 1 h, the reaction was quenched with water (3 mL) and the resulting layers were separated. The aqueous layer was extracted with CH$_2$Cl$_2$ (1×5 mL) and the combined organic extract was washed with 1N HCl (5 mL), water (5 mL), and dried (Na$_2$SO$_4$). The solvent was evaporated and the residue obtained was purified by flash column chromatography over silica gel using hexane:EtOAc (65:35) as eluant to give 3f (0.046 g, 66%) as a white solid, mp 38.5°–39.5° C. (EtOAc/hexane); IR (KBr) 3447.9, 1780, 1738.8 cm$^{-1}$; $^1$H NMR (CDCl$_3$) δ 0.86 (distorted t, 3 H, CH$_3$), 1.30 (m, 20 H, CH$_3$(C$\underline{H}_2$)$_6$CH$_2$CH=CHCH$_2$(C$\underline{H}_2$)$_4$CH$_2$CH$_2$CO); 1.60 (m, 2 H, CH$_3$(CH$_2$)$_6$C$\underline{H}_2$CH=CHCH$_2$(CH$_2$)$_4$C$\underline{H}_2$CH$_2$CO), 1.90–2.10 (m, 5 H, C$\underline{H}_2$CH=CHC$\underline{H}_2$, H-4$_a$), 2.20–2.40 (m, 3 H, CH$_3$(CH$_2$)$_6$CH$_2$CH=CHCH$_2$(CH$_2$)$_4$CH$_2$C$\underline{H}_2$CO, H-4$_b$), 2.65 (m, 2 H, H-3), 3.61 (d, J=12.1 Hz, 1 H, C$\underline{H}$HOH), 3.75 (d, J=12.1 Hz, CH$\underline{H}$OH), 4.12 (d, J=12.0 Hz, 1 H, C$\underline{H}$HOCO), 4.30 (d, J=12.0 Hz, 1 H, CH$\underline{H}$OCO), 5.32 (m, 2 H, CH=CH); $^{13}$C NMR δ 14.09, 22.65, 24.80, 25.48, 27.13, 27.19, 28.76, 29.05, 29.10, 29.29, 29.50, 29.66, 29.73, 31.87, 34.02, 64.82, 65.44, 85.93, 129.67, 130.01, 173.45, 176.36; FAB MS (m/z, relative intensity) 411 (MH$^+$, 37), 265 (C$_{17}$H$_{33}$CO$^+$, 11). Anal. Calcd for C$_{24}$H$_{42}$O$_5$: C, 70.19; H, 10.32. Found: C, 70.11; H, 10.37.

Example 2

This example describes the synthesis of the compound of formula:

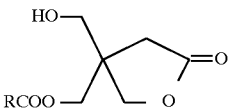

The above compound (referred to as template II) was synthesized according to the following reaction scheme (Scheme 2):

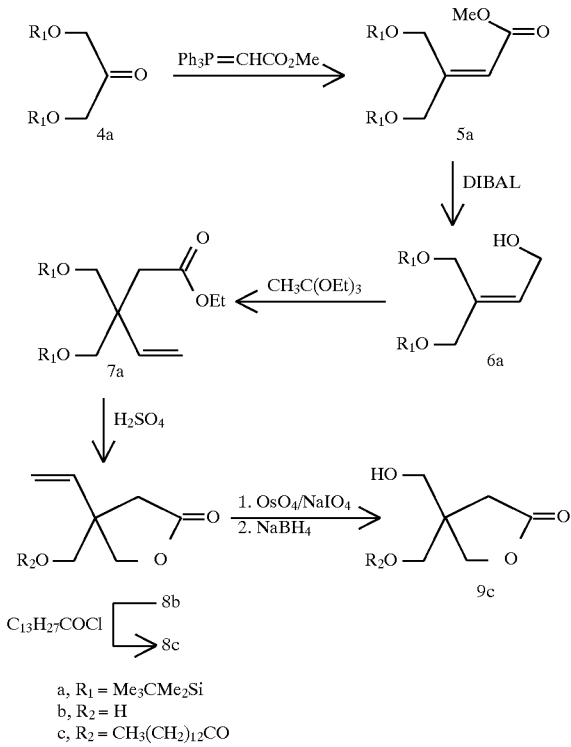

a, $R_1$ = $Me_3CMe_2Si$
b, $R_2$ = H
c, $R_2$ = $CH_3(CH_2)_{12}CO$

The same starting material as in Example 1 was used, but this time protection was achieved with the less sterically demanding tert-butyldimethylsilyl chloride to give 4a. Wadsworth-Emmons reaction of 4a with the stabilized ylide methyl (triphenyl phosphoranylidene)acetate gave 5a, which was reduced to the allylic alcohol 6a with diisobutylaluminum hydride (DIBAL). Claisen rearrangement of the intermediate enol ester, formed by reacting 6a with triethylorthoacetate, produced the pivotal ester 7a, which cyclized to lactone 8b under acidic conditions. Acylation of the primary alcohol function provided the myristate ester 8c, and oxidation of the terminal olefin with $OsO_4$/$NaIO_4$ gave the corresponding aldehyde, which was readily converted to the desired target lactone 9c after borohydride reduction.

1,3-bis-O-(tert-butyldimethylsilyl)-1,3-dihydroxy-2-propanone (4a). This compound was prepared in the same fashion as 1c, according to Kinder et al., J. Label. Compds. Radiopharm. 31: 829 (1992).

Methyl 3,3-bis[(tert-butyldimethylsiloxy)methyl]acrylate (5a). A solution of 4a (12.74 g, 40 mmol) in benzene (200 mL) was treated with methyl(triphenylphosphoranylidene)acetate (16.05 g, 48 mmol) and refluxed for 8 h. The reaction mixture was cooled and concentrated under reduced pressure. The residue was dissolved in hexane, filtered and the filtrate was concentrated. The residue was purified by flash column chromatography over silica gel with hexane:EtOAc (19:1) as eluant to give 5a (13.48 g, 90%) as an oil; IR (neat) 1719.4, 1654.2; $^1$H NMR ($CDCl_3$) δ 0.04 and 0.06 (s, 6 H, $SiCH_3$), 0.87 and 0.91 (s, 9 H, $C(CH_3)_3$), 3.67 (s, 3 H, $CO_2CH_3$), 4.42 (m, 2 H, $CH_2OSi$), 4.85 (m, 2 H, $CH_2OSi$), 5.98 (m, 1 H, =CH); $^{13}$C NMR ($CDCl_3$) δ -2.14, 18.15, 18.37, 25.76, 25.88, 50.99, 61.55, 63.17, 111.33, 162.07, 166.96. Anal. Calcd for $C_{18}H_{38}O_4Si_2$: C, 57.70; H, 10.22. Found: C, 57.82; H, 10.21.

3,3-Bis[(tert-butyldimethylsiloxy)methyl]-2-propen-1-ol (6a). A solution of 5a (11.24 g, 30 mmol) in $CH_2Cl_2$ (100 mL) was cooled to -60° C. and treated dropwise with a solution of diisobutylaluminum hydride in $CH_2Cl_2$ (1.0M, 40 mL). The reaction mixture was quenched with saturated potassium sodium tartrate tetrahydrate and warmed to room temperature. The aqueous layer was extracted with $CH_2Cl_2$, and the combined organic layer was washed with water and brine. The organic layer was dried ($NaSO_4$) and concentrated. The residue was purified by flash column chromatography over silica gel with hexane:EtOAc (5:1) as eluant to give 6a (9.77 g, 94%) as an oil: IR (neat) 3357, 1471 cm$^{-1}$; $^1$H NMR ($CDCl_3$) δ 0.05 and 0.06 (s, 6 H, $SiCH_3$), 0.88 and 0.89 (s, 9 H, $C(CH_3)_3$), 1.86 (br s, 1 H, OH), 4.14 (br s, 2 H, $CH_2OH$), 4.20 (m, 4 H, $CH_2OSi$), 5.80 (m, 1 H, =CH); $^{13}$C NMR ($CDCl_3$) δ -1.95, 18.19, 18.33, 25.62, 25.79, 25.88, 58.50, 59.24, 64.75, 125.47, 140.81. Anal. Calcd for $C_{17}H_{38}O_3Si_2$: C, 58.90; H: 11.05. Found: C, 59.00; H, 11.00.

Ethyl 3,3-bis[(tert-butyldimethylsiloxy)methyl]-4-pentenoate (7a). A mixture of 6a (9.36 g, 27 mmol), triethyl orthoacetate (34.75 mL, 189 mmol) and propionic acid (0.2 mL, 2.7 mmol) was heated at 138° C. for 20 h with removal of ethanol. The reaction mixture was cooled and concentrated under vacuum, and the residue was purified by flash column chromatography over silica gel with hexane:EtOAc (19:1) as eluant to give 7a (8.77 g, 78%) as an oil; IR (neat) 1737, 1471 cm$^{-1}$; $^1$H NMR ($CDCl_3$) δ 0.01 (br s, 12 H, $SiCH_3$), 0.85 (br s, 18 H, $C(CH_3)_3$), 1.21 (t, 3 H, $CH_3CH_2$), 2.42 (s, 2 H, $CH_2COEt$), 3.61 (AB q, J=9.3 Hz, 4 H), 4.06 (q, 2 H, $CH_2CH_3$), 5.06 (m, 2 H, CH=$CH_2$), 5.84 (dd, J=19.9, 11.3, 1 H, $CH$=$CH_2$); $^{13}$C NMR ($CDCl_3$) δ -5.58, 14.24, 18.23, 25.84, 36.81, 45.97, 59.84, 64.63, 114.47, 139.73, 171.87. Anal. Calcd for $C_{21}H_{44}O_4Si_2$: C, 60.52; H, 10.64. Found: C, 60.46; H, 10.62.

4-Hydroxymethyl-4-vinyltetrahydro-2-furanone (8b). A solution of 7a (8.34 g, 20 mmol) in aqueous THF (60 mL, 1:1) was treated with concentrated $H_2SO_4$ (10 mL) and stirred at room temperature for 24 h. The mixture was concentrated under vacuum, diluted with water, and the aqueous layer was extracted with $CHCl_3$. The combined organic layer was washed with $H_2O$, dried ($NaSO_4$) and concentrated. The residue was purified by flash column chromatography over silica gel with EtOAc/hexane (2:1) as eluant to give 8b (2.50 g, 88%) as an oil; IR (neat) 3452 (OH), 1777 (C=O), 1641 cm$^{-1}$; $^1$H NMR ($CDCl_3$) δ 2.51 (d of AB, J=17.4 Hz, 1 H, H-$3_a$), 2.63 (d of AB, J=17.4 Hz, 1 H, H-$3_b$), 3.62 (s, 2 H, $CH_2OH$), 4.16 (d of AB, J=9.2 Hz, 1 H, H-$5_a$), 4.32 (d of AB, J=9.2 Hz, 1 H, H-$5_b$), 5.19 (d, J=17.5 Hz, 1 H, CH=$CHH$), 5.29 (d, J=10.8 Hz, 1 H, CH=$CHH$), 5.85 (dd, J=17.5, 10.8 Hz, 1 H, $CH$=$CH_2$); $^{13}$C NMR ($CDCl_3$) δ 35.94, 47.61, 65.56, 73.33, 116.18, 137.55, 176.97. Anal. Calcd for $C_7H_{10}O_3$: C, 59.14; H. 7.09. Found: C, 59.05; H, 7.09.

4-(Tetradecanoyloxy)methyl-4-vinyltetrahydro-2-furanone (8c). A solution of 8b (0.2 g, 1.4 mmol) in $CH_2Cl_2$ (20 mL) was treated with pyridine (0.45 mL, 5.6 mmol), dimethylaminopyridine (0.034 g, 0.28 mmol), and tetradecanoyl chloride (0.76 mL, 2.8 mmol). After stirring for 2 h at room temperature, the reaction mixture was concentrated, and residue was purified by flash column chromatography over silica gel with hexane:EtOAc (3:1) as eluant to give 8c (0.49 g, 99%) as an oil: IR (neat) 1788 and 1741 cm$^{-1}$ (C=O); $^1$H NMR (CDCl$_3$) δ 0.86 (distorted t, 3 H, CH$_3$), 1.25 (m, 20 H, CH$_3$(CH$_2$)$_{10}$CH$_2$CH$_2$CO), 1.60 (m, 2 H, CH$_3$(CH$_2$)$_{10}$CH$_2$CH$_2$CO), 2.31 (t, J=7.4 Hz, 2 H, CH$_3$(CH$_2$)$_{10}$CH$_2$CH$_2$CO), 2.60 (s, 2 H, H-3), 4.12 (AB q, J=11.3 Hz, 2 H, CH$_2$OCOC$_{13}$H$_{27}$), 4.20 (AB q, J=9.3 Hz, 2 H, H-5), 5.19 (d, J=17.6 Hz, 1 H, CH=CHH), 5.28 (d, J=10.9 Hz, 1 H, CH=CHH), 5.84 (dd, J=10.9, 17.6 Hz, CH=CH$_2$), $^{13}$C NMR (CDCl$_3$) δ 14.02, 22.58, 24.69, 28.99, 29.11, 29.24, 29.34, 29.48, 29.53, 29.56, 31.81, 33.93, 36.57, 45.76, 66.63, 73.60, 116.63, 136.81, 173.27, 175.03. Anal. Calcd for C$_{21}$H$_{36}$O$_4$: C, 71.55; H: 10.30. Found. C, 71.46; H, 10.30.

4-Hydroxymethyl-4-(tetradecanoyloxy)methyl-4-vinyltetrahydro-2-furanone (9c). A stirring solution of 8c (0.49 g, 1.4 mmol) in aqueous acetone (1:1, 20 mL) was treated with 4-methylmorpholine N-oxide (0.33 g, 2.8 mmol), sodium metaperiodate (0.6 g, 2.8 mmol), and osmium tetroxide (2.5 wt. % solution in t-butanol, 1.75 mL, 0.14 mmol) for 20 h at room temperature. The reaction mixture was quenched with saturated sodium thiosulfate solution (10 mL), stirred for 10 min, and extracted with EtOAc. The combined organic layer was washed with water, dried (Na$_2$SO$_4$), and concentrated. The residue was purified by flash column chromatography over silica gel with EtOAc/hexane (1:1) as eluant to give the corresponding aldehyde (0.432 g, 88%) as a white solid: mp 63° C.; IR (KBr) 1784, 1767 and 1735 cm$^{-1}$ (C=O); $^1$H NMR (CDCl$_3$) δ 0.86 (distorted t, 3 H, CH$_3$), 1.25 (m, 20 H, CH$_3$(CH$_2$)$_{10}$CH$_2$CH$_2$CO), 1.60 (m, 2 H, CH$_3$(CH$_2$)$_{10}$CH$_2$CH$_2$CO), 2.30 (t, J=7.4 Hz, 2 H, CH$_3$(CH$_2$)$_{10}$CH$_2$CH$_2$CO), 2.54 (d of AB, J=17.9 Hz, 1 H, H-3$_a$), 2.92 (d of AB, J=17.9 Hz, 1 H, H-3$_b$), 4.21 (d of AB, J=9.9 Hz, 1 H, H-5$_a$), 4.38 (AB q, J=11.65 Hz, 2 H, CH$_2$OCOC$_{13}$H$_{27}$), 4.55 (d of AB, J=9.9 Hz, 1 H, H-5$_b$), 9.66 (s, 1 H, CHO); $^{13}$C NMR (CDCl$_3$) δ 14.05, 22.62, 24.67, 28.98, 29.12, 29.28, 29.36, 29.51, 29.56, 31.84, 32.11, 33.76, 54.27, 63.49, 68.66, 173.10, 173.30, 196.71, 196.86. Anal. Calcd for C$_{20}$H$_{34}$O$_5$: C, 67.76; H, 9.67. Found: C, 67.99; H, 9.77.

This aldehyde (0.425 g, 1.2 mmol) was dissolved in MeOH (15 mL), cooled to -10° C. and treated with sodium borohydride (0.09 g, 2.4 mmol). After stirring for 30 min, the reaction mixture was quenched by the slow addition of a phosphate buffer (pH 4, 5 mL) and extracted with ether. The organic layer was washed with water, dried (Na$_2$SO$_4$), and concentrated. The residue was purified by flash column chromatography over silica gel with EtOAc/hexane (1:1) as eluant to give 9c (0.35 g, 82%) as a white solid: mp 50° C.; IR (KBr) 3461 (OH), 1764 and 1739 cm$^{-1}$(C=O); $^1$H NMR (CDCl$_3$) δ 0.86 (distorted t, 3 H, CH$_3$), 1.25 (m, 20 H, CH$_3$(CH$_2$)$_{10}$CH$_2$CH$_2$CO), 1.60 (m, 2 H, CH$_3$(CH$_2$)$_{10}$CH$_2$CH$_2$CO), 2.33 (t, J=7.4 Hz, 2 H, CH$_3$(CH$_2$)$_{10}$CH$_2$CH$_2$CO), 2.50 (AB q, J=17.8 Hz, 2 H, H-3) 3.58 (bs, 2 H, CH$_2$OH), 4.15 (AB q, J=9.6 Hz, H-5) 4.17 (s, 2 H, C H$_2$OCOC$_{13}$H$_{27}$); $^{13}$C NMR (CDCl$_3$) δ13.99, 22.56, 24.73, 29.00, 29.10, 29.22, 29.33, 29.48, 29.52, 29.54, 31.79, 33.94, 34.04, 45.17, 63.47, 64.78, 72.05, 173.93, 176.19; FAB MS m/z (relative intensitiy) 357 (MH$^+$, 59), 211 (C$_{13}$H$_{27}$CO$^+$, 55). Anal. Calcd for C$_{20}$H$_{36}$O$_5$: C, 67.38; H, 10.18. Found: C, 67.28; H, 10.20.

Example 3

This example describes the synthesis of the compound of formula:

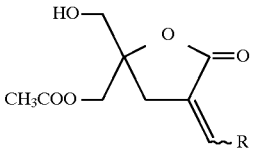

The above compound was synthesized according to the following reaction scheme (Scheme 3):

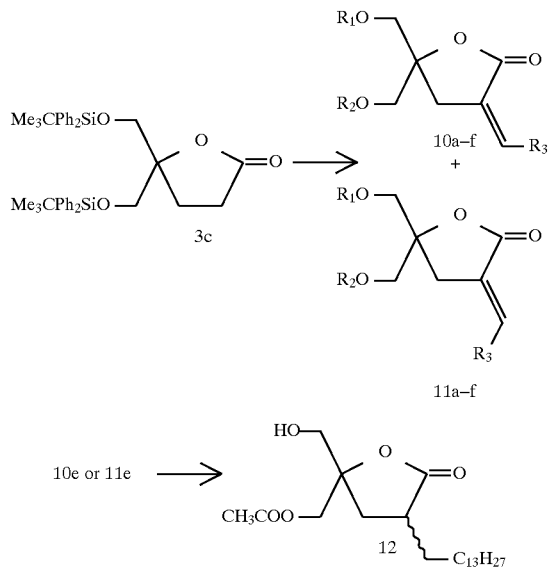

a, R$_1$=R$_2$=Me$_3$CPh$_2$Si, R$_3$=CH$_3$(CH$_2$)$_{12}$
b, R$_1$=R$_2$=Me$_3$CPh$_2$Si, R$_3$=(Z)—CH$_3$(CH$_2$)$_7$CH=CH(CH$_2$)$_7$
c, R$_1$=R$_2$=H, R$_3$=CH$_3$(CH$_2$)$_{12}$
d, R$_1$=R$_2$=H, R$_3$=(Z)—CH$_3$(CH$_2$)$_7$CH=CH(CH$_2$)$_7$
e, R$_1$=CH$_3$CO, R$_2$=H, R$_3$=CH$_3$(CH$_2$)$_{12}$
f, R$_1$=CH$_3$CO, R$_2$=H, R$_3$=(Z)—CH$_3$(CH$_2$)$_7$CH=CH(CH$_2$)$_7$

Lactone 3c was treated with the corresponding aldehyde (myristoyl or oleoyl aldehyde) to give around 70% of the intermediate alcohol, which was readily dehydrated to a separable mixture of the corresponding Z-(10a and 10b) and E-isomers (11a and 11b). Removal of the protective ether functions from these compounds, followed by formation of the corresponding monoacetates, gave the desired targets 10e, 10f, 11e and 11f. Catalytic hydrogenation of either 10e or 11e afforded compound 12 as a mixture of epimers.

(Z)-5-bis-[(tert-Butyldiphenylsilyloxy)methyl]-3-(tetradecanylidene)-tetrahydro-2-furanone (10a) and (E)-5-bis-[(tert-Butyldiphenylsilyloxy)methyl]-3-(tetradecanylidene)-tetrahydro-2-furanone (11a). A solution of 3c (0.685 g, 1.10 mmol) in anhydrous THF (10 mL) at -78° C. was treated with lithium diisopropylamide (2M in heptane/THF/ethylbenzene, 1.37 mL) and stirred for 1 h. A solution of ZnCl$_2$ (0.5M in THF, 2.3 mL) was added, and, after 5 min, a solution of 1-tetradecanal (0.280 g, 1.32 mmol) in THF (9 mL) was introduced into the reaction mixture dropwise. After 1.3 h, the reaction was quenched with a saturated NH$_4$Cl solution (10 mL), and the temperature was allowed to reach ambient conditions. The layers were separated and the aqueous layer was extracted with EtOAc (3×15 mL). The combined organic extract was washed with water (15 mL) and dried ($Na_2SO_4$). The solvent was evaporated and the residue was purified by flash column chromatography over silica gel using hexane:EtOAc (95:5) as eluant to give the corresponding β-hydroxylactone intermediate (0.641 g, 70%) as a clear liquid; IR (neat) 3510.4, 1752.5 $cm^{-1}$; $^1H$ NMR ($CDCl_3$) δ 0.90 (distorted t, 3 H, $CH_3$), 1.10 (m, 18 H, $C(CH_3)_3$), 1.20–1.50 (m, 24 H, (C$\underline{H}_2)_{12}CH_3$), 1.90 (distorted t, 1 H, H-$4_a$), 2.20 (dd, J=12.7, 10.1 Hz, 1 H, H-$4_b$), 2.85 (dd, J=19.5, 10.1 Hz, 1 H, H-3), 3.60–3.80 (m, 4 H, $CH_2OSi$), 4.00 (s, 1 H, OH), 7.30–7.70 (m, 20 H, Ph); $^{13}C$ NMR δ 14.13, 19.15, 19.21, 22.69, 24.86, 26.56, 26.73, 26.77, 28.99, 29.36, 29.66, 29.69, 31.92, 34.83, 45.87, 65.76, 66.40, 72.16, 86.84, 127.70, 127.80, 127.90, 129.62, 129.90, 129.99, 132.24, 132.54, 132.62, 132.68, 134.79, 135.52, 135.57, 135.61, 179.56. Anal. Calcd for $C_{52}H_{74}O_5Si_2$: C, 74.77; H, 8.93. Found: C, 74.60; H, 8.98.

A solution of this compound (0.583 g, 0.68 mmol) and triethylamine (0.343 g, 3.4 mmol) in dry $CH_2Cl_2$ (12 mL) was treated with methanosulfonyl chloride (0.196 g, 1.7 mmol) and the resulting mixture was stirred for 75 min. The reaction mixture was cooled to 0° C. and treated with 1,8-diazabicyclo[5.4.0]undec-7-ene (DBU, 0.624 g, 4 mmol). The reaction mixture was allowed to reach room temperature, and stirring continued for a total of 4 h. The volatiles were removed under vacuum and the residue was treated with 1N HCl (10 mL) and extracted with EtOAc (3×10 mL). The combined organic extract was washed with 1N HCl (2×20 mL), water (5 mL) and dried ($Na_2SO_4$). The residue was purified by flash column chromatography over silica gel using hexane:EtOAc (98:2) to give 10a (0.172 g, 30%) as the more polar compound, followed by 11a (0.345 g, 60.5%). Both compounds were isolated as oils: 10a, IR (neat) 1759.6, 1670.2 $cm^{-1}$; $^1H$ NMR ($CDCl_3$) δ 0.85 (distorted t, 3 H, $CH_3$), 1.05 (s, 18 H, $C(CH_3)_3$), 1.20–1.60 (m, 22 H, ($C\underline{H}_2)_{11}CH_3$), 2.70 (m, 2 H, =CH$C\underline{H}_2$—), 2.80 (br s, 2 H, H-4), 3.70 (AB q, J=10.7 Hz, 4 H, $CH_2OSi$), 6.10 (distorted t, 1 H, =CH—), 7.30–7.70 (m, 20 H, Ph); $^{13}C$ NMR δ 14.12, 19.22, 22.68, 26.68, 27.01, 29.18, 29.34, 29.51, 29.59, 29.66, 31.91, 33.15, 66.05, 84.37, 125.34, 127.75, 129.78, 132.70, 132.89, 135.57, 135.61, 143.35, 169.35. Anal. Calcd for $C_{52}H_{72}O_4Si_2$: C, 76.42; H, 8.89. Found: C, 76.38; H, 8.95. 11a: IR (neat) 1763.8 and 1681.9 $cm^{-1}$; $^1H$ NMR ($CDCl_3$) δ 0.85 (distorted t, 3 H, $CH_3$), 1.00 (s, 18 H, $C(CH_3)_3$), 1.30–1.50 (m, 22 H, ($C\underline{H}_2)_{11}CH_3$), 2.15 (m, 2 H, =CH$C\underline{H}_2$—), 2.75 (s, 2 H, H-4), 3.70 (AB q, J=10.7 Hz, 4 H, $CH_2OSi$), 6.70 (m, 1 H, =CH—), 7.30–7.60 (m, 20 H, Ph); $^{13}C$ NMR δ 14.12, 19.20, 22.68, 26.67, 28.14, 29.35, 29.41, 29.46, 29.53, 29.66, 30.18, 31.91, 66.16, 85.22, 127.47, 127.76, 129.81, 132.62, 132.87, 135.56, 135.61, 139.79, 170.60. Anal. Calcd for $C_{52}H_{72}O_4Si_2$: C, 76.42; H, 8.89. Found: C, 76.32; H, 8.96.

(Z)-5-bis-[(tert-Butyldiphenylsilyloxy)methyl]-3-[(Z)-9-octadecenoylidene]-tetrahydro-2-furanone (10b) and (E)-5-bis-[(tert-Butyldiphenylsilyloxy)methyl]-3-[(Z)-9-octadecenoylidene]-tetrahydro-2-furanone (11b). These compounds were obtained as oils in a similar fashion as 10a and 11a, starting from 3c and oleyl aldehyde. β-hydroxylactone intermediate: (74%), IR (neat) 3510.5, 1750.6, 1589.5 $cm^{-1}$; $^1H$ NMR ($CDCl_3$) δ 0.86 (distorted t, 3 H, $CH_3$),1.00 and 1.05 (singlets, 18 H, $C(CH_3)_3$), 1.20–1.50 (m, 24 H, CHOH($C\underline{H}_2)_6CH_2CH$=$CHCH_2(C\underline{H}_2)_6CH_3$), 1-90 (dd, J=12.6, 10.9 Hz, 1 H, H-$4_a$), 2.00 (m, 4 H, $C\underline{H}_2CH$=$CHC\underline{H}_2$), 2.20 (dd, J=12.6, 10.1 Hz, 1 H, H-$4_b$), 2.80 (m, 1 H, H-3), 3.50–3.80 (m, 4 H, $CH_2OSi$), 3.97 (s, 1 H, OH), 5.45 (m, 2 H, CH=CH), 7.30–7.60 (m, 20 H, Ph); $^{13}C$ NMR δ 14.10, 19.14, 19.20, 22.67, 24.88, 26.71, 26.75, 27.21, 28.97, 29.30, 29.51, 29.56, 29.60, 29.76, 31.88, 34.84, 45.87, 65.72, 66.38, 72.14, 86.82, 127.79, 127.88, 129.80, 129.89, 129.94, 129.98, 132.21, 132.51, 132.61, 132.65, 135.51, 135.55, 135.59, 179.54. Anal. Calcd for $C_{56}H_{80}O_5Si_2$: C,75.63; H, 9.07. Found: C, 75.37; H, 9.12.

10b: (32%); IR (neat) 1759.8 and 1670.5 $cm^{-1}$; $^1H$ NMR ($CDCl_3$) δ 0.86 (distorted t, 3 H, $CH_3$), 1.00 (s, 18 H, $C(CH_3)_3$), 1.20–1.50 (m, 22 H,$CH_2(C\underline{H}_2)_5CH_2CH$=$CHCH_2$—$(C\underline{H}_2)_6CH_3$), 2.00 (m, 4 H, $C\underline{H}_2CH$=$CHC\underline{H}_2$), 2.65 (m, 2 H, >C=CH$C\underline{H}_2$—), 2.80 (br s, 2 H, H-4), 3.70 (AB q, J=10.7 Hz, 4 H, $CH_2OSi$), 5.35 (m, 2 H, CH=CH), 6.10 (distorted t, 1 H, =CH—), 7.30–7.70 (m, 20 H, Ph); $^{13}C$ NMR δ 14.11, 19.21, 22.67, 26.68, 27.21, 27.59, 29.17, 29.23, 29.30, 29.41, 29.51, 29.76, 31.89, 33.15, 66.05, 84.37, 125.37, 127.74, 129.77, 129.82, 129.91, 132.69, 132.88, 135.56, 135.60, 143.27, 169.36. Anal. Calcd for $C_{56}H_{78}O_4Si_2$: C, 77.19; H, 9.03. Found: C, 77.01; H, 9.08.

11b: (60%); IR (neat) 1763.7 and 1683.9 $cm^{-1}$; $^1H$ NMR ($CDCl_3$) δ 0.90 (distorted t, 3 H, $CH_3$), 1.03 (s, 18 H, $C(CH_3)_3$), 1.20–1.50 (m, 22 H, $CH_2(C\underline{H}_2)_5CH_2CH$=$CHCH_2$—$(C\underline{H}_2)_6CH_3$), 2.00 (m, 4 H, $C\underline{H}_2CH$=$CHC\underline{H}_2$), 2.15 (m, 2 H, =CH$C\underline{H}_2$—), 2.75 (br s, 2 H, H-4), 3.70 (AB q, J=10.7 Hz, 4 H, $CH_2OSi$), 5.35 (m, 2 H, CH=CH), 6.70 (m, 1 H, =CH—), 7.30–7.65 (m, 20 H, Ph); $^{13}C$ NMR δ 14.13, 19.22, 22.69, 26.69, 27.19, 27.23, 28.16, 29.18, 29.33, 29.39, 29.53, 29.69, 29.76, 30.18, 31.91, 66.19, 85.23, 127.52, 127.78, 129.73, 129.83, 130.02, 132.62, 132.88, 135.58, 135.62, 139.72, 170.59. 8.96. Anal. Calcd for $C_{56}H_{78}O_4Si_2$: C, 77.19; H, 9.03. Found: C, 77.12; H, 9.06.

General desilylation procedure for the synthesis of 11c,d and 11c,d. A stirred solution of 10a,b/11a,b (0.28 mmol) in THF (8 mL) at room temperature was treated with a THF solution of tetrabutylammonium fluoride (1M, 0.85 mL) for the course of 1 h. After removing the volatiles under reduced pressure, the residue was partitioned between EtOAc (20 mL) and water (10 mL). The organic layer was separated and dried ($Na_2SO_4$). After evaporation of the solvent, the residue obtained was purified by flash column chromatography over silica gel using a 0% to 25% gradient of EtOAc in hexane as eluant. The compounds were isolated as colorless oils or solids:

(Z)-5-bis-(hydroxymethyl)-3-(tetradecanylidene)-tetrahydro-2-furanone (10c): solid (80% yield from 10a); mp 63°–64° C. (EtOAc/hexane); IR (KBr) 3316.0, 1750.4, and 1676 $cm^{-1}$; $^1H$ NMR ($CDCl_3$) δ 0.85 (distorted t, 3 H, $CH_3$), 1.10–1.50 (m, 22 H, ($C\underline{H}_2)_{11}CH_3$), 2.65 (m, 2 H, =CH$C\underline{H}_2$—), 2.75 (br s, 2 H, H-4), 3.00 (t, J=6.2 Hz, 2 H, OH, $D_2O$ exchangeable), 3.70 (m, 4 H, $C\underline{H}_2OH$), 6.20 (m, 1 H, =CH—); $^{13}C$ NMR δ 14.09, 22.67, 27.78, 29.05, 29.28, 29.33, 29.45, 29.56, 29.63, 29.66, 31.90, 32.66, 64.92, 84.49, 124.09, 145.84, 169.58. Anal. Calcd for $C_{20}H_{36}O_4$: C, 70.53; H, 10.66. Found: C, 70.42; H, 10.68.

(Z)-5-bis-(hydroxymethyl)-3-[(Z)-9-octadecenoylidene]-tetrahydro-2-furanone (10d): oil (81% yield from 10b); IR (neat) 3416.7, 1759.8, 1660.0 $cm^{-1}$; $^1H$ NMR ($CDCl_3$) δ0.86 (distorted t, 3 H, $CH_3$), 1.20–1.50 (m, 22 H, $CH_2(C\underline{H}_2)_5CH_2CH$=$CHCH_2(C\underline{H}_2)_6CH_3$), 2.00 (m, 4 H, $C\underline{H}_2CH$=$CHC\underline{H}_2$), 2.15 (t, J=6.5 Hz, 2 H, OH, $D_2O$ exchangeable), 2.68 (m, 2 H, >C=CH$C\underline{H}_2$—), 2.80 (br s, 2 H, H-4), 3.70 (m, 4 H, $C\underline{H}_2OH$), 5.35 (m, 2 H, CH=CH), 6.22 (m, 1 H, >C=CH—); $^{13}C$ NMR δ 14.09, 22.65, 27.19, 27.76, 29.04, 29.19, 29.25, 29.29, 29.35, 29.49, 29.63, 29.73, 31.87, 32.67, 64.82, 84.60, 124.16, 129.77, 129.94, 145.74, 169.71. Anal. Calcd for $C_{24}H_{42}O_4$: C,73.04; H, 10.73. Found: C, 72.93; H, 10.80.

(E)-5-bis-(hydroxymethyl)-3-(tetradecanylidene)-tetrahydro-2-furanone (11c): solid (80% yield from 11a); mp 76.5°–77.5° C. (EtOAc/hexane); IR (KBr) 3414.9, 1715.1, 1684.7 cm$^{-1}$; $^1$H NMR (CDCl$_3$) δ 0.86 (distorted t, 3 H, CH$_3$), 1.10–1.50 (m, 22 H, (CH$_2$)$_{11}$CH$_3$), 2.15 (m, 2 H, =CHCH$_2$—), 2.68 (br s, 2 H, H-4), 3.05 (br, 2 H, OH, D$_2$O exchangeable), 3.70 (AB q, J=12.1 Hz, 4 H, CH$_2$OH), 6.70 (m, 1 H, =CH—); $^{13}$C NMR δ 14.09, 22.66, 28.05, 29.34, 29.36, 29.38, 29.52, 29.62, 30.29, 31.89, 64.93, 85.55, 126.29, 142.20, 171.03. Anal. Calcd for $C_{20}H_{36}O_4$: C, 70.53; H, 10.66. Found: C, 70.47; H, 10.63.

(E)-5-bis-(hydroxymethyl)-3-[(Z)-9-octadecenoylidene]-tetrahydro-2-furanone (11d): oil (76% yield from 11b); IR (neat) 3411.7, 1714.1, 1683.8 cm$^{-1}$; $^1$H NMR (CDCl$_3$) δ 0.88 (distorted t, 3 H, CH$_3$), 1.20–1.50 (m, 22 H, CH$_2$(CH$_2$)$_5$CH$_2$CH=CHCH$_2$(CH$_2$)$_6$CH$_3$), 2.00 (m, 4 H, CH$_2$CH=CHCH$_2$), 2.15 (m, 2 H, >C=CHCH$_2$—), 2.70 (br s, 2 H, H-4), 2.85 (br s, 2 H, OH, D$_2$O exchanged), 3.70 (AB q, J=12.0 Hz, 4 H, CH$_2$OH), 5.35 (m, 2 H, CH=CH), 6.72 (m, 1 H, >C=CH—); $^{13}$C NMR δ 14.09, 22.65, 27.14, 27.20, 28.03, 29.14, 29.29, 29.34, 29.50, 29.69, 29.73, 30.27, 31.88, 65.05, 85.33, 126.23, 129.68, 130.01, 142.20, 170.78. Anal. Calcd for $C_{24}H_{42}O_4$: C,73.04; H, 10.73. Found: C, 72.89; H, 10.81.

General procedure for the monoacetylation of diols 10c,d and 11c,d. Syntheses of 10e,f and 11e,f. A stirred solution of diol 10c,d/11c,d (0.14 mmol), pyridine (0.7 mmol), and DMAP (1 mg) in dry CH$_2$Cl$_2$ (4 mL) at 0° C. was treated with acetic anhydride (0.14 mmol) for 1 h. The reaction was quenched by the addition of water (2 mL), and the layers were separated. The aqueous layer was extracted with CH$_2$Cl$_2$ (5 mL), and the combined organic extract was washed with 1N HCl (5 mL), water (5 mL), and dried (Na$_2$SO$_4$). The residue obtained after evaporation was purified by flash column chromatography over silica gel using 25–30% EtOAc in hexane. The compounds were isolated as colorless oils or solids:

rac-(Z)-5-(acetyloxymethyl)-5-(hydroxymethyl)-3-(tetradecanylidene)-tetrahydro-2-furanone (10e): solid (67% yield from 10c); mp 58.0°–59.0° C. (EtOAc/hexane); IR (KBr) 3387.1, 1728.0, 1676.1 cm$^{-1}$; $^1$H NMR (CDCl$_3$) δ 0.86 (distorted t, 3 H, CH$_3$), 1.20–1.50 (m, 22 H, (CH$_2$)$_{11}$CH$_3$), 2.05 (s, 3 H, CH$_3$CO), 2.34 (br s, 1 H, OH), 2.65 (m, 3 H, H-4$_a$, =CHCH$_2$—), 2.88 (m, 1 H, H-4$_b$), 3.62 (br AB q, J=12.1 Hz, 2 H, CH$_2$OH), 4.20 (AB q, J=11.8 Hz, 2 H, CH$_2$OAc), 6.20 (m, 1 H, =CH—); $^{13}$C NMR δ 14.09, 20.65, 22.65, 27.73, 29.05, 29.26, 29.32, 29.42, 29.53, 29.62, 29.64, 31.89, 33.05, 64.53, 65.28, 82.22, 123.58, 145.77, 168.65, 170.81; FAB MS (m/z, relative intensity) 383 (MH$^+$, 100). Anal. Calcd for $C_{22}H_{38}O_5$: C, 69.08; H, 10.01. Found: C, 68.92; H, 10.07.

rac-(Z)-5-(acetyloxymethyl)-5-(hydroxymethyl)-3-[(Z)-9-octadecenoylidene]-tetrahydro-2-furanone (10f): semi-solid gum (62% yield from 10d); IR (neat) 3433.0, 1747.6, 1650 cm$^{-1}$; $^1$H NMR (CDCl$_3$) δ 0.88 (distorted t, 3 H, CH$_3$), 1.20–1.50 (m, 22 H, CH$_2$(CH$_2$)$_5$CH$_2$CH=CHCH$_2$—(CH$_2$)$_6$CH$_3$), 2.00 (m, 4 H, CH$_2$CH=CHCH$_2$), 2.10 (s, 3 H, CH$_3$CO), 2.70 (m, 3 H, H-4$_a$, >C=CHCH$_2$—), 2.88 (m, 1 H, H-4$_b$), 3.62 (m, 2 H, CH$_2$OH), 4.20 (AB q, J=11.8 Hz, 2 H, CH$_2$OAc), 5.32 (m, 2 H, CH=CH), 6.22 (m, 1 H, >C=CH—); $^{13}$C NMR δ 14.09, 20.66, 22.66, 27.19, 27.72, 29.04, 29.18, 29.23, 29.30, 29.50, 29.71, 29.74, 31.88, 33.08, 64.56, 65.23, 82.11, 129.76, 129.96, 145.80, 168.50, 170.80; FAB MS (m/z, relative intensity) 437 (MH$^+$,36). Anal. Calcd for $C_{26}H_{44}O_5$: C,71.51; H,10.16. Found: C, 71.40; H, 10.20.

rac-(E)-5-(acetyloxymethyl)-5-(hydroxymethyl)-3-(tetradecanylidene)-tetrahydro-2-furanone (11e): solid (54% yield from 11c); mp 77°–78° C.; IR (KBr) 3384.8, 1733.2, 1680.1 cm$^{-1}$; $^1$H NMR (CDCl$_3$) δ 0.85 (distorted t, 3 H, CH$_3$), 1.20–1.50 (m, 22 H, (CH$_2$)$_{11}$CH$_3$), 2.05 (s, 3 H, CH$_3$CO), 2.15 (m, 2 H, =CHCH$_2$—), 2.40 (t, J=6.7 Hz, 1 H, OH), 2.60 (dd, J=17.1, 2.6 Hz, 1 H, H-4$_a$), 2.80 (dd, J=17.1, 2.8 Hz, H-4$_b$), 3.65 (m, 2 H, CH$_2$OH), 4.20 (AB q, J=11.8 Hz, 2 H, CH$_2$OAc), 6.72 (m, 1 H, =CH—); $^{13}$C NMR δ 14.09, 20.63, 22.66, 28.05, 29.32, 29.37, 29.50, 29.61, 29.79, 30.28, 31.89, 64.71, 65.43, 82.90, 125.64, 142.22, 169.89, 170.77; FAB MS (m/z, relative intensity) 383 (MH$^+$, 100). Anal. Calcd for $C_{22}H_{38}O_5$: C, 69.08; H, 10.01. Found: C, 69.00; H, 10.05.

rac-(E)-5-(acetyloxymethyl)5-(hydroxymethyl)-3-[(Z)-9-octadecenoylidene]-tetrahydro-2-furanone (11f): solid (62% yield from 11d); mp 45.6°–46.5° C.; IR (KBr) 3383.0, 1732.5, 1680.6 cm$^{-1}$; $^1$H NMR (CDCl$_3$) δ 0.85 (distorted t, 3 H, CH$_3$), 1.20–1.50 (m, 22 H, CH$_2$(CH$_2$)$_5$CH$_2$CH=CHCH$_2$—(CH$_2$)$_6$CH$_3$), 2.00 (m, 4 H, CH$_2$CH=CHCH$_2$), 2.10 (s, 3 H, CH$_3$CO), 2.15 (m, 2 H, >C=CHCH$_2$—), 2.35 (t, J=6.8 Hz, 1 H, OH), 2.62 (dd, J=17.1, 2.6 Hz, 1 H, H-4$_a$), 2.80 (dd, J=17.1, 2.8 Hz, 1 H, H-4$_b$), 3.61 (m, 2 H, CH$_2$OH), 4.26 (AB q, J=11.8 Hz, 2 H, CH$_2$OAc), 5.32 (m, 2 H, CH=CH), 6.75 (m, 1 H, >C=CH—); $^{13}$C NMR δ 14.09, 20.63, 22.65, 27.12, 27.19, 28.05, 29.13, 29.29, 29.49, 29.68, 29.73, 29.78, 30.27, 31.87, 64.70, 65.42, 82.89, 125.66, 129.64, 130.04, 142.17, 169.80, 170.77; FAB MS (m/z, relative intensity) 437 (MH$^+$, 68). Anal. Calcd for $C_{26}H_{44}O_5$: C,71.51; H,10.16. Found: C, 71.62; H, 10.13.

5-(acetyloxymethyl)-5-(hydroxymethyl)-3-(tetradecanyl)-tetrahydro-2-furanone (mixture of diastereoisomers, 12). A solution of 11e (0.006 g) in EtOAc (5 mL) was hydrogenated in the presence of 10% Pd/C (0.003 g) at 45 psi for 1.3 h. The reaction mixture was filtered through a small pad of silica gel, which was washed with additonal EtOAc (10 mL). The collected filtrate was concentrated under vacuum to give 12 as a white solid in nearly quantitative yield; mp 78.5°–81.1° C. (EtOAc/hexane); IR (KBr) 3415.9, 1741.7 cm$^{-1}$; FAB MS (m/z, relative intensity) 385 (MH$^+$, 100). Anal. Calcd for $C_{22}H_{40}O_5$: C, 68.70; H, 10.49. Found: C, 68.80; H, 10.53.

Example 4

This example describes the synthesis of the compound of formula:

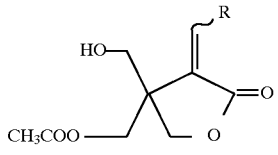

The above compound was synthesized according to the following reaction scheme (Scheme 4):

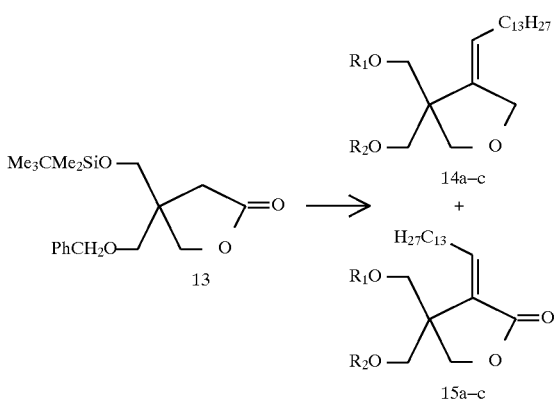

a, $R_1$=Me$_3$CMe$_2$Si, $R_2$=PhCH$_2$
b, $R_1$=CH$_3$CO, $R_2$=PhCH$_2$
c, $R_1$=CH$_3$CO, $R_2$=H

Lactone 13 was treated with the corresponding aldehyde (myristoyl or oleoyl aldehyde) to give around 70% of the intermediate alcohol, which was readily dehydrated to a separable mixture of the corresponding Z-(14a) and E-isomers (15a). Removal of the protective ether functions from these compounds, followed by formation of the corresponding monoacetates, gave the desired targets 14c and 15c.

4-[(Benzyloxy)methyl]-4-[(tert-butyldimethylsiloxy)methyl]-tetrahydro-2-furanone (13). A solution of 8b (1.28 g, 9.0 mmol) in THF (60 mL) was cooled to 0° C., treated with sodium hydride (60% dispersion in mineral oil, 0.72 g, 18 mmol), and stirred for 30 min. The reaction mixture was warmed to room temperature and benzyl bromide (1.6 mL, 13.5 mmol), followed by tetrabutylammonium iodide (0.33 g, 0.9 mmol), were added. The reaction mixture was stirred for 8 h at room temperature, cooled with an ice bath, and quenched with acetic acid (1 mL). The mixture was filtered through a short pad of silica gel, and the filtrate was concentrated. The residue was purified by flash column chromatography over silica gel with hexane:EtOAc (2:1) as eluant to give the corresponding benzyl ether (2.0 g, 96%) as an oil: IR (neat) 1780 (C=O) and 1641 cm$^{-1}$ (C=C); $^1$H NMR (CDCl$_3$) δ 2.49 (d of AB, J=17.3 Hz, 1 H, H-3$_a$), 2.65 (d of AB, J=17.3 Hz, 1 H, H-3$_b$), 3.42 (s, 2 H, CH$_2$OCH$_2$Ph), 4.14 (d of AB, J=9.05 Hz, 1 H, H-5$_a$), 4.32 (d of AB, J=9.05 Hz, 1 H, H-5$_b$), 4.54 (s, 2 H, CH$_2$O CH$_2$Ph), 5.16 (d, J=17.6 Hz, 1 H, CH=CHH), 5.22 (d, J=10.8 Hz, CH=CHH), 5.87 (dd, J=17.6, 10.9 Hz, 1 H, CH=CH$_2$), 7.20–7.40 (m, 5 H, Ph); $^{13}$C NMR (CDCl$_3$) δ 36.50, 46.55, 73.03, 73.35, 73.87, 115.71, 127.49, 127.79, 128.41, 137.45, 137.99, 175.91. Anal. Calcd for C$_{14}$H$_{16}$O$_3$: C, 72.39; H, 6.94. Found. C, 72.27; H, 6.91.

The above compound (2.0 g, 8.6 mmol) was dissolved in aqueous acetone (1:1, 80 mL) and treated with 4-methylmorpholine N-oxide (2.02 g, 17.22 mmol), sodium metaperiodate (3.68 g, 17.22 mmol) and osmium tetroxide (2.5 wt. % in t-butanol, 2.16 mL, 0.17 mmol). After stirring for 20 h at room temperature, the reaction mixture was quenched with a saturated sodium thiosulfate solution (40 mL), stirred for 10 min, and extracted with EtOAc. The organic layer was washed with water, dried (Na$_2$SO$_4$), and concentrated. The residue was purified by flash column chromatography over silica gel with EtOAc/hexane (2:1) as eluant to give the corresponding aldehyde (1.90 g, 94%) as an oil: IR (neat) 1781 and 1728 cm$^{-1}$ (C=O); $^1$H NMR (CDCl$_3$) δ 2.51 (d of AB, J=17.9 Hz, 1 H, H-3$_a$) 2.84 (d of AB, J=17.9 Hz, 1 H, H-3$_b$), 3.69 (AB m, 2 H, CH$_2$OCH$_2$Ph), 4.23 (d of AB, J=9.8 Hz, 1 H, H-5$_a$), 4.51 (d of AB, J=9.8 Hz, 1 H, H-5$_b$), 4.54 (s, 2 H, CH$_2$OCH$_2$Ph), 7.20–7.40 (m, 5 H, Ph), 9.67 (s, 1 H, CHO); $^{13}$C NMR (CDCl$_3$) δ 32.05, 54.75, 69.14, 69.95, 73.49, 127.62, 128.03, 128.47, 136.73, 174.08, 198.66, 198.82 Anal. Calcd for C$_{13}$H$_{14}$O$_4$: C, 66.65: H, 6.02. Found: C, 66.54; H, 6.07.

The above aldehyde (1.08 g, 4.6 mmol) was dissolved in aqueous THF (1:9, 100 mL) and cooled to −15° C. The solution was treated with sodium borohydride (0.348 g, 9.2 mmol) and stirred for 30 min. The reaction mixture was acidified with 1N HCl solution to pH 2–3, and concentrated to small volume. The mixture was diluted with water and extracted with ether. The organic layer was washed with water, dried (Na$_2$SO$_4$), and concentrated. The residue was purified by flash column chromatography over silica gel with EtOAc/hexane (3:2) as eluant to give the corresponding alcohol (1.07 g, 98%) as an oil: IR (neat) 3456 (OH), 1775 cm$^{-1}$ (C=O); $^1$H NMR (CDCl$_3$) δ 2.14 (bs, 1 H, OH), 2.45 (AB q, J=17.9 Hz, 2 H, H-5), 3.51 (s, 2 H, CH$_2$OH), 3.68 (AB m, 2 H, CH$_2$OCH$_2$Ph), 4.16 (d of AB, J=9.45 Hz, 1 H, H-5$_a$), 4.22 (d of AB, J=9.45 Hz, 1 H, H-5$_b$), 4.52 (s, 2 H, CH$_2$OCH$_2$Ph), 7.20–7.40 (m, 5 H, Ph); $^{13}$C NMR (CDCl$_3$) δ 34.23, 45.54, 64.96, 72.17, 72.37, 73.48, 127.57, 127.94, 128.49, 137.29, 176.69. Anal. Calcd for C$_{13}$H$_{16}$O$_4$: C, 66.08; H, 6.83. Found. C, 65.85; H, 6.84.

The above alcohol (1.07 g, 4.5 mmol) was dissolved in DMF (20 ml) and treated with tert-butyldimethylsilyl chloride (1.02 g, 6.75 mmol) and imidazole (1.225 g, 18 mmol). The reaction mixture was stirred for 14 h and then diluted with water. The aqueous phase was extracted with CH$_2$Cl$_2$, and the organic layer was washed with water and brine. The organic phase was then dried (Na$_2$SO$_4$) and concentrated. The residue was purified by flash column chromatography over silica gel with hexane:EtOAc (5:1) as eluant to give 13 (1.51 g, 96%) as an oil: IR (neat) 1781 cm$^{-1}$ (C=O); $^1$H NMR (CDCl$_3$) δ 0.03 (s, 6 H, Si(CH$_3$)$_2$), 0.85 (s, 9 H, C(CH$_3$)$_3$), 2.44 (s, 2 H, H-3), 3.41 (s, 2 H, CH$_2$OSi), 3.57 (s, 2 H, CH$_2$OCH$_2$Ph), 4.13 (s, 2 H, H-5), 4.49 (s, 2 H, CH$_2$OCH$_2$Ph), 7.20–7.40 (m, 5 H, Ph); $^{13}$C NMR (CDCl$_3$) δ −5.66, 18.09, 25.68, 34.05, 46.07, 64.35, 71.08, 72.32, 73.42, 127.55, 127.80, 128.43, 137.60, 176.56. Anal. Calcd for C$_{19}$H$_{30}$O$_4$Si: C, 65.10; H, 8.63. Found: C, 64.97; H, 8.63.

(Z)-4-[(Benzyloxy)methyl]-4-[(tert-butyldimethylsiloxy)methyl]-3-(tetradecanylidene)-tetrahydro-2-furanone (14a) and (E)-4-[(Benzyloxy)methyl]-4-[(tert-butyldimethylsiloxy)methyl]-3-(tetradecanylidene)-tetrahydro-2-furanone (15a). A solution of 13 (1.563 g, 4.46 mmol) in THF (9 mL) was cooled to −78° C., treated with sodium bis(trimethylsilyl)amide (1.0M in tetrahydrofuran, 5.35 mL, 5.35 mmol) and stirred for 1 h. A mixture of tetradecyl aldehyde (80%, 1.42 g, 5.35 mmol) and hexamethylphosphoramide (0.96 g, 5.35 mmol) was added, and the reaction mixture was stirred at −78° C. for 1 h, and at −48° C. for another hour. The mixture was quenched with a saturated NH$_4$Cl solution and diluted with ether. The organic layer was washed with water, dried (Na$_2$SO$_4$), and concentrated. The residue was purified by flash column chromatography over silica gel with hexane:EtOAc (from 10:1 to 5:1) as eluant to give the β-hydroxy lactone intermediate. This compound was dissolved in CH$_2$Cl$_2$ (100 mL), cooled to 0° C., and stirred with triethylamine (3.0 mL, 21.5 mmol) and methanesulfonyl chloride (0.66 mL, 8.53 mmol) for 30 min. The reaction mixture was warmed to room temperature, stirred for 30 min extra, and additional triethylanine (12.0 mL, 86 mmol) was added. After stirring for 24 h at room temperature, the mixture was concentrated and diluted with ether. The ethereal solution was filtered and the filtrate was concentrated. The residue was purified by flash column chromatography over silica gel with hexane:EtOAc (19:1) as eluant to give the Z-isomer 14a (1.26 g, 52 t), as the first fraction, followed by the E-isomer 15a (0.63 g, 26%).

Compound 14a: oil; IR (neat) 1757 (C=O), 1658 cm$^{-1}$ (C=C); $^1$H NMR (CDCl$_3$) δ 0.01 (s, 6 H, Si(CH$_3$)$_2$), 0.85 (m, 12 H, C(CH$_3$)$_3$, (CH$_2$)$_{12}$CH$_3$), 1.10–1.50 (m, 22 H, >C=CHCH$_2$(CH$_2$)$_{11}$CH$_3$), 2.72 (m, 2 H, >C=CHCH$_2$), 3.41 (d of AB, J=8.8 Hz, CHHOSi), 3.49 (d of AB, J=8.85 Hz, CHHOSi), 3.60 (s, 2 H, CH$_2$OCH$_2$Ph), 4.13 (AB q, J=9.5 Hz, 2 H, H-5), 4.50 (AB q, J=12.2 Hz, 2 H, CH$_2$OCH$_2$Ph), 6.22 (t, J=7.6 Hz, 1 H, >C=CH), 7.20–7.40 (m, 5 H, Ph); $^{13}$C NMR (CDCl$_3$) δ −5.65, −5.57, 14.11, 18.15, 22.67, 25.74, 27.53, 29.16, 29.23, 29.34, 29.45, 29.54, 29.64, 29.66, 31.90, 48.24, 65.04, 70.37, 71.62, 73.46, 127.24, 127.51, 127.71, 128.39, 137.85, 146.55, 170.28. Anal. Calcd for C$_{33}$H$_{56}$O$_4$Si: C, 72.74; H: 10.36. Found: C, 72.98; H, 10.41.

Compound 15a: oil; IR (neat) 1760 (C=O) and 1672 cm$^{-1}$ (C=C); $^1$H NMR (CDCl$_3$) δ 0.02 (s, 6 H, Si(CH$_3$)$_2$), 0.85 (m, 12 H, C(CH$_3$)$_3$, (CH$_2$)$_{12}$CH$_3$), 1.10–1.50 (m, 22 H, >C=CHCH$_2$(CH$_2$)$_{11}$CH$_3$), 2.25 (m, 2 H, >C=CHCH$_2$), 3.60 (AB q, J=8.8 Hz, CH$_2$OSi), 3.70 (d of AB, J=9.7 Hz, 1 H, CHHOCH$_2$Ph), 3.80 (d of AB, J=9.7 Hz, 1 H, CHHOCH$_2$Ph), 4.13 (AB q, J=9.4 Hz, 2 H, H-5), 4.50 (AB q, J=12.0 Hz, 2 H, CH$_2$OCH$_2$Ph), 6.83 (t, J=7.8 Hz, 1 H, >C=CH), 7.20–7.40 (m, 5 H, Ph); $^{13}$C NMR (CDCl$_3$) δ −5.62, −5.59, 14.11, 18.18, 22.67, 25.74, 28.93, 28.99, 29.35, 29.42, 29.53, 29.64, 31.90, 49.20, 64.65, 70.94, 71.03, 73.55, 127.47, 127.43, 127.79, 128.40, 137.62, 144.79, 171.85. Anal. Calcd for C$_{33}$H$_{56}$O$_4$Si: C, 72.74; H: 10.36. Found: C, 72.77; H, 10.38.

(Z)-4-[(acetoxy)methyl]-4-[(Benzyloxy)methyl]-3-(tetradecanylidene)-tetrahydro-2-furanone (14$_b$). A solution of 14a (0.80 g, 1.47 mmol) in THF (20 mL) was cooled to 0° C., treated dropwise with tetrabutylammonium fluoride (1.0M, 3.0 mL, 3 mmol), and stirred for 30 min. The reaction mixture was diluted with ether and the organic phase was washed with water. The organic layer was dried (Na$_2$SO$_4$) and concentrated. The residue was purified by flash chromatography over silica gel with hexane:EtOA (2:1) as eluant to give the intermediate alcohol (0.63 g, 99.6%) as an oil: IR (neat) 3447 (OH), 1754 (C=O) and 1662 cm$^{-1}$ (C=C); $^1$H NMR (CDCl$_3$) δ 0.86 (distorted t, 3 H, CH$_3$), 1.10–1.50 (m, 22 H, >C=CHCH$_2$(CH$_2$)$_{11}$CH$_3$), 2.10 (br s, OH), 2.70 (m, 2 H, >C=CHCH$_2$), 3.51 (AB q, J=9.0 Hz, 2 H, CH$_2$OH), 3.64 (d of AB, J=11.0 Hz, 1 H, CHHOCH$_2$Ph), 3.574 (d of AB, J=11.0 Hz, 1 H, CHHOCH$_2$Ph), 4.18 (d of AB, J=9.5 Hz, H-5$_a$), 4.27 (d of AB, J=9.5 Hz, 1 H, H-5$_b$), 4.51 (AB q, J=12.1 Hz, 1 H, CH$_2$OCH$_2$Ph), 6.16 (t, J=7.6 Hz, 1 H, >C=CH), 7.20–7.40 (m, 5 H, Ph); $^{13}$C NMR (CDCl$_3$) δ 14.10, 22.67, 27.54, 29.09, 29.23, 29.34, 29.41, 29.53, 29.63, 29.65, 31.90, 47.98, 66.50, 70.44, 73.69, 73.91, 126.84, 127.63, 128.04, 128.57, 137.27, 146.65, 169.93. Anal. Calcd for C$_{27}$H$_{42}$O$_4$: C, 75.30; H, 10.06. Found. C, 75.06; H, 10.00.

This compound (0.63 g, 1.46 mmol) was dissolved in CH$_2$Cl$_2$ (30 mL) and treated with pyridine (0.5 mL, 6.2 mmol) and acetic anhydride (0.3 mL, 3.2 mmol). After stirring for 1 h at room temperature, the reaction mixture was concentrated and the residue was purified by flash column chromatography over silica gel with hexane:EtOAc (3:1) as eluant to give 14$_b$(0.684 g, 99%) as an oil: IR (neat) 1750 (C=O) and 1662 cm$^{-1}$(C=C); $^1$H NMR (CDCl$_3$) δ 0.86 (distorted t, 3 H, CH$_3$), 1.10–1.50 (m, 22 H, >C=CHCH$_2$(CH$_2$)$_{11}$CH$_3$), 1.99 (s, 3 H, CH$_3$CO), 2.72 (m, 2 H, >C=CHCH$_2$), 3.42 (s, 2 H, CH$_2$OCH$_2$Ph), 4.10–4.24 (m, 4 H, CH$_2$OAc, H-5), 4.51 (AB q, J=12.2 Hz, 2 H, CH$_2$OCH$_2$Ph), 6.22 (t, 1 H, J=7.6 Hz, 1 H, >C=CH), 7.20–7.40 (m, 5 H, Ph); $^{13}$C NMR (CDCl$_3$) δ 14.10, 20.64, 22.67, 27.47, 29.00, 29.16, 29.33, 29.40, 29.53, 29.62, 31.90, 46.51, 65.78, 70.15, 72.02, 73.45, 126.19, 127.57, 127.88, 128.45, 137.43, 147.23, 169.48, 170.51. Anal. Calcd for C$_{29}$H$_{44}$O$_5$: C, 73.69; H, 9.38. Found: C, 73.79; H, 9.39.

(E)-4-[(acetoxy)methyl]-4-[(Benzyloxy)methyl]-3-(tetradecanylidene)-tetrahydro-2-furanone (15b). Starting with 15a, the same procedure described for the synthesis of 14b afforded the corresponding intermediate alcohol in 99% yield: oil; IR (neat) 3446 (OH), 1757 (C=O) and 1676 (C=C) cm$^{-1}$; $^1$H NMR (CDCl$_3$) δ 0.86 (distorted t, 3 H, CH$_3$), 1.10–1.50 (m, 22 H, >C=CHCH$_2$(CH$_2$)$_{11}$CH$_3$), 2.23 (m, 2 H, >C=CHCH$_2$), 3.57 (d of AB, J=9.0 Hz, 1 H, CHHOH), 3.72 (d of AB, J=11.0 Hz, 1 H, CHHOCH$_2$Ph), 3.76 (d of AB, J=9.0 Hz, 1 H, CHHOH), 4.01 (d of AB, J=11.0 Hz, 1 H, CHHOCH$_2$Ph), 4.25 (d of AB, J=9.5 Hz, 1 H, H-5$_a$), 4.34 (d of AB, J=9.5 Hz, 1 H, H-5$_b$), 4.51 (AB q, J=11.9 Hz, 1 H, CH$_2$OCH$_2$Ph), 6.83 (t, J=8.0 Hz, 1 H, >C=CH), 7.20–7.40 (m, 5 H, Ph); $^{13}$C NMR (CDCl$_3$) δ 14.10, 22.67, 28.78, 29.00, 29.16, 29.34, 29.39, 29.50, 29.63, 31.90, 32.26, 32.31, 48.63, 50.55, 63.36, 65.82, 70.96, 72.94, 73.89, 127.68, 127.75, 128.15, 128.50, 128.60, 135.02, 145.45, 171.32. Anal Calcd for C$_{27}$H$_{42}$O$_4$: C, 75.30; H, 10.06. Found. C, 75.36; H, 9.98.

This compound was acetylated as described for the synthesis of 14$_b$ to afford the E-isomer 15b in 99% yield: oil; IR (neat) 1750 (C=O) and 1672 cm$^{-1}$ (C=C); $^1$H NMR (CDCl$_3$) δ 0.86 (distorted t, 3 H, CH$_3$), 1.10–1.50 (m, 22 H, >C=CHCH$_2$(CH$_2$)$_{11}$CH$_3$), 2.00 (s, 3 H, CH$_3$CO), 2.24 (m, 2 H, >C=CHCH$_2$), 3.53 (d of AB, J=9.0 Hz, 1H, CHHOCH$_2$Ph), 3.63 (d of AB, J=9.0 Hz, 1 H, CHHOCH$_2$Ph), 4.15 (d of AB, J=9.5 Hz, CHHOAc), 4.23 (d of AB, J=9.5 Hz, 1 H, CHHOAc), 4.30 (AB q, J=11.2 Hz, 2 H, H-5), 4.50 (AB q, J=12.0 Hz, CH$_2$O CH$_2$Ph), 6.88 (t, J=7.9 Hz, 1 H, >C=CH), 7.20–7.40 (m, 5 H, Ph); $^{13}$C NMR (CDCl$_3$) δ 14.10, 20.70, 22.67, 28.86, 29.17, 29.33, 29.36, 29.42, 29.51, 29.63, 31.90, 46.86, 65.26, 70.73, 71.18, 73.57, 126.20, 127.68, 127.97, 128.48, 137.23, 145.94, 170.57, 171.08. Anal. Calcd for C$_{29}$H$_{44}$O$_5$: C, 73.69; H, 9.38. Found: C, 73.69: H, 9.40.

(Z)-4-[(acetoxy)methyl]-4-hydroxymethyl-3-(tetradecanylidene)-tetrahydro-2-furanone (14c). A solution of 14b (0.324 g, 0.685 mmol) in CH$_2$Cl$_2$ (20 mL) was cooled to −78° C., treated with boron trichloride (1.0M in dichloromethane, 2.74 mL, 2.74 mmol), and stirred for 1 h at that temperature. The reaction mixture was quenched with saturated NaHCO$_3$ solution (3.0 mL), and immediately partitioned between chloroform and a pH 7 buffer solution. The organic layer was washed with water, dried (Na$_2$SO$_4$), and concentrated. The residue was purified by flash column chromatography over silica gel with EtOAc/hexane (1:1) as eluant to give 14c (0.252 g, 96%) as a white solid: mp 48° C.; IR (KBr) 3489 (OH), 1735 (C=O) and 1667 cm$^{-1}$ (C=C); $^1$H NMR (CDCl$_3$) δ 0.86 (distorted t, 3 H, CH$_3$), 1.10–1.50 (m, 22 H, >C=CHCH$_2$(CH$_2$)$_{11}$CH$_3$), 2.08 (s, 3 H, CH$_3$CO), 2.60–2.90 (m, 2 H, >C=CHCH$_2$), 3.59 (AB m, 2 H, CH$_2$OH), 4.18 (2 AB multiplets, 4 H, H-5, CH$_2$OAc), 6.28 (t, 1 H, J=7.6 Hz, 1 H, >C=CH); $^{13}$C NMR (CDCl$_3$) δ 14.11, 20.72, 22.68, 27.61, 29.06, 29.24, 29.35, 29.41, 29.55, 29.64, 31.91, 47.58, 64.42, 65.34, 69.86, 126.06, 147.72, 169.69, 171.19; FAB MS m/z 383 (MH$^+$, 100). Anal. Calcd for C$_{22}$H$_{38}$O$_5$: C, 69.07; H, 10.01. Found: C, 69.06; H: 10.03.

(Z)-4-[(acetoxy)methyl]-4-hydroxymethyl-3-(tetradecanylidene)-tetrahydro-2-furanone (15c). The identical deblocking procedure described for the preparation of 14c was applied to 15b to yield 15c in 96% yield: solid; mp 52° C.; IR (neat) 3545 (OH), 1757 and 1724 (C=O), and 1672 cm$^{-1}$ (C=C); $^1$H NMR (CDCl$_3$) δ 0.86 (distorted t, 3 H, CH$_3$), 1.10–1.50 (m, 22 H, >C=CHCH$_2$(CH$_2$)$_{11}$CH$_3$), 1.90 (br s, 1 H, OH), 2.07 (s, 3 H, CH$_3$CO), 2.32 (m, 2 H, >C=CHCH$_2$), 3.75 (d of AB, J=11.1 Hz, CHHOH), 3.82 (d of AB, J=11.1 Hz, 1H, CHHOH), 4.15 (d of AB, J=9.6 Hz, 1 H, H-5$_a$), 4.25 (d of AB, J=9.6 Hz, 1 H, H-5$_b$), 4.37 (AB q, J=11.3 Hz, 2 H, CH$_2$OAc), 6.94 (t, 1 H, J=7.9 Hz, 1 H, >C=CH); $^{13}$C NMR (CDCl$_3$) δ 14.10, 20.73, 22.67, 28.95, 29.01, 29.34, 29.44, 29.52, 29.63, 31.90, 48.16, 63.94, 65.03, 70.51, 126.18, 146.37, 170.97, 171.51; FAB MS m/z 383 (MH$^+$, 100). Anal. Calcd for C$_{22}$H$_{38}$O$_5$: C, 69.07; H, 10.01. Found: C, 69.23; H, 10.07.

Example 5

This example describes the affinity of compounds of Examples 1–4 for PK-C.

The affinity of compounds of Examples 1–4 for PK-C was analyzed essentially as described in Wang et al. (J. Med. Chem. 37: 1326 (1994)), except that the PK-C preparation used was the single recombinant isozyme PK-C α. This recombinant PK-C α was expressed in baculovirus and isolated as described by Kazanietz et al. (Mol. Pharmacol. 44: 298–307 (1993)).

The affinity of these ligands for PK-C was assessed in terms of their ability to displace bound [$^3$H-20]-phorbol-12,13-dibutyrate (PDBU) from a purified product containing the single isozyme PK-C α. The inhibition curves obtained for these ligands were of the type expected for competitive inhibition, and the ID$_{50}$ values were determined by least-square fit of the data points to a theoretical competition curve (Teng et al. (1992), supra). The K$_i$s for inhibition of binding were calculated from the ID$_{50}$ values and are listed in Table I.

TABLE I

Apparent K$_i$ (nM) Values for Ligands as Inhibitors of PDBU Binding to PK-C.

| Template I | | Template II | |
|---|---|---|---|
| Compound # | K$_i$ | Compound # | K$_i$ |
| 3e | 138 ± 24 | 9c | 9,810 ± 900 |
| 3f | 96 ± 7.45 | 14c | 6,510 ± 450 |
| 10e | 35 ± 1.27 | 15c | 6,500 ± 450 |
| 11e | 78 ± 4.67 | | |
| 10f | 24 ± 2.87 | | |
| 11f | 28 ± 2.19 | | |
| 12 | 75 ± 2.54 | | |

These results show that the compounds of template I have a much higher affinity for PK-C than the compounds of template II.

Example 6

This example describes the synthesis of the compound of formula:

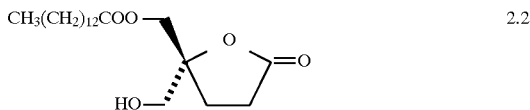

2.2

The above compound was synthesized according to the following reaction scheme (Scheme 5):

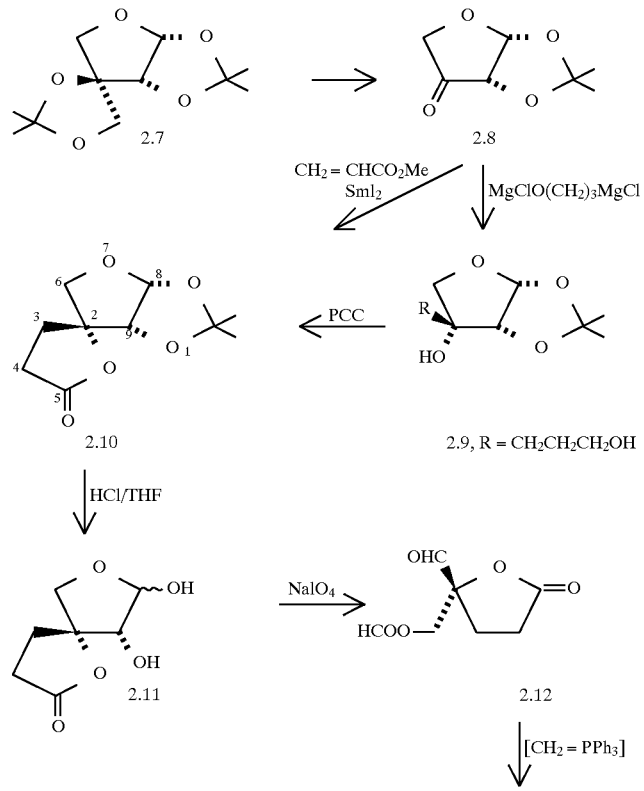

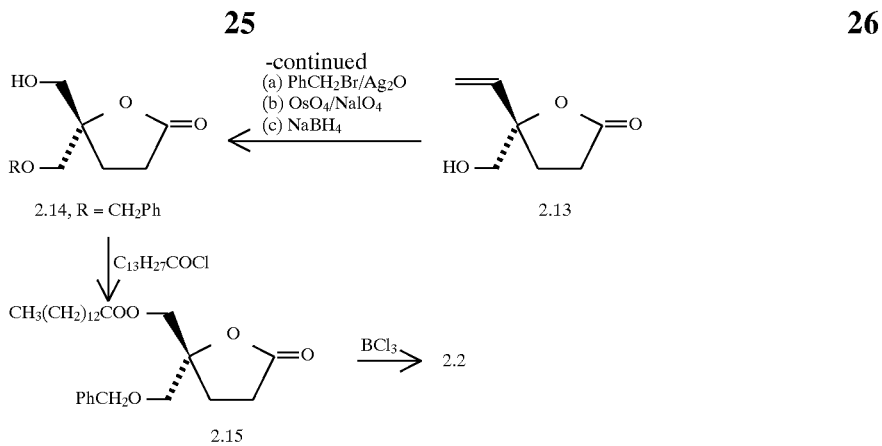

Commercially available 1,2:3,5-di-O-isopropylidene-α-D-threo-apiofuranose (2.7) was hydrolyzed under mild conditions to selectively remove the 3,5–O-isopropylidene group and the free diol was oxidized to the known keto intermediate 2.8 (Carey et al., Carbohydrate Res. 3:205 (1966)). Two spirolactonization approaches were attempted. The first one began with the addition of the Grignard reagent, MgClO(CH$_2$)$_3$MgCl, to give a new diol intermediate 2.9. This diol was oxidized with pyridinium chlorochromate (PCC), which, after the ensuing cyclization to the lactol, was further oxidized in situ to the spirolactone 2.10. Alternatively, and with the identical stereochemical outcome, a one-pot SmI$_2$-catalyzed reductive coupling of 2.8 with methyl acrylate produced 2.10 directly but in lower yield. Since only the convex face of 2.8 is accessible, the attacking reagents add stereospecifically from the less hindered β-side ensuring that the resulting spirolactone 2.10 contains the required stereochemistry for the construction of the target chiral template. Indeed, after removal of the acetonide group, metaperiodate cleavage of the vicinal diol group in 2.11 provided the required lactone 2.12. Wittig olefination of 2.12 with methyltriphenylphosphonium bromide proceeded with the simultaneous cleavage of the formate ester to give 2.13. Protection of the primary alcohol function as the benzyl ether, followed by the simultaneous treatment with OsO4 and sodium metaperiodate cleaved the cis-hydroxylated intermediate to the aldehyde stage. Sodium borohydride reduction of the aldehyde produced the chiral, singly protected lactone 2.14. This round-about approach was necessary, since direct reduction of aldehyde 2.12 would have given an achiral diol. Esterification with myristoyl chloride to the penultimate intermediate 2.15 and cleavage of the benzyl ether with BCl$_3$ at −78° C. was followed by a careful, low-temperature workup, that involved quenching the reaction mixture with a neutral buffer and extraction of the desired chiral lactone with ethyl ether. Exposure of compound 2.2 to chromatographic conditions, either over silica or neutral alumina, caused rapid racemization.

1,2-O-Isopropylidene-D-glycero-tetros-3-ulose (2.8). This compound was prepared from di-O-isopropylidene-α-D-apiose 2.7 in two steps according to the method of Carey et al. (1966), supra.

1,2-O-Isopropylidene-3-C-(hydroxypropyl)-a-D-erythrofuranose (2.9). A solution of 3-chloropropanol (2.84 g, 30 mmol) in THF (10 mL) was cooled to −20° C., treated dropwise with methylmagnesium chloride (3M in THF, 10 mL, 30 mmol), and stirred for 20 min. The reaction mixture was warmed to room temperature and magnesium (1.10 g, 45 mmol) was added. The suspension was refluxed for 3 h with the periodic addition of dibromoethane (0.02 mL each at 0, 1 and 2 h), and cooled to room temperature. A solution of 2.8 (1.58 g, 10 mmol) in THF (10 mL) was added dropwise to this mixture, and after stirring for 1 h, the reaction was cooled over an ice bath and quenched by the slow addition of a saturated NH$_4$Cl solution (20 mL). The reaction mixture was filtered, and the filtrate was extracted several times with EtOAc. The combined organic layer was dried (Na$_2$SO$_4$), and concentrated. The residue was purified by flash column chromatography over silica gel with EtOAc:hexanes (5:1) as eluant to give 2.9 (1.702 g, 78%) as a white solid; mp 95° C.; [α]$^{22}$D+28.46° (c 1.3, CHCl$_3$); IR (CHCl$_3$) 3433 cm$^{-1}$ (OH); $^1$H NMR (CDCl$_3$) δ 1.34 and 1.56 (singlets, 3 H, CH$_3$), 1.60–1.80 (m, 4 H, CH$_2$CH$_2$CH$_2$OH), 2.48 (br s, 2 H, OH), 3.60–3.76 (m, 4 H, CH$_2$OH, H-4), 4.14 (d, J=3.8 Hz, 1 H, H-2), 5.79 (d, J=3.8 Hz, 1 H, H-1); $^{13}$C NMR (CDCl$_3$) δ 26.32, 26.49, 26.53, 32.03, 62.44, 72.49, 78.20, 81.83, 105.10, 112.43. Anal. Calcd for C$_{10}$H$_{18}$O$_5$: C, 55.03; H, 8.31. Found: C, 55.14; H, 8.35.

(2R,8R,9R)-8,9-O-Isopropylidene-1,7-dioxaspiro-5-keto [4.4]nonane (2.10).

Method A A solution of 2.9 (1.702 g, 7.8 mmol) in CH$_2$Cl$_2$ (100 mL) was treated with pyridinium chlorochromate (6.725 g, 31.2 mmol) and 4 Å molecular sieves (7.8 g). After stirring for 1 h at room temperature, the reaction mixture was quenched with ether and celite, and stirred for 30 min. more. The suspension was filtered through a pad of silica gel and further washed with EtOAc. The filtrate was concentrated and the residue was purified by flash column chromatography over silica gel with EtOAc:hexanes (2:1) as eluant to give 2.10 (1.654 g, 99%) as a white solid; mp 102° C.; [α]$^{22}$$_D$ +74.00 ° (c 1.0, CHCl$_3$); IR (CHCl$_3$) 1785 cm$^{-1}$(C═O); $^1$H NMR (CDCl$_3$) δ 1.34 and 1.59 (singlets, 3 H, CH$_3$), 2.07–2.33 (m, 2 H, H-3), 2.64 (t, J=8.3 Hz, 2 H, H-4), 3.70 (d of AB, J=8.5 Hz, 1 H, H-6$_a$), 4.16 (d of AB, J=8.5 Hz, 1H, H-6$_b$), 4.33 (d, J=3.5 Hz, 1 H, H-9), 5.82 (d, J=3.5 Hz, 1 H, H-8); $^{13}$C NMR (CDCl$_3$) δ 26.51, 26.68, 27.47, 30.05, 70.49, 82.31, 86.71, 104.87, 114.23, 174.81. Anal. Calcd for C$_{10}$H$_{14}$O$_5$: C, 56.07; H, 6.59. Found: C, 56.14; H, 6.58.

Method B

A solution of 2.8 (0.316 g, 2 mmol) in THF (5 mL) was cooled to 0° C. and treated with a solution of methyl acrylate (0.36 mL, 4 mmol) in a mixture of 2-propanol (0.23 mL, 3 mmol) and hexamethylphosphoramide (2 mL). Samarium iodide (0.1M in THF, 60 mL, 6 mmol) was added dropwise to the reaction mixture, which was allowed to warm to room temperature. After stirring for 30 min, the mixture was quenched with ether (50 mL) and filtered through a pad of silica gel. The filtrate was concentrated and the residue was purified by flash column chromatography over silica gel with EtOAc/hexanes (2:1) as eluant to give 2.10 (124 mg, 30%) as a white solid.

(S)-5-Vinyl-5-hydroxymethyl-tetrahydro-2-furanone (2.13). A solution of 2.10 (0.857 g, 4 mmol) in THF (20 mL) was treated with 1N HCl solution (20 mL) and stirred for 20 h at room temperature. The reaction mixture was neutralized with solid NaHCO$_3$ and diluted with EtOAc. The mixture was dried and concentrated to give hemiacetal 2.11, which was used for the next step without further purification. This compound was dissolved in a mixture of MeOH (40 mL) and water (20 mL), and the solution was stirred with sodium metaperiodate (1.71 g, 8 mmol) for 2 h at room temperature. The reaction mixture was filtered and the filtrate was concentrated to dryness. The residue was dissolved in EtOAc, dried (Na$_2$SO$_4$), and concentrated to give aldehyde 2.12, which was used for the next step without further purification. Aldehyde 2.12 was dissolved in THF (10 mL) and the solution was slowly added to a suspension of methyl phosphonium ylide. This ylide was prepared from methyl triphenylphosphonium bromide (2.858 g, 8 mmol) and potassium t-butoxide (1.0M in THF, 8 mL, 8 mmol) in THF (10 mL) after stirring for 30 min at room temperature. The reaction mixture was stirred for 1 h at room temperature and for 1 h at 60° C. before it was cooled to 0° C. The reaction mixture was quenched with AcOH (0.5 mL), filtered, and the filtrate was concentrated. The residue was purified by flash column chromatography over silica gel with EtOAc:hexanes (4:1) as eluant to give 2.13 (0.387 g, 68% from 2.10) as an oil; IR (neat) 3440 (OH), 1770 (C=O) and 1644 cm$^{-1}$ (C=C); $^1$H NMR (CDCl$_3$) δ 2.05 (m, 1 H, H-4$_a$), 2.25 (s, 1 H, OH), 2.35–2.70 (m, 3 H, H-4$_b$, H-3), 3.54 (d of AB, J=12.3 Hz, 1 H, CHHOH), 3.75 (d of AB, J=12.3 Hz, 1 H, CHHOH), 5.26 (d, J=10.9 Hz, 1 H, CH=CHH), 5.37 (d, J=17.2 Hz, 1 H, CH=CHH), 5.83 (dd, J=17.2, 10.9 Hz, 1 H, CH=CH$_2$); $^{13}$C NMR (CDCl$_3$) δ 28.05, 28.79, 66.70, 88.37, 116.10, 136.46, 177.41. Anal. Calcd for C$_7$H$_{10}$O$_3$: C, 59.14; H, 7.09. Found: C, 59.15; H, 7.08.

(S)-5-[(Benzyloxy)methyl]-5-(hydroxymethyl)-tetrahydro-2-furanone (2.14). A solution of 2.13 (0.140 g, 1.0 mmol) in DMF (5 mL) was stirred with silver(I) oxide (0.232 g, 1.0 mmol) and benzyl bromide (0.3 mL, 2.5 mmol) for 5 days at room temperature. The reaction mixture was filtered, diluted with water, and extracted thrice with EtOAc. The organic layer was washed with water, dried (Na$_2$SO$_4$), and concentrated. The residue was purified by flash column chromatography over silica gel with hexanes:EtOAc (2:1) as eluant to give the intermediate 5-[(benzyloxy)methyl]-5-vinyl-tetrahydro-2-furanone (0.186 g, 80%) as an oil; [α]$^{22}_D$ −29.68° (c 3.08, CHCl$_3$); IR (neat) 1772 (C=O) and 1653 cm$^{-1}$ (C=C); $^1$H NMR (CDCl$_3$) δ 2.05 (m, 1 H, H-4$_a$), 2.35–2.74 (m, 3 H, H-4$_b$, H-3), 3.55 (AB q, J=10.4 Hz, 2 H, CH$_2$OH), 4.60 (AB q, J=12.0 Hz, 2 H, CH$_2$OCH$_2$Ph), 5.22 (dd, J=10.9, 0.5 Hz, 1 H, CH=CHH), 5.37 (dd, J=17.3, 0.6 Hz, 1 H, CH=CHH), 5.88 (dd, J=17.3, 10.9 Hz, 1 H, CH=CH$_2$); $^{13}$C NMR (CDCl$_3$) δ 28.88, 29.37, 73.66, 74.50, 86.81, 115.73, 127.58, 127.80, 128.46, 136.72, 137.65, 176.82. Anal. Calcd for C$_{14}$H$_{16}$O$_3$: C, 72.39; H, 6.94. Found: C, 72.62; H, 6.92.

The above compound (0.162 g, 0.7 mmol) was dissolved in aqueous acetone (1:1, 10 mL) and the solution was stirrerd with 4-methylmorpholine N-oxide (0.164 g, 1.4 mmol), sodium metaperiodate (0.300 g, 1.4 mmol), and osmium tetroxide (2.5 wt. % in t-butanol, 0.88 mL, 0.07 mmol) for 20 h at room temperature. The reaction mixture was quenched with saturated sodium thiosulfate solution (5 mL), stirred for 10 min, and extracted thrice with EtOAc. The combined organic layer was washed with water, dried (Na$_2$SO$_4$), and concentrated. The residue was purified by flash column chromatography over silica gel with EtOAc:hexane (4:1) as eluant to give the corresponding aldehyde (0.156 g, 96%) as an oil. This compound was immediately dissolved in MeOH (10 mL), cooled to −10° C., and treated with sodium borohydride (90 mg, 2.4 mmol). After stirring for 30 min, the reaction mixture was quenched with with 1N HCl and diluted with EtOAc. The organic layer was washed with water, dried (Na$_2$SO$_4$), and concentrated. The residue was purified by flash column chromatography over silica gel with EtOAc:hexane (from 3:1 to 6:1) as eluant to give 2.14 (0.110 g, 70%) as a white solid; mp 78° C.; [α]$^{22}_D$+7.73° (c 4.4, CHCl$_3$); IR (CHCl$_3$) 3446 (OH) and 1771 cm$^{-1}$ (C=O); $^1$H NMR (CDCl$_3$) δ 2.10–2.20 (m, 2 H, H-4), 2.50–2.75 (m, 2 H, H-3), 3.60 (AB q, J=10.1 Hz, 2 H, CH$_2$OH), 3.62 (d of AB, J=12.1 Hz, 1 H, CHHOCH$_2$Ph), 3.75 (d of AB, J=12.1 Hz, 1 H, CHHOCH$_2$Ph), 4.54 (br s, 2 H, CH$_2$OCH$_2$Ph), 7.20–7.40 (m, 5 H, Ph); $^{13}$C NMR (CDCl$_3$) δ 25.70, 29.15, 65.53, 72.43, 73.72, 87.46, 127.62, 127.90, 128.50, 137.49, 177.24. Anal. Calcd for C$_{13}$H$_{16}$O$_4$: C, 66.08; H, 6.83. Found: C, 66.00; H, 6.80.

(R)-5-[(Benzyloxy)methyl]-5-[(tetradecanoyloxy)methyl]-tetrahydro-2-furanone (2.15). A solution of 2.14 (0.024 g, 0.1 mmol) in CH$_2$Cl$_2$ (5 mL) was stirred with pyridine (0.032 mL, 0.4 mmol), a catalytic amount of dimethylaminopyridine, and tetradecanoyl chloride (0.054 mL, 0.2 mmol) for 2 h at room temperature. The solution was concentrated and the residue was purified by flash column chromatography over silica gel with hexane:EtOAc (2:1) as eluant to give 2.15 (0.041 g, 92%) as an oil; [α]$^{22}_D$+1.43° (c 4.2, CHCl$_3$); IR (neat) 1783 and 1743 cm$^{-1}$ (C=O); $^1$H NMR (CDCl$_3$) δ 0.85 (distorted triplet, 3 H, CH$_3$), 1.10–1.40 (m, 20 H, CH$_3$(CH$_2$)$_{10}$CH$_2$CH$_2$CO), 1.60 (br m, 2 H, CH$_3$(CH$_2$)$_{10}$CH$_2$CH$_2$CO), 2.00–2.30 (m, 2 H, H-4), 2.30 (t, J=7.5 Hz, 2 H, CH$_3$(CH$_2$)$_{10}$CH$_2$CH$_2$CO), 2.50–2.75 (m, 2 H, H-3), 3.60 (br s, 2 H, CH$_2$OCH$_2$Ph), 4.20 (AB q, J=11.9 Hz, 2 H, CH$_2$OCO), 4.55 (br s, 2 H, CH$_2$OCH$_2$Ph), 7.20–7.40 (m, 5 H, Ph); $^{13}$C NMR (CDCl$_3$) δ 14.09, 22.65, 24.81, 26.40, 28.78, 29.07, 29.20, 29.32, 29.42, 29.57, 29.61, 29.64, 31.89, 34.03, 65.99, 72.21, 73.76, 84.94, 127.63, 127.93, 128.49, 137.33, 173.14, 176.30. Anal. Calcd for C$_{27}$H$_{42}$O$_5$: C, 72.61; H, 9.48. Found: C, 72.70; H, 9.50.

(R)-5-[(tetradecanoyloxy)methyl]-5-(hydroxymethyl)-tetrahydro-2-furanone (2.2). A solution of 2.15 (0.036 g, 0.08 mmol) in CH$_2$Cl$_2$ (4 mL) was cooled to −78° C., treated with boron trichloride (1.0M in dichloromethane, 0.24 mL, 0.24 mmol), and stirred at that temperature for 1.5 h. The reaction mixture was quenched by the slow addition of a saturated NaHCO$_3$ solution (0.3 mL) at −78° C., and immediately partitioned between ice-cold ether and a pH 7 buffer solution. The organic layer was washed five times with the pH 7 buffer solution, dried (Na$_2$SO$_4$), and concentrated to give a white solid. This solid was washed with cold hexane several times to give a pure sample of 2.2 (24 mg, 84%) as a solid; mp 65°–66° C.; [α]$^{22}_D$ +1.43° (c 4.2, CHCl$_3$). The IR, $^1$H NMR, and $^{13}$C NMR were identical to those reported for the racemate (3e, Example 1).

Example 7
This example describes the synthesis of compounds of formulas:
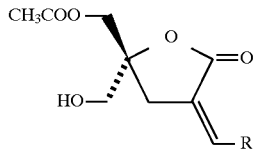
2.4
and
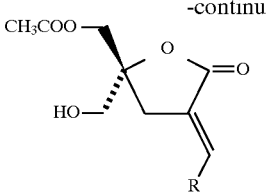
2.6
wherein R=(Z)—CH$_3$(CH$_2$)$_7$CH=CH(CH$_2$)$_7$.
The above compounds were synthesized according to the following reaction scheme (Scheme 6):
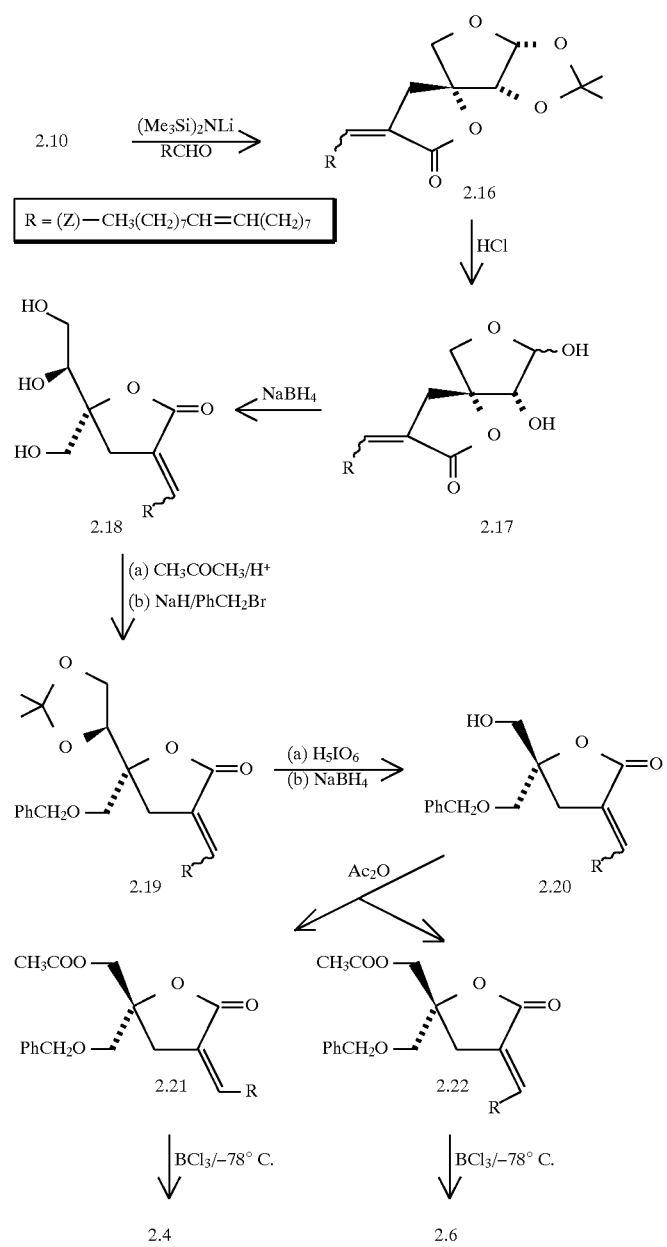

The more complex α-alkylidene lactones 2.4 and 2.6 were prepared from the pivotal intermediate spirolactone 2.10. In this instance, only the oleoyl aldehyde was used, which, after dehydration, gave compound 2.16 as a mixture of Z- and E-isomers. Removal of the isopropylidene function from 2.16 gave 2.17, and sodium borohydride reduction of the resulting lactol afforded the α-alkylidene lactone 2.18 with the desired chirality at C-4 (C-5, if named as a tetrahydro-2-furanone). The vicinal diol function on the side chain was protected as the acetonide, while the remaining primary alcohol function was converted into the more robust benzyl ether to give 2.19. Metaperiodic acid cleavage of 2.19, followed by reduction with sodium borohydride, gave the antepenultimate intermediate 2.20. After the conversion of 2.20 to a mixture of acetates, compounds 2.21 and 2.22 were separated by colum chromatography. As before, cleavage of the benzyl ether with $BCl_3$ at –78° C. was followed by a similar workup as described above. This approach produced the individual target Z- and E-isomers 2.4 and 2.6.

(R)-(Z)-5-(acetyloxymethyl)-5-(hydroxymethyl)-3-[(Z)-9-octadecenoylidene]-tetrahydro-2-furanone (2.4) and (R)-(E)-5-(acetyloxymethyl)-5-(hydroxymethyl)-3-[(Z)-9-octadecenoylidene]-tetrahydro-2-furanone (2.6). A stirred solution of 2.10 (0.428 g, 2.0 mmol) in THF (4 mL) was cooled to –78° C. and treated slowly with lithium bis(trimethylsilyl)amide (1.0M in THF, 2.4 mL, 2.4 mmol) for 1 h. A mixture of oleyl aldehyde (0.640 g, 2.4 mmol) and hexamethylphosphoramide (0.430 g, 5.35 mmol) was added and stirring was continued for 1 h at –78° C., and for 1 h at –40° C. The mixture was quenched with a solution of saturated ammonium chloride and diluted with ether. The organic layer was washed with water, dried ($Na_2SO_4$), and concentrated. The residue was purified by flash column chromatography over silica gel with hexanes:EtOAc (3:1) as eluant to give the intermediate β-hydroxy lactone (0.865 g, 90%). This compound was dissolved in $CH_2Cl_2$ (20 mL) and cooled to 0° C. The solution was then stirred with triethylamine (1.12 mL, 8 mmol) and methanesulfonyl chloride (0.31 ml, 4 mmol) for 30 min. The reaction mixture was warmed to room temperature, and stirred for 1 h before the addition of 1,8-diazabicyclo[5,4,0]undec-7-ene (1.5 mL, 10 mmol). After further stirring for 14 h at room temperature, the mixture was concentrated and diluted with ether. The ethereal solution was washed with diluted HCl, water and brine. The organic layer was dried ($Na_2SO_4$) and concentrated. The residue was purified by flash column chromatography over silica gel with hexanes:EtOAc (4:1) as eluant to give an inseparable mixture of E and Z-isomers (2.16, 0.800 g, 96%), as an oil, with a E/Z ratio of 2:1.

The above mixture 2.16 (0.463 mg, 1 mmol) was dissolved in THF (15 mL) and stirred in the presence of 2N HCl solution (15 mL) for 5 days at room temperature. The solution was then cooled with an ice bath and neutralized with solid $NaHCO_3$. The reaction mixture was filtered and the filtrate was concentrated. The residue was diluted with EtOAc, dried ($Na_2SO_4$), and concentrated to give hemiacetal 2.17 as an oil, which was used in the next step without further purification.

Hemiacetal 2.17 was dissolved in MeOH (10 mL), cooled to –10° C., and treated with small portions of sodium borohydride, which was until all the starting material was consumed. The reaction mixture was slowly acidified with acetic acid and concentrated. The residue was diluted with EtOAc and was washed with 1N HCl solution and water. The organic layer was dried ($Na_2SO_4$) and concentrated to give triol 2.18 as an oil, which also was used for the next step without further purification.

The above triol 2.18 was dissolved in acetone (20 mL) and cooled to 0° C. The solution was treated with a catalytic amount of p-toluenesulfonic acid and stirred for 1 h. It was then neutralized with solid $NaHCO_3$, filtered, and concentrated. The residue was purified by flash column chromatography over silica gel with hexanes:EtOAc (2:1) as eluant to give the corresponding mixture of E- and Z- acetonides (0.232 g, 50%) as an oil. The above mixture of acetonides (0.232 g, 0.5 mmol) was dissolved in THF (10 mL) and treated with sodium hydride (60% dispersion, 40 mg, 1 mmol) and a mixture of benzyl bromide (0.12 mL, 1 mmol) and tetrabutylammonium iodide (0.037 g, 0.1 mmol). The reaction mixture was stirred for 12 h at room temperature and quenched by the addition of acetic acid (0.1 mL) and ether. The suspension was filtered through a short pad of silica gel, which was washed with ether, and the filtrate was concentrated. The residue was purified by flash column chromatography over silica gel with hexanes:EtOAc (4:1) as eluant to give 2.19 (0.240 g, 86%) as oil.

The above mixture of E- and Z- isomers (compound 19, 0.239 g, 0.43 mmol) was dissolved in ether (30 mL) and treated with periodic acid (0.490 g, 2.15 mmol). The reaction mixture was stirred for 20 h at room temperature, filtered, and concentrated. The residue was purified by flash column chromatography over silica gel with hexanes:EtOAc (3:2) as eluant to give the corresponding mixture of E- and Z-aldehydes (0.200 mg, 96 %) as an oil. This mixture was immediately dissolved in THF (10 mL) and $H_2O$ (1 mL), cooled to –10° C. and treated with sodium borohydride portionwise until all the starting material was consumed. The reaction mixture was acidified by the slow addition of acetic acid and concentrated. The residue was diluted with ether and was washed with 1N HCl solution and water. The organic layer was dried ($Na_2SO_4$) and concentrated. The residue was purified by flash column chromatography over silica gel with hexanes:EtOAc (3:2) as eluant to give 2.20 (0.145 g, 72%) as an oil.

The above alcohol 2.20 (0.145 g, 0.3 mmol) was dissolved in $CH_2Cl_2$ (20 mL) and cooled to –10° C. and treated with pyridine (0.15 mL, 1.85 mmol), acetic anhydride (0.15 mL, 1.59 mmol), and a catalytic amount of dimethylaminopyridine. After stirring for 30 min, the reaction mixture was concentrated at 0° C. The residue was purified by flash column chromatography over silica gel with ether:hexanes (1:1) as eluant to give, respectively, the Z-isomer 2.21 (0.052 g, 33%) and the E-isomer 2.22 (0.103 g, 65%) as oils.

Z-isomer 2.21: $[\alpha]^{22}_D$ +1.43° (c 0.28, $CHCl_3$); IR (neat) 1752 and 1670 (C=O), and 1455 $cm^{-1}$; $^1H$ NMR ($CDCl_3$) δ 0.86 (distorted t, 3 H, $CH_3$), 1.00–1.50 (m, 22 H, $CH_2$(CH$_2$)$_5$CH$_2$CH=CHCH$_2$(CH$_2$)$_6$CH$_3$), 2.00 (m, 4 H, CH$_2$CH=CHCH$_2$), 2.02 (s, 3 H, $CH_3CO$), 2.60–2.90 (m, 4 H, >C=CHCH$_2$—, H-4), 3.49 (d of AB, J=9.9 Hz, 1 H, CHHOCH$_2$Ph), 3.57 (d of AB, J=9.9 Hz, CHHOCH$_2$Ph), 4.19 (s, 2 H, CH$_2$COCH$_3$), 4.54 (s, 2 H, $OCH_2Ph$), 5.33 (m, 2 H, CH$_2$CH=CHCH$_2$), 6.17 (m, 1 H, >C=CH), 7.20–7.40 (m, 5 H, Ph).

E-isomer 2.22: $[\alpha]^{22}_D$ −2.58° (c 0.62, CHCl$_3$); IR (neat) 1752 and 1684 (C=O), and 1456 cm$^{-1}$; $^1$H NMR (CDCl$_3$) δ 0.86 (distorted t, 3 H, CH$_3$), 1.10–1.50 (m, 22 H, CH$_2$(CH$_2$)$_5$CH$_2$CH=CHCH$_2$(CH$_2$)$_6$CH$_3$), 2.00 (m, 4 H, CH$_2$CH=CHCH$_2$) 2.01 (s, 3 H, CH$_3$CO), 2.15 (m, 2 H, >C=CHCH$_2$—), 2.62 (d of AB, J=17.0 Hz, 1 H, H-4$_a$), 2.82 (d of AB, J=17.0 Hz, 1 H, H-4$_b$), 3.50 (d of AB, J=9.9 Hz, 1 H, CHHOCH$_2$Ph), 3.58 (d of AB, J=9.9 Hz, CH HOCH$_2$Ph), 4.21 (s, 2 H, CH$_2$COCH$_3$), 4.55 (s, 2 H, OCH$_2$Ph), 5.33 (m, 2 H, CH$_2$CH=CHCH$_2$), 6.72 (m, 1 H, >C=CH), 7.20–7.40 (m, 5 H, Ph).

A solution of the Z-isomer (2.21) (0.103 g, 0.196 mmol) in CH$_2$Cl$_2$ (15 mL) was cooled to −78° C., treated with boron trichloride (1.0M in dichloromethane, 0.8 mL, 0.8 mmol), and stirred for 1.5 h. The reaction mixture was quenched by the slow addition of a saturated solution of NaHCO$_3$ (0.8 mL) and immediately partitioned between ice-cold ether and a pH 7 buffer solution. The organic layer was washed five times with the pH 7 buffer solution, dried (Na$_2$SO$_4$) and concentrated to give 2.4, which crytallized in cold hexane. The solid was filtered off and washed with cold hexane several times to give optically pure 2.4 (0.068 g, 80%); semisolid gum; $[\alpha]^{22}_D$+3.000 (c 0.3, CHCl$_3$). The IR, $^1$H NMR, and $^{13}$C NMR were identical to those reported for the racemate (10f, Example 3). The corresponding E-isomer 2.6 was also prepared by the same procedure in 80% yield; mp 46° C.; $[\alpha]^{22}_D$ +12.5° (c 0.24, CHCl$_3$). The IR, $^1$H NMR, and $^{13}$C NMR were identical to those reported for the racemate (11f, Example 3).

Example 8

This example compares the affinities of the chiral compounds of Examples 6 and 7 with the affinities of the racemates of Examples 1–4 for PK-C.

The affinities of the chiral compounds were determined as described in Example 5 and are presented in Table II.

Comparing the inhibition constant obtained for each enantiomer with that of the corresponding racemate reveals that the K$_i$ values for the active enantiomers are very close to half the values for the racemates. These results evidence the stereospecificity of PK-C for these lactones. These results also indicate that the ligands are interacting at the binding site of the enzyme where the key pharmacophores are spatially arranged in a manner similar to that encountered in the naturally bound DAG, but with a definitive entropic advantage.

Example 9

This example describes the synthesis of the compound of formula:

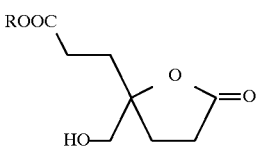

The above compound was synthesized according to the following reaction scheme (Scheme 7):

TABLE II

Apparent K$_i$ (nM) Values for Ligands as Inhibitors of PDBU Binding to PK-C.

| Racemic Compound | K$_i$ | Chiral Compound | K$_i$ |
|---|---|---|---|
| CH$_3$(CH$_2$)$_{12}$COO, HO — 2.1 | 138 ± 24 | CH$_3$(CH$_2$)$_{12}$COO, HO — 2.2 | 96 ± 2.17 |
| CH$_3$COO, HO — 2.3, R = (Z)—CH$_3$(CH$_2$)$_7$CH=CH(CH$_2$)$_7$ | 24 ± 2.87 | CH$_3$COO, HO — 2.4, R = (Z)—CH$_3$(CH$_2$)$_7$CH=CH(CH$_2$)$_7$ | 11 ± 0.30 |
| CH$_3$COO, HO — 2.5, R = (Z)—CH$_3$(CH$_2$)$_7$CH=CH(CH$_2$)$_7$ | 28 ± 2.19 | CH$_3$COO, HO — 2.6, R = (Z)—CH$_3$(CH$_2$)$_7$CH=CH(CH$_2$)$_7$ | 12 ± 1.26 |

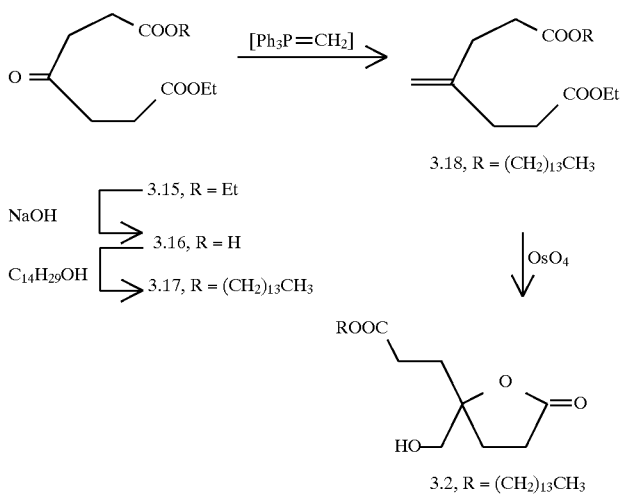

Partial hydrolysis of diethyl 4-oxopimelate (3.15) with NaOH gave the half-ester 3.16, which was condensed with myristyl alcohol to give the mixed diester 3.17. A Wittig olefination reaction of 3.15 with methyltriphenylphosphonium bromide/t-BuOK gave the expected olefin 3.18, which, after cis-hydroxylation with $OsO_4$, cyclized unidirectionally to the desired target lactone 3.2.

4-Oxo-heptadienoic acid, Monoethyl Ester (3.16). A stirred solution of diethyl 4-oxopimelate (4.81 g, 20.88 mmol) in 95% EtOH (100 mL) was treated with a solution of NaOH (0.835 g, 20.88 mmol) in water (30 mL) at room temperature. After stirring for 4 h, the reaction mixture was concentrared under suction, acidified to pH≈2 with 1N HCl, and extracted with EtOAc (3×30 mL). The combined organic extract was washed with water (2×50 mL), dried ($Na_2SO_4$), and concentrated. The oil obtained was purified by flash column Chromatography over silica gel using EtOAc:hexane(1:1) as eluant, which provided 1.35 g of starting material (3.15). Upon further elution with EtOAc, 3.16 was isolated as a white solid (1.44 g, 47%, based on recovered starting material); m.p. 69° C. (EtOAc/hexane); IR ($CH_2Cl_2$) 1731 (C=O) and 1704 (C=O) $cm^{-1}$; $^1H$ NMR ($CDCl_3$) δ 1.20 (t, J=7.1 Hz, 3 H, $CH_3$), 2.60 and 2.75 (multiples, 8 H, HOOC(C$\underline{H}_2$)$_2$CO(C$\underline{H}_2$)$_2$COOCH$_2$CH$_3$), 4.10 (q, J=7.1 Hz, 2 H, COOC$\underline{H}_2$CH$_3$); $^{13}C$ NMR ($CDCl_3$) δ 14.11, 27.65, 27.96, 36.80, 36.97, 37.05, 60.70, 172.71, 178.07, 206.80. Anal. Calcd for $C_9H_{14}O_5$: C, 53.44; H, 6.98. Found: C, 53.48; H, 7.01.

Tetradecyl Ethyl 4-Oxopimelate (3.17). A stirred solution of 3.16 (0.784 g, 3.88 mmol), 1-tetradecanol (1.00 g, 4.66 mmol) and DMAP (50 mg) in dry $CH_2Cl_2$ (25 mL) was kept under argon at room temperature and treated with dicyclohexylcarbodiimide (5.82 mL, 1M solution in $CH_2Cl_2$). After stirring for 24 h, the reaction mixture was quenched with a few drops of $CH_3COOH$ and MeOH, stirred for a few more minutes, and then concentrated under suction. The remainder was diluted with ether (50 mL), filtered and concentrated. The residue was purified by flash column chromatography over silica gel using a gradient of 3 to 12% EtOAc in hexane, to give 3.17 (0.304 g, 60%) as a colorless solid; mp 43° C. (EtOAc/hexane); IR (KBr) 1731 (C=O) and 1705 (C=O) $cm^{-1}$; $^1H$ NMR ($CDCl_3$) δ 0.85 (distorted t, 3H, C$\underline{H}_3$(CH$_2$)$_{13}$), 1.20–1.40 (m, 25 H, CH$_3$(C$\underline{H}_2$)$_{11}$CH$_2$CH$_2$OCO, C$\underline{H}_3$CH$_2$OCO), 1.55 (m, 2 H, CH$_3$(CH$_2$)$_{11}$C$\underline{H}_2$CH$_2$OCO), 2.55 (distorted t, 4 H, OCCH$_2$C$\underline{H}_2$CH$_2$COCH$_2$CH$_2$CO), 2.73 (distorted t, 4 H, OCCH$_2$C$\underline{H}_2$COCH$_2$CH$_2$CO), 3.95–4.10 (m, 4H, CH$_3$(CH$_2$)$_{11}$CH$_2$C$\underline{H}_2$OCO, CH$_3$C$\underline{H}_2$O); $^{13}C$ NMR ($CDCl_3$) δ 14.05, 14.10, 22.63, 25.83, 27.92, 28.53, 29.19, 29.30, 29.46, 29.52, 29.59, 31.87, 37.04, 60.55, 64.81, 172.61, 172.69, 206.92. Anal. Calcd for $C_{23}H_{42}O_5$: C, 69.31; H, 10.62. Found: C, 69.14; H, 10.65.

Tetradecyl 4-[(Ethoxycarbonyl)ethyl]-4-pentenoate (3.18). Potassium t-butoxide (0.195 g, 1.73 mmol) was added to a stirred suspension of methyl triphenylphosphonium bromide (0.618 g, 1.73 mmol) in dry benzene (8 mL), which was maintained under argon at room temperature. After stirring for 30 min, the reaction mixture was cooled to 0° C. and a solution of ketone 3.17 (0.46 g, 1.16 mmol) in dry THF was added rapidly. The reaction mixture was quenched after 30–60 minutes at 0° C. with brine (~10 mL), extracted with EtOAc (3×20 mL), and the combined organic layer was washed with water (1×10 mL) and dried ($Na_2SO_4$). The residue obtained after concentration was purified by flash column chromatography over silica gel using hexane:EtOAc (95:5) giving 3.18 as a liquid (0.72g, 71.5%); IR (neat) 1738 (C=O) and 1647 $cm^{-1}$; $^1H$ NMR ($CDCl_3$) δ 0.85(distorted t, 3H, C$\underline{H}_3$(CH$_2$)$_{13}$), 1.20–1.40 (m, 25 H, CH$_3$(C$\underline{H}_2$)$_{11}$CH$_2$CH$_2$OCO, C$\underline{H}_3$CH$_2$OCO), 1.60 (m, 2 H, CH$_3$(CH$_2$)$_{11}$C$\underline{H}_2$CH$_2$OCO), 2.35 (m, 4 H, OCCH$_2$C$\underline{H}_2$(C=CH$_2$)C$\underline{H}_2$CH$_2$CO), 2.45 (m, 4 H, OCC$\underline{H}_2$CH$_2$(C=CH$_2$)CH$_2$C$\underline{H}_2$CO), 4.00–4.15 (m, 4H, CH$_3$(CH$_2$)$_{11}$CH$_2$C$\underline{H}_2$OCO, CH$_3$C$\underline{H}_2$O), 4.75 (s, 2 H, =CH$_2$); $^{13}C$ NMR ($CDCl_3$) δ 14.09, 14.20, 22.66, 25.89, 28.60, 29.23, 29.33, 29.50, 29.56, 29.62, 31.00, 31.03, 31.89, 32.64, 60.35, 64.61, 109.75, 146.37, 173.08, 173.181. Anal. Calcd for $C_{24}H_{44}O_4$: C, 72.67; H, 11.19. Found: C, 72.63; H, 11.23.

(±)-5-Hydroxymethyl-5-[2-(tetradecyloxycarbonyl)ethyl] tetrahydro-2-furanone (3.2). A stirred solution of olefin 3.18 (0.115 g, 0.29 mmol) in t-BuOH (3 mL) and water (1 mL) at 0° C., containing N-methyl morpholine N-oxide (0.069 g, 0.59 mmol), was treated with 2.5% $OsO_4$ solution (0.16 mL). The reaction mixture was brought to room temperature slowly and stirred for 12 h; $Na_2SO_3$ (200 mg) was added and, after stirring for a few more minutes, it was concentrated under suction. The residue was extracted with EtOAc (3×10 mL) and the combined extract was washed with water (1×10 mL) and dried ($Na_2SO_4$). The residue obtained after evaporation of the solvent was purified by flash column chromatography over silica gel using hexane:EtOAc (3:2) as eluant to give 3.2 (0.070 g ,63%) as white solid; m.p. 61° C.

(EtOAc/hexane); IR (KBr) 3380 (OH) and 1728 (C=O) cm$^{-1}$; $^1$H NMR (CDCl$_3$) δ 0.85 (distorted t, 3H, CH$_3$(CH$_2$)$_{13}$), 1.10–1.40 (m, 22H, CH$_3$(CH$_2$)$_{11}$CH$_2$CH$_2$OCO), 1.60 (m, 2 H, CH$_3$(CH$_2$)$_{11}$CH$_2$CH$_2$OCO), 1.86–2.12 (m, 4 H, H-4, CH$_2$CH$_2$COOC$_{14}$H$_{29}$), 2.25–2.78 (multiplets, 4 H, H-3, CH$_2$CH$_2$COOC$_{14}$H$_{29}$), 2.90 (t, J=6.5 Hz, 1 H, OH), 3.50 (dd, J=12.1, 6.5 Hz, 1 H, CHHOH), 3.65 (dd, J=12.1, 6.5 Hz, 1 H, CHHOH), 4.05 (t, J=6.7 Hz, 2 H, CH$_3$(CH$_2$)$_{11}$CH$_2$CH$_2$OCO); $^{13}$C NMR (CDCl$_3$) δ 14.09, 22.65, 25.85, 28.05, 28.33, 28.51, 29.15, 29.21, 29.32, 29.48, 29.55, 29.61, 30.97, 31.88, 65.16, 66.41, 87.54, 173.28, 177.03; FAB MS m/z (relative intensity) 385 (38, MH$^+$), 171 (100, MH-C$_{14}$H$_{29}$OH). Anal. Calcd for C$_{22}$H$_{40}$O$_5$: C, 68.7; H, 10.49. Found: C, 68.63; H, 10.44.

Example 10

This example describes the synthesis of compounds of formula:

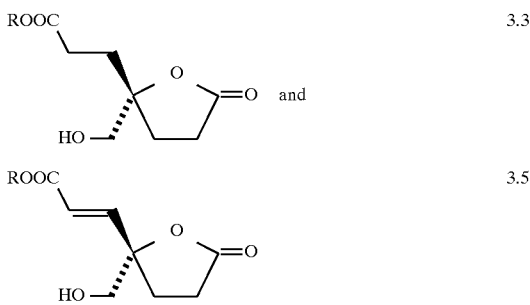

wherein R=CH$_3$ (CH$_2$)$_{13}$.

These compounds were synthesized according to the following reaction scheme (Scheme 8):

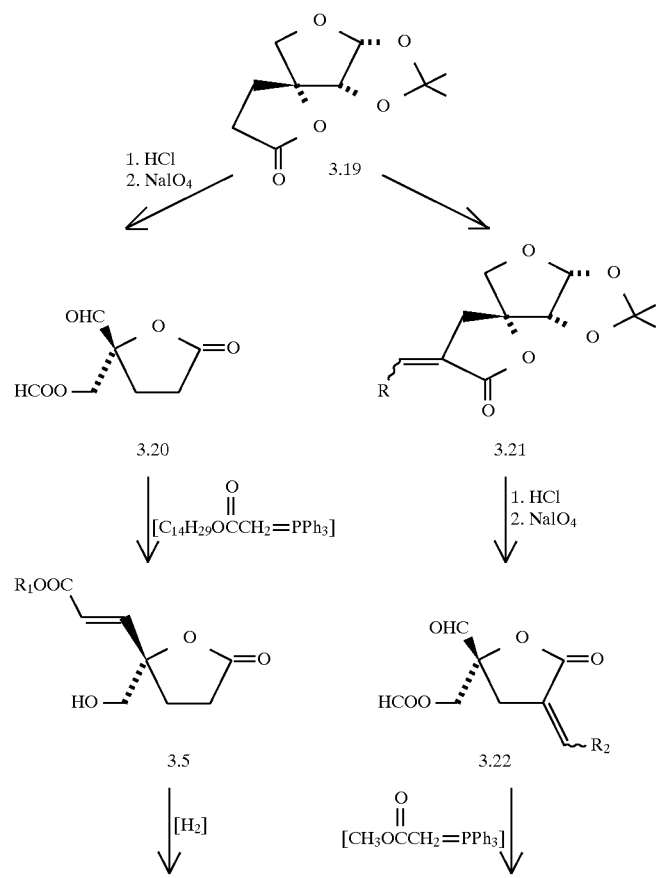

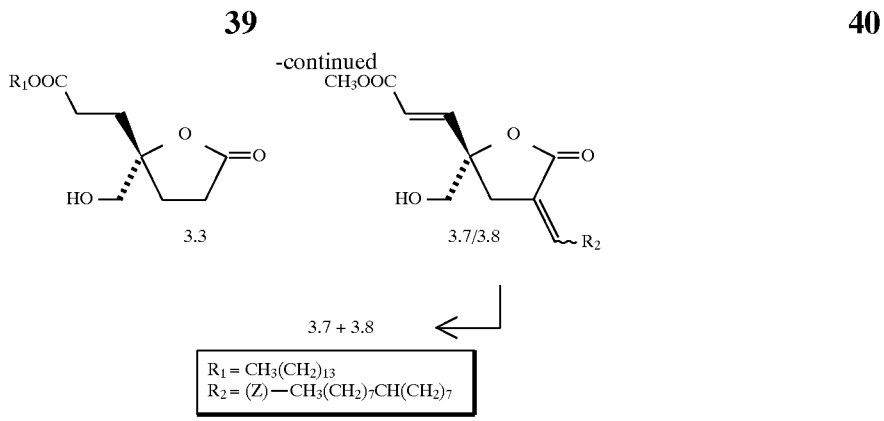

The enantioselective synthesis of lactones 3.3 and 3.5, which contain the active chiral template, started with the intermediate 3.19. Conversion of 3.19 to 3.20 was followed by a reaction of the resulting aldehyde with myristyl (triphenylphosphoranylidene)acetate to give the corresponding target α,β-unsaturated ester 3.5. This special Wittig reagent, myristyl (triphenylphosphoranylidene)-acetate, was prepared in three steps by (1) esterification of α-bromoacetic acid with tetradecanol, (2) subsequent reaction with triphenyl phosphine, and (3) treatment of the resulting phosphonium bromide with a $Na_2CO_3$ solution. This general methodology is similar to that published by Flock et al., Bull. Soc. Chim. Fr., 128: 1742 (1991). Catalytic hydrogenation of the double bond in 3.5 produced target 3.3.

(S)-5-Hydroxymethyl-5-[2-(tetradecyloxycarbonyl) ethenyl]tetrahydro-2-furanone (3.5). A solution of 3.19 (0.214 g, 1 mmol) in THF (5 mL) was treated with 1N HCl solution (5 mL) and stirred at room temperature for 20 h. The reaction mixture was neutralized with solid $NaHCO_3$ and diluted with EtOAc. The mixture was dried ($MgSO_4$) and concentrated to give the crude hemiacetal, which was used for the next step without further purification. This compound was dissolved in a mixture of MeOH (10 mL) and water (5 mL), and the solution was stirred with sodium metaperiodate (0.428 g, 2 mmol) for 2 h at room temperature. The reaction mixture was filtered and the filtrate was concentrated to dryness. The residue was dissolved in EtOAc, dried ($Na_2SO_4$) and concentrated to give aldehyde 3.20, which was used for the next step without further purification. Aldehyde 3.20 was dissolved in benzene (30 mL) and treated with tetradecanyl (triphenylphosphoranylidene)acetate (0.775 g, 1.5 mmol). The reaction mixture was refluxed for 2 h and concentrated. The residue was filtered through a short pad of silica gel, washed with ether, and the filtrate was concentrated to give a mixture of formate and free alcohol. The mixture was dissolved in methanol (10 mL), cooled to 0° C. and treated with ammonium hydroxide solution (0.1 mL) and stirred for 20 min. The reaction mixture was quenched with acetic acid (0.1 mL) and concentrated. The residue was purified by flash column chromatography over silica gel with EtOAc:hexanes (3:2) as eluant to give 3.5 (0.250 g, 65% from 3.19) as a white solid; mp 59° C.; $[α]^{22}_D$ -25.8° (c 1.0, $CHCl_3$); IR ($CHCl_3$) 3449 (OH), 1778 and 1752 cm$^{-1}$ (C=O); $^1H$ NMR ($CDCl_3$) δ 0.86 (distorted t, 3 H, C$\underline{H}_3$($CH_2$)$_{13}$), 1.10–1.40 (m, 22H, $CH_3$(C$\underline{H}_2$)$_{11}$$CH_2$$CH_2$OCO), 1.65 (m, 2 H, $CH_3$($CH_2$)$_{11}$C$\underline{H}_2$$CH_2$OCO), 2.08 (m, 2 H, H-$4_a$, OH), 2.42–2.74 (m, 3 H, H-$4_b$, H-3), 3.64 (dd, J=12.2, 7.1 Hz, 1 H, C$\underline{H}$HOH), 3.79 (dd, J=12.2, 5.3 Hz, 1 H, CH$\underline{H}$OH), 4.12 (t, J=6.7 Hz, 2 H, $CH_3$($CH_2$)$_{11}$$CH_2$C$\underline{H}_2$OCO), 6.13 (d, J=15.7 Hz, 1 H, C$\underline{H}$=CHCO), 6.85 (d, J=15.7 Hz, 1 H, CH=C$\underline{H}$CO); $^{13}$C NMR ($CDCl_3$) δ 14.09, 22.67, 25.88, 28.15, 28.40, 28.56, 29.23, 29.33, 29.49, 29.56, 29.63, 31.90, 65.16, 66.48, 86.98, 122.32, 144.47, 165.71, 176.11; FAB MS m/z (relative intensity) 383 (MH$^+$, 18), 169 (100, MH-$C_{14}H_{29}$). Anal. Calcd for $C_{22}H_{38}O_5$: C, 69.07; H, 10.01. Found: C, 69.15; H, 9.99.

(R)-5-Hydroxymethyl-5-[2-(tetradecyloxycarbonyl) ethyl]tetrahydro-2-furanone (3.3). A solution of 3.5 (0.154 g, 0.4 mmol) in EtOAc (20 mL) was treated with 10% Pd-C (0.4 g) and hydrogenated under a hydrogen balloon for 2 h. The reaction mixture was filtered and the filtrate was concentrated. The residue was purified by flash column chromatography over silica gel with EtOAc:hexanes (2:1) as eluant to give 3.3 (0.151 g, 98%) as a white solid; mp 59° C.; $[α]^{22}_D$ +7.90° (c 1.0, $CHCl_3$). The IR, $^1H$ NMR, and $^{13}$C NMR were identical to those reported for the racemate 3.2. Anal. Calcd for $C_{22}H_{40}O_5$: C, 68.71; H, 10.48. Found: C, 68.81; H, 10.45.

Example 11

This example describes the synthesis of compounds of formula:

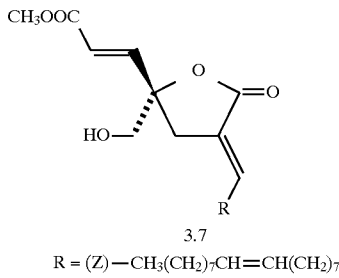

3.7
R = (Z)—$CH_3(CH_2)_7CH=CH(CH_2)_7$ and

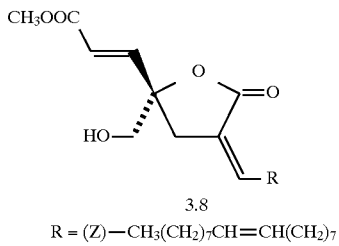

3.8
R = (Z)—$CH_3(CH_2)_7CH=CH(CH_2)_7$

These compounds were synthesized according to Scheme 8. The enantioselective synthesis of lactones 3.7 and 3.8, the two α-alkylidene compounds that contain the active chiral template, started with the intermediate 3.19. Compound 3.19 was reacted with oleoyl aldehyde to give a mixture of geometric isomers (3.21) after dehydration. A similar sequence of steps to those employed for the transformation of 3.19 to 3.20 was used to convert 3.21 into 3.22, which was isolated as a mixture of geometric isomers. Reaction of 3.22 with methyl (triphenylphosphoranylidene)acetate gave the corresponding final targets, which were chromatographically separated, respectively, as the E- (3.7) and Z- (3.8) isomers.

(S)-5-Hydroxymethyl-5-[2-(methoxycarbonyl)ethenyl]-3-{(E)-[(Z)-9-octadecenoylidene]}tetrahydro-2-furanone (3.7) and (S)-5-Hydroxymethyl-5-[2-(methoxycarbonyl)ethenyl]-3-{(Z)-[(Z)-9-octadecenoylidene]}tetrahydro-2-furanone (3.8). A solution of 3.21 (0.463 g, 1 mmol) in THF (15 mL) was treated with 2N HCl solution and stirred for 5 days at room temperature. The reaction mixture was then neutralized with solid $NaHCO_3$, while being chilled over ice, filtered, and concentrated. The residue was diluted with EtOAc, dried ($Na_2SO_4$), and concentrated to give the corresponding hemiacetal as an oil, which was used for the next step without further purification. This compound was dissolved in a mixture of MeOH (20 mL) and $H_2O$ (10 mL), and treated with sodium metaperiodate (0.428 g, 2 mmol). After stirring at room temperature for 4 h, the reaction mixture was filtered and concentrated. The residue was dissolved in ether, dried ($Na_2SO_4$), and concentrated to give aldehyde 3.22, which was used for the next step without further purification. Aldehyde 3.22 was dissolved in benzene (20 mL) and stirred with methyl (triphenylphosphoranylidene)acetate (0.067 g, 2.0 mmol) for 4 h. The solvent was evaporated, the residue was dissolved in ether and filtered through a short pad of silica gel with ether. The filtrate was concentrated to give a mixture of four products: the formates and free alcohols of both E/Z isomers. The mixture was dissolved in methanol (5 mL), cooled to 0° C., treated with ammonium hydroxide solution (0.05 mL), and stirred for 20 min. The reaction mixture was quenched with acetic acid (0.05 mL) and concentrated. The residue was purified by flash column chromatography over silica gel with hexanes:EtOAc (2:1) as eluant to give first the E-isomer (3.7), followed by the Z-isomer (3.8). The combined yield was 0.316 g (70.5% from 3.21).

E-isomer (3.7): white solid, mp 54° C.; $[\alpha]^{22}_D$ +20.32° (c 0.62, $CHCl_3$); IR ($CHCl_3$) 3447 (OH), 1755 and 1722 (C=O), and 1676 cm$^{-1}$ (C=C); $^1$H NMR ($CDCl_3$) δ 0.86 (distorted t, 3 H, C$\underline{H}_3$($CH_2$)$_7$CH=CH($CH_2$)$_7$CH=C<), 1.10–1.40 (m, 22 H, $CH_3$ (C$\underline{H}_2$)$_6$$CH_2$CH=CHCH$_2$ (C$\underline{H}_2$)$_5$$CH_2$$CH_2$CH=C<), 1.45 (m, 2 H, $CH_3$ ($CH_2$)$_6$CH$_2$CH=CHCH$_2$ ($CH_2$)$_5$C$\underline{H}_2$$CH_2$CH=C<), 2.00 (m, 4 H, $CH_3$($CH_2$)$_6$C$\underline{H}_2$CH=CHC$\underline{H}_2$ ($CH_2$)$_5$$CH_2$$CH_2$CH=C<), 2.15 (m, 2 H, $CH_3$ ($CH_2$)$_6$$CH_2$CH=CHCH$_2$($CH_2$)$_5$$CH_2$C$\underline{H}_2$CH=C<), 2.68 (dm, J=16.7 Hz, 1 H, H-4$_a$), 3.05 (dm, J=16.7 Hz, 1 H, H-4$_b$), 3.62 (AB d, J=12.0 Hz, 1 H, CH$\underline{H}$OH), 3.74 (s, 3 H, $CH_3$O), 3.78 (AB d, J=12.0 Hz, 1 H, C$\underline{H}$HOH), 5.33 (m, 2 H, $CH_3$($CH_2$)$_6$$CH_2$C$\underline{H}$=C$\underline{H}$$CH_2$($CH_2$)$_5$$CH_2$$CH_2$CH=C<), 6.13 (d, J=15.7 Hz, 1 H, $CH_3$OCOCH=C$\underline{H}$), 6.76 (m, 1 H, CH=C<), 6.89 (d, J=15.7 Hz, $CH_3$OCOC$\underline{H}$=CH); $^{13}$C NMR ($CDCl_3$) δ 14.07, 22.64, 27.12, 27.19, 28.00, 29.10, 29.25, 29.28, 29.48, 29.66, 29.72, 30.30, 31.87, 32.25, 32.56, 51.89, 66.65, 83.83, 121.75, 125.03, 129.66, 130.01, 142.68, 145.24, 166.14, 169.73; FAB MS m/z (relative intensity) 449 (MH$^+$, 26). Anal. Calcd for $C_{27}H_{44}O_5$: C, 72.28; H, 9.89. Found: C, 72.36; H, 9.95.

Z-isomer (3.8): oil; $[\alpha]^{22}_D$ −5.56° (c 0.36, $CHCl_3$); IR (neat) 3440 (OH), 1761 and 1729 (C=O), 1666 cm$^{-1}$ (C=C); $^1$H NMR ($CDCl_3$) δ 0.86 (distorted t, 3 H, C$\underline{H}_3$($CH_2$)$_7$CH=CH($CH_2$)$_7$CH=C<), 1.10–1.50 (m, 22 H, $CH_3$(C$\underline{H}_2$)$_6$$CH_2$CH=CHCH$_2$(C$\underline{H}_2$)$_5$$CH_2$CH=C<), 1.55 (br s, 1 H, OH), 2.00 (m, 4 H, $CH_3$($CH_2$)$_6$C$\underline{H}_2$CH=CHC$\underline{H}_2$($CH_2$)$_5$$CH_2$CH=C<), 2.6–2.78 (m, 3 H, $CH_3$($CH_2$)$_6$$CH_2$CH=CHCH$_2$($CH_2$)$_5$$CH_2$CH=C<, H-4$_a$), 3.12 (dm, J=16.0 Hz, 1 H, H-4$_b$), 3.55–3.80 (m, 5 H, $OCH_3$ and $CH_2$OH), 5.33 (m, 2 H, $CH_3$($CH_2$)$_6$$CH_2$C$\underline{H}$=C$\underline{H}$$CH_2$($CH_2$)$_5$$CH_2$$CH_2$CH=C<), 6.13 (d, J=15.6 Hz, 1 H, $CH_3$OCOCH=C$\underline{H}$), 6.22 (m, 1 H, CH=C<), 6.86 (d, J=15.7 Hz, $CH_3$OCOC$\underline{H}$=CH); $^{13}$C NMR ($CDCl_3$) δ 14.09, 22.66, 27.19, 27.79, 28.98, 29.18, 29.30, 29.40, 29.50, 29.72, 29.74, 31.88, 32.58, 35.51, 51.88, 66.48, 83.30, 121.83, 123.03, 129.77, 129.95, 145.34, 146.20, 166.17, 168.44; FAB MS m/z 449 (MH$^+$, 10). Anal. Calcd for $C_{27}H_{44}O_5$: C, 72.28; H, 9.89. Found: C, 71.99; H, 9.98.

Example 12

This example describes the synthesis of compounds of formulas:

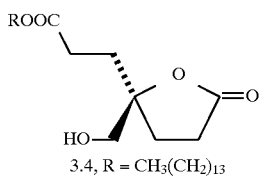

3.4, R = $CH_3(CH_2)_{13}$ and

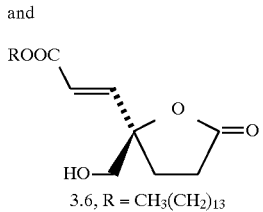

3.6, R = $CH_3(CH_2)_{13}$

These compounds were synthesized according to the following reaction scheme (Scheme 9):

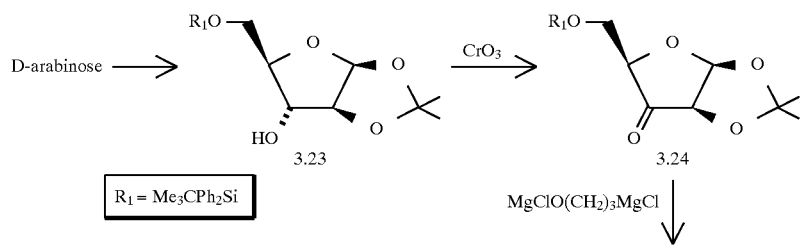

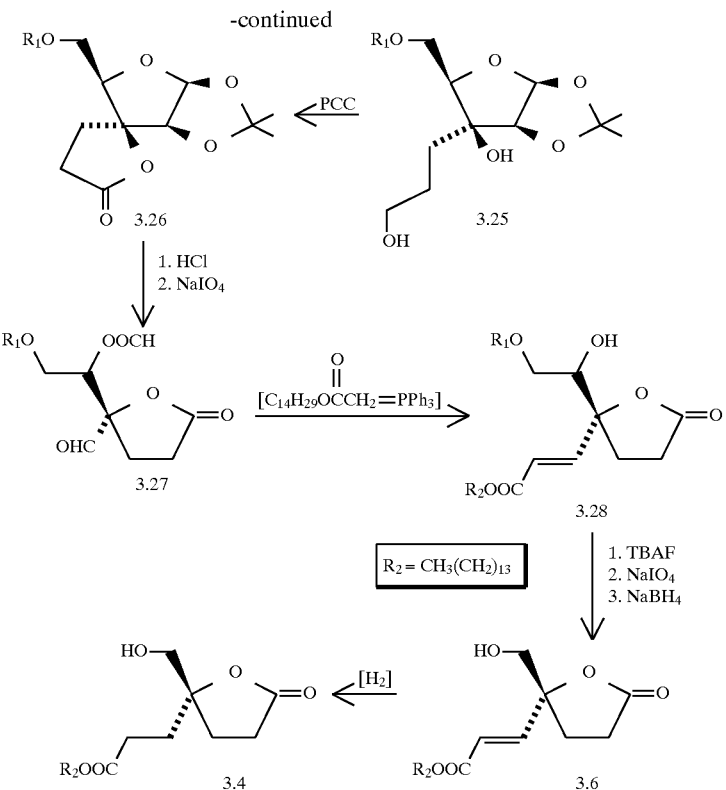

Compounds 3.4 and 3,6, which correspond to the optical antipodes of lactones 3.3 and 3.5, were synthesized to corroborate the identity of the active template. For this synthesis, a similar strategy to that used for the construction of chiral lactone 3.19 was performed from D-arabinose. Protection of this sugar as the 5-O-tert-butyldimethylsilyl-1,2-O-isopropylidene-β-D-arabinofuranose (3.23; Dahlman et al., Acta Chemica Scand B 40: 15 (1986)) was followed by chromium trioxide oxidation to the keto intermediate 3.24. Spirolactonization via the diol intermediate 3.25 was performed as before via PCC oxidation to give 3.26. In this instance, the addition of the Grignard reagent occurred stereospecifically from the less hindered α-side, thus ensuring the desired stereochemical outcome. As before, removal of the acetonide and metaperiodate cleavage of the resulting glycol moiety provided lactone 3.27. Wittig olefination of 3.27 with myristyl (triphenylphosphoranylidene) acetate gave the α,β-unsaturated ester 3.28, which required shortening of one of the branches by one carbon atom. This one-carbon shortening was accomplished after removal of the silyl ether protections by a second metaperiodate cleavage of the glycol moiety in 3.28, followed by sodium borohydride reduction to give the target compound 3.6. Catalytic hydrogenation of 3.6 provided the reduced target 3.4.

5-O-tert-Butyldiphenylsilyl-1,2-O-isopropylidene-β-D-threo-pentofuranose-3-ulose (3.24). This compound was prepared in three steps from D-arabinose by the method of Dahlman et al. (1986), supra.

5-O-tert-Butyldiphenylsilyl-3-C-(3-hydroxypropyl)-1,2-O-isopropylidene-β-D-lyxofuranose (3.25). A stirred solution of 3-chloropropanol (2.127 g, 22.5 mmol) in dry THF (20 mL) at −20° C. was treated dropwise with a solution of methylmagnesium chloride (3M in THF, 7.5 mL) and stirred for 20 min at that temperature. The reaction mixture was warmed to room temperature and magnesium (0.82 g, 33.8 mmol) was added. The reaction mixture was refluxed for 2 h with periodic addition of dibromomethane (0.025 mL each) at 0, 1, and 1.3 h intervals. After cooling to 0° C., a solution of ketone 3.24 (3.20 g, 7.5 mmol) in THF (25 mL) was added dropwise. The reaction was quenched after 1 h at 0° C. by the addition of saturated $NH_4Cl$ solution (25 mL). The layers were separated and the aqueous portion was extracted with EtOAc (2×25 mL). The combined organic layer was dried ($Na_2SO_4$) and concentrated. The residue obtained was purified by flash chromatography over silica gel using EtOAc/hexane (1:1) to give 3.25 as a liquid (3.0 g, 82%); $[\alpha]^D_{25}$=+15.16° (c 0.89, $CHCl_3$); IR (neat) 3499 cm$^{-1}$; $^1$H NMR ($CDCl_3$) δ 1.05 (s, 9H, C(C$\underline{H}_3$)$_3$), 1.30 and 1.40 (singlets, 3 H, $CH_3$), 1.50–1.80 (m, 4H, (C$\underline{H}_2$)$_2CH_2OH$), 2.5 (br s, 2H, OH), 3.60 (m, 2H, C$\underline{H}_2$OH),3.80–4.10 (m, 3 H, H-5$_a$, H-5$_b$, H-4), 4.20 (d, J=4.1 Hz, 1 H, H-2), 5.68 (d, J=4.1 Hz, 1 H, H-1), 7.60–7.80 (m, 4 H, Ph), 7.30–7.40 (m, 6 H, Ph); $^{13}$C NMR ($CDCl_3$) δ 19.13, 26.56, 26.67, 26.81, 26.89, 35.01, 62.74, 63.62, 78.04, 84.17, 85.30, 104.45, 113.91, 127.70, 129.70, 133.04, 133.27, 135.62, 135.68. Anal. Calcd for $C_{27}H_{38}O_6Si$: C, 66.63; H, 7.88. Found: C, 66.39; H, 7.84.

(2S,6R,8S,9S)-6-[(tert-Butyldiphenylsilyl-oxy) methyl]-8,9-O-Isopropylidene-1,7-dioxaspiro-5-keto [4.4]nonane (3.26). A stirred suspension of powdered molecular sieves (4 Å, 7.5 g) and 3.25 (3.67 g, 7.54 mmol) in anhydrous $CH_2Cl_2$ (100 mL) was treated with pyridinium chlorochromate (5.69 g,26.4 mmol) at room temperature. After stirring for 1 h, the reaction mixture was diluted with ether (200 mL) and filtered through a short pad of silica gel. The silica gel pad was washed with ether (ca. 100 mL) and the filtrate was concentrated and purified by flash chromatography over silica gel using hexane:EtOAc (7:3) to give 3.26 (3.12 g, 85.7%) as a solid; mp 123° C. (EtOAc/hexane); $[\alpha]^D_{25}$=−

9.72° (c 1.07, CHCl$_3$); IR (KBr) 1793 cm$^{-1}$; $^1$H NMR (CDCl$_3$) δ 1.02 (s, 9H, C(CH$_3$)$_3$), 1.30 and 1.48 (singlets, 3H, CH$_3$), 2.10–2.22 (m, 1 H, H-3$_a$), 2.30–2.70 (m, 3 H, H-3$_b$, H-4$_{a,b}$), 3.80–4.10 (m, 3 H, (CH$_3$)$_3$SiOCH$_2$, H-6), 4.48 (d, J=4.5 Hz, 1 H, H-9), 5.72 (d, J=4.5 Hz, 1 H, H-8), 7.30–7.50 (m, 6 H, Ph), 7.60–7.70 (m, 4 H, Ph); $^{13}$C NMR (CDCl$_3$) δ 19.08, 26.46, 26.77, 27.50, 27.75, 30.93, 62.20, 83.82, 86.17, 86.51, 104.12, 115.81, 127.77, 127.81, 129.81, 132.82, 132.89, 135.46, 135.53, 175.18. Anal. Calcd for C$_{27}$H$_{34}$O$_6$Si: C, 67.19; H, 7.1. Found: C, 67.07; H, 7.2.

(5R)-5-[(1R)-2-tert-Butyldiphenylsilyloxy-1-hydroxyethyl]-5-[2-(tetradecyloxycarbonyl)ethenyl]-tetrahydro-2-furanone (3.28). A solution of 3.26 (3.07g, 6.36 mmol) in THF (125 mL) was treated with a 1N HCl solution (57 mL) and stirred for 11 h at room temperature. The reaction mixture was neutralized by the careful addition of solid NaHCO$_3$, after which it was concentrated and extracted with EtOAc (3×40 mL). The combined organic extract was washed with water (2×50 mL) and dried (Na$_2$SO$_4$). The residue obtained after evaporation of the solvent was flash chromatographed over silica gel using EtOAc:hexane (3:2), giving the corresponding deprotected hemiacetal intermediate as a liquid (1.921 g, 68%). Anal. Calcd for C$_{24}$H$_{30}$O$_6$Si: C, 65.13; H, 6.84. Found: C, 65.00; H, 6.9. This hemiacetal intermediate (0.31g, 0.7 mmol) was dissolved in a mixture of MeOH (20 mL) and water (8 mL) and stirred with sodium metaperiodate (0.599 g, 2.8 mmol) at room temperature for 3.5 h. The reaction mixture was filtered, and the filtrate was concentrated. The residue was dissolved in EtOAc (30 mL), dried (Na$_2$SO$_4$), and concentrated to give the intermediate aldehyde 3.27, which was used for the next reaction without further purification. The above aldehyde was dissolved in benzene (15 mL) and stirred with tetradecanyl (triphenylphosphoranylidene) acetate (0.726 g, 1.4 mmol) for 18 h at room temperature. The reaction mixture was filtered through a short pad of silica gel and washed with ether (ca. 50 mL). The filtrate was concentrated, dissolved in MeOH (10 mL), and cooled to 0° C. The solution was stirred and treated with concentrated NH$_4$OH (0.1 mL) for 12 h. The reaction mixture was quenched with acetic acid (0.1 mL) and concentrated. The residue was purified by flash column chromatography over silica gel using a gradient of 20–40% EtOAc in hexane, to give 3.28 (0.359 g, 80.3%) as an oil; [α]$^D_{25}$=+2.25° (c 1.51, CHCl$_3$); IR (neat) 3473 (OH), 1786 and 1722 (C=O), and 1654 cm$^{-1}$; $^1$H NMR (CDCl$_3$) δ 0.88 (distorted t, 3H, CH$_3$(CH$_2$)$_{13}$), 1.02 (s, 9 H, C(CH$_3$)$_3$), 1.20–1.40 (m, 22H, CH$_3$(CH2)$_{11}$CH$_2$CH$_2$OCO), 1.60 (m, 2 H, CH$_3$(CH$_2$)$_{11}$CH$_2$CH$_2$OCO), 2.10–2.22 (m, 1 H, H-4$_a$), 2.40–2.60 (m, 3 H, H-4$_b$, H-3$_{a,b}$), 2.85 (br, 1H, OH), 3.62 (dd, J=11.7, 7.5 Hz, 1H, SiOCHHOCH(OH)), 3.78 (m, 2H, SiOCHHOCH(OH)), 4.08 (t, J=6.7 Hz, 2 H, CH$_3$(CH$_2$)$_{11}$CH$_2$CH$_2$OCO), 6.02 (d, J=15.8 Hz, 1 H, CH=CHCO), 7.00 (d, J=15.7 Hz, 1 H, CH=CHCO), 7.30–7.50 (m, 6H, Ph), 7.60–7.70 (m, 4H, Ph); $^{13}$C NMR (CDCl$_3$) δ 14.10, 19.14, 22.67, 25.88, 26.79, 27.51, 28.55, 29.25, 29.34, 29.40, 29.49, 29.58, 29.63, 29.67, 31.90, 63.44, 65.00, 75.08, 86.84, 121.43, 127.91, 130.03, 130.05, 132.38, 135.47, 144.16, 165.63, 175.71. Anal. Calcd for C$_{39}$H$_{58}$O$_6$Si: C, 71.96; H, 8.98. Found: C, 71.97; H, 9.05.

(R)-5-Hydroxymethyl-5-[2-(tetradecyloxycarbonyl)ethenyl]tetrahydro-2-furanone (3.6) and (R)-5-Hydroxymethyl-5-[2-(tetradecyloxycarbonyl)ethyl]tetrahydro-2-furanone (3.4). A stirred solution of 3.28 (0.25 g, 0.39 mmol) in THF (7 mL) at 0° C., was treated with HF-pyridine (1.5 mL). The reaction mixture was brought to room temperature during the course of 1 h and stirred further for 15 h. The reaction mixture was then diluted with a mixture of ice and ether and the layers were separated. The aqueous layer was extracted with ether (3×15 mL) and the combine extract was washed with water (2×10 mL) and dried (Na$_2$SO$_4$). The residue obtained after evaporation was purified by flash column chromatography over silica gel using a gradient from 60% to 100% EtOAc in hexane to give the intermediate, (5R)-5-[(1R)-1,2-hydroxyethyl]-5-[2-(tetradecyloxycarbonyl) ethenyl]-tetrahydro-2-furanone, as a white solid (0.115 g, 73%); mp 48° C. (EtOAc/hexane); [α]$^D_{25}$=+21.780° (c 1.01, CHCl$_3$); IR (CH$_2$Cl$_2$) 3453 (OH), 1779 and 1707 (CO), and 1654 cm$^{-1}$; $^1$H NMR (CDCl$_3$) δ 0.88 (distorted t, 3H, CH$_3$(CH$_2$)$_{13}$), 1.10–1.40 (m, 22H, CH$_3$(CH$_2$)$_{11}$CH$_2$CH$_2$OCO), 1.65 (m, 2 H, CH$_3$(CH$_2$)$_{11}$CH$_2$CH$_2$OCO), 2.00–2.22 (m, 1 H, H-4$_a$), 2.40–2.70 (m, 3 H, H-4$_b$, H-3$_{a,b}$), 3.60 (dd, J=11.2, 7.0 Hz, 1 H, CHHOCH(OH)), 3.72–3.90 (m, 2 H, CHHOCH(OH)), 4.10 (t, J=6.7 Hz, 2 H, CH$_3$(CH$_2$)$_{11}$CH$_2$CH$_2$OCO), 6.10 (d, J=15.7 Hz, 1 H, CH=CHCO), 6.95 (d, J=15.7 Hz, 1 H, CH=CHCO); $^{13}$C NMR (CDCl$_3$) δ 14.10, 22.67, 25.88, 27.70, 28.49, 28.53, 29.24, 29.33, 29.49, 29.57, 29.63, 31.90, 62.27, 65.23, 75.21, 87.26, 122.04, 144.12, 165.75, 175.88. Anal. Calcd for C$_{23}$H$_{40}$O$_6$: C, 66.94; H, 9.78. Found: C, 66.89; H, 9.73.

A stirred solution of this intermediate (0.112 g, 0.28 mmol) and NaHCO$_3$ (0.047 g, 0.56 mmol) in ethanol (5 mL) and water (2 mL) was treated with sodium metaperaiodate (0.180 g, 0.84 mmol) at room temperature for 3.5 h. The reaction mixture was cooled to 0° C. and treated with NaBH$_4$ (0.0 21 g, 0.56 mmol) with stirring for 1.5 h. The reaction mixture was then concentrated and extracted with EtOAc (3×20 mL). The combined organic extract was washed with water (2×10 mL) and dried (Na$_2$SO$_4$). The residue obtained after evaporation of the solvent was purified by flash column chromatography over silica gel using hexane:EtOAc (65:35) as eluant to give compound 3.6 (0.035 g, 34%), followed by 3.4 (0.024 g, 23%).

Compound 3.6: mp 60° C. (EtOAc/hexane); [α]$^D_{25}$=+24.560° (c 0.81, CHCl$_3$). All the spectral properties were identical to the optical antipode 3.5. Anal. Calcd for C$_{22}$H$_{38}$O$_5$: C, 69.08; H, 10.01. Found: C, 69.05; H, 9.95. Compound 3.4: mp 50° C. (EtOAc/hexane); [α]$^D_{25}$ -7.92° (c 1.06, CHCl$_3$). All the spectral properties were identical to the optical antipode 3.3 and the racemate 3.2. Anal. Calcd for C$_{22}$H$_{40}$O$_5$: C, 68.71; H, 10.48. Found: C, 68.58; H, 10.44.

Example 13

This example describes the synthesis of compounds of formulas:

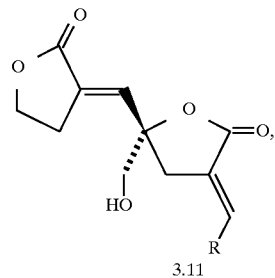

3.11

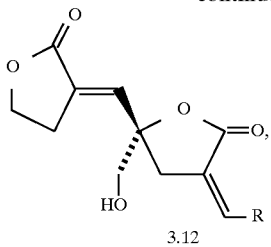

3.12

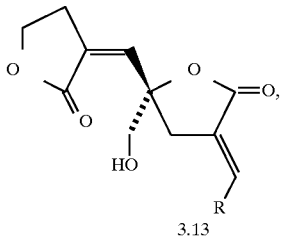

3.13 and

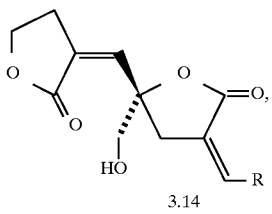

3.14 wherein R=(Z)—CH$_3$(CH$_2$)$_7$CH=CH(CH$_2$)$_7$.

These compounds were synthesized according to the following reaction scheme (Scheme 10):

The bis-γ-lactones 3.11–3.14 were synthesized by reacting aldehyde 3.22 with α-(triphenylphosphoranylidene)-γ-butyrolactone to give a mixture of all four isomers. Chromatographic separation of the isomers was possible after protection of the primary alcohol function as the tert-butyldimethylsilylether (compounds 3.29–3.32). Removal of the silyl ether group from each individual isomer privded the desired target compounds.

(S)-5-Hydroxymethyl-5-[(3,4-dihydro-2-(5H)-furanone-3-(E)-methyleneyl]-3-{(E)-[(Z)-9-octadecenoylidene]}tetrahydro-2-furanone (3.11), (S)-5-Hydroxymethyl-5-[(3,4-dihydro-2-(5H)-furanone-3-(E)-methyleneyl]-3-{(Z)-[(Z)-9-octadecenoylidene]}tetrahydro-2-furanone (3.12), (S)-5-Hydroxymethyl-5-[(3,4-dihydro-2-(5H)-furanone-3-(Z)-methyleneyl]-3-{(E)-[(Z)-9-octadecenoylidene]}tetrahydro-2-furanone (3.13), and (S)-5-Hydroxymethyl-5-[(3,4-dihydro-2-(5H)-furanone-3-(Z)-methyleney]-3-{(Z)-[(Z)-9-octadecenoylidene]}tetrahydro-2-furanone (3.14). Aldehyde 3.22 (1.0 mmol) was dissolved in benzene (20 mL) and dichlormethane (10 mL), and treated with α-triphenylphosphoranylidene)-γ-butyrolactone (0.070 g, 2.0 mmol). The reaction mixture was stirred for 14 h and concentrated. The residue was passed through a short pad of silica gel and eluted with ether. The filtrate was concentrated under reduced pressure to give a mixture of formates and free alcohols. The products were dissolved in methanol (5 mL), and the solution was cooled to 0° C. and treated with ammonium hydroxide solution (0.05 mL) with stirring for 10 min at 0° C. The reaction mixture was quenched with acetic acid (0.05 mL) and concentrated to give four products of different E/Z geometries (3.11–3.14) with very close R$_f$ values on TLC. The mixture of four products was dissolved in dichloromethane (40 mL), treated with tert-butyldimethylsilyl chloride (0.226 g, 1.5 mmol) and imidazole (0.272 g, 4.0 mmol), and stirred for 14 h. The

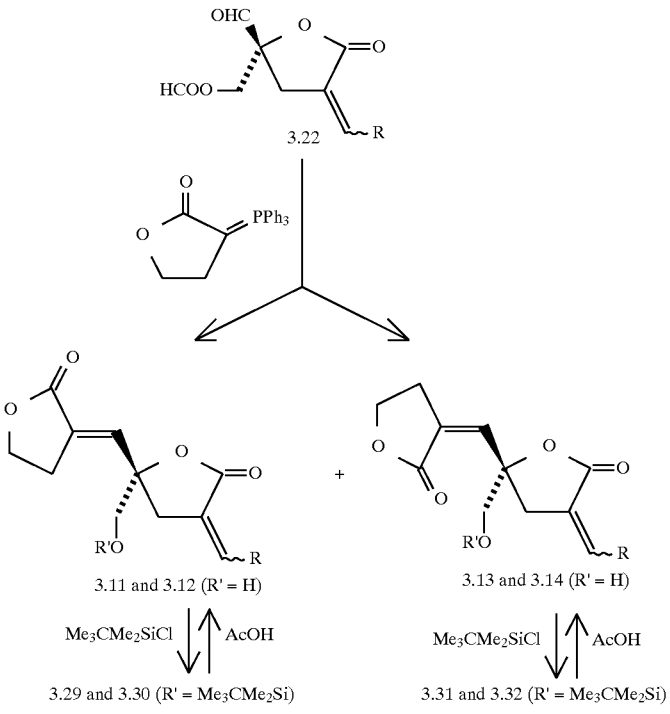

reaction mixture was concentrated and the residue was purified by flash column chromatography on silica gel with EtOAc:hexanes (5:1 to 3:1) as eluant. The order of elution of products was as follows: 3.30 (protected 3.12), 3.29 (protected 3.11), 3.32 (protected 3.14), and 3.31 (protected 3.13). Each isomer was dissolved in a mixture of acetic acid, water and THF (3:1:1) and heated to 60° C. for 48 h. The reaction mixture was concentrated and the residue was purified by flash column chromatography with EtOAc/hexanes (1:1) to give the final targets. The combined yield of products from 3.22 was 0.322 (70%).

Compound 3.12: oil; $[\alpha]^{22}_D$ −5.71° (c 0.14, CHCl$_3$); IR (neat) 3421 (OH), 1756 (C=O), 1670 cm$^{-1}$ (C=C); $^1$H NMR (CDCl$_3$) δ 0.86 (distorted t, 3 H, CH$_3$(CH$_2$)$_7$CH=CH(CH$_2$)$_7$CH=C<), 1.10–1.50 (m, 22 H, CH$_3$(CH$_2$)$_6$CH$_2$CH=CHCH$_2$(CH$_2$)$_5$CH$_2$CH=C<), 1.85 (br s, 1 H, OH), 2.00 (m, 4 H, CH$_3$(CH$_2$)$_6$CH$_2$CH=CHCH$_2$(CH$_2$)$_5$CH$_2$CH=C<), 2.60–2.85 (m, 3 H, CH$_3$(CH$_2$)$_6$CH$_2$CH=CHCH$_2$(CH$_2$)$_5$CH$_2$CH=C<, H-4$_a$), 3.00–3.30 (m, 3 H, H-4$_b$, H-4'$_{a,b}$), 3.70 (AB q, J=12.5 Hz, 2 H, CH$_2$OH), 4.36 (t, J=7.3 Hz, 2 H, H-5'$_{a,b}$), 5.32 (m, 2 H, CH$_3$(CH$_2$)$_6$CH$_2$CH=CH(CH$_2$)$_7$CH=C<), 6.26 (m, 1 H, C$_{17}$H$_{33}$CH=C<), 6.61 (t, J=2.9 Hz, 1 H, >C=CH—C); $^{13}$C NMR (CDCl$_3$) δ 14.09, 22.66, 25.86, 27.16, 27.19, 27.86, 28.95, 29.18, 29.22, 29.29, 29.40, 29.50, 29.70, 29.73, 31.88, 36.23, 65.95, 66.38, 83.95, 123.02, 128.11, 129.72, 129.98, 136.35, 146.44, 168.47, 171.2; FAB MS m/z (relative intensity) 461 (MH$^+$, 10). Anal. Calcd for C$_{28}$H$_{44}$O$_5$: C, 73.00; H, 9.63. Found: C, 72.83; H, 9.56.

Compound 3.11: oil; $[\alpha]^{22}_D$ +26.85° (c 0.54, CHCl$_3$); IR (neat) 3422 (OH), 1756 (C=O), 1680 cm$^{-1}$ (C=C); $^1$H NMR (CDCl$_3$) $^1$H NMR (CDCl$_3$) δ 0.86 (distorted t, 3 H, CH$_3$(CH$_2$)$_7$CH=CH(CH$_2$)$_7$CH=C<), 1.10–1.50 (m, 22 H, CH$_3$(CH$_2$)$_6$CH$_2$CH=CHCH$_2$(CH$_2$)$_5$CH$_2$CH=C<), 2.00 (m, 4 H, CH$_3$(CH$_2$)$_6$CH$_2$CH=CHCH$_2$(CH$_2$)$_5$CH$_2$CH=C<), 2.18 (m, 2 H, CH$_3$(CH$_2$)$_6$CH$_2$CH=CHCH$_2$(CH$_2$)$_5$CH$_2$CH=C<), 2.72 (dm, J=16.9 Hz, 1 H, H-4$_a$), 2.95–3.30 (m, 4 H, H-4$_{ab}$, H-4'$_{a,b}$), 3.73 (AB q, J=12.1 Hz, 2 H, CH$_2$OH), 4.35 (t, J=7.3 Hz, 2 H, H-5'$_{a,b}$), 5.32 (m, 2 H, CH$_3$(CH$_2$)$_6$CH$_2$CH=CH(CH$_2$)$_7$CH=C<), 6.64 (t, J=2.9 Hz, 1 H, >C=CH—C), 6.77 (m, 1 H, C$_{17}$H$_{33}$CH=C<); $^{13}$C NMR (CDCl$_3$) δ 14.03, 22.58, 25.79, 27.05, 27.12, 27.95, 29.05, 29.22, 29.25, 29.42, 29.60, 29.66, 30.33, 31.80, 32.87, 66.00, 66.42, 84.62, 125.09, 127.86, 129.57, 129.95, 136.42, 142.74, 169.91, 171.33; FAB MS m/z (relative intensity) 461 (MH$^+$, 19). Anal. Calcd for C$_{28}$H$_{44}$O$_5$: C, 73.00; H, 9.63. Found: C, 72.49; H, 9.58.

Compound 3.14: solid gum; $[\alpha]^{22}_D$ −30.000° (c 0.20, CHCl$_3$); IR (CHCl$_3$) 3423 (OH), 1753 and 1720 (C=O), 1675 cm$^{-1}$ (C=C); $^1$H NMR (CDCl$_3$) $^1$H NMR (CDCl$_3$) δ 0.86 (distorted t, 3 H, CH$_3$(CH$_2$)$_7$CH=CH(CH$_2$)$_7$CH=C<), 1.10–1.50 (m, 22 H, CH$_3$(CH$_2$)$_6$CH$_2$CH=CHCH$_2$(CH$_2$)$_5$CH$_2$CH=C<), 1.85 (br s, 1 H, OH), 2.00 (m, 4 H, CH$_3$(CH$_2$)$_6$CH$_2$CH=CHCH$_2$(CH$_2$)$_5$CH$_2$CH=C<), 2.65 (m, 2 H, CH$_3$(CH$_2$)$_6$CH$_2$CH=CHCH$_2$(CH$_2$)$_5$CH$_2$CH=C<), 3.00 (m, 3 H, H-4$_a$, H-4'$_{a,b}$), 3.42 (dm, J=16.9 Hz, 2 H, H-4$_a$), 3.90 (AB q, J=11.9 Hz, 2 H, CH$_2$OH), 4.38 (m, 2 H-5'$_{a,b}$), 5.32 (m, 2 H, CH$_3$(CH$_2$)$_6$CH$_2$CH=CH(CH$_2$)$_7$CH=C<), 6.18 (m, 1 H, C$_{17}$H$_{33}$CH=C<), 6.47 (t, J=2.4 Hz, 1 H, >C=CH—C); $^{13}$C NMR (CDCl$_3$) δ 14.10, 22.67, 27.20, 27.69, 29.03, 29.20, 29.23, 29.30, 29.50, 29.56, 29.69, 29.71, 31.89, 37.68, 65.71, 66.71, 85.63, 124.47, 126.49, 129.79, 129.95, 143.20, 145.05, 168.31, 168.67; FAB MS m/z (relative intensity) 461 (MH$^+$, 22). Anal. Calcd for C$_{28}$H$_{44}$O$_5$: C, 73.00; H, 9.63. Found: C, 72.75; H, 9.67.

Compound 3.13: solid gum; $[\alpha]^{22}_D$ −16.190° (c 0.42, CHCl$_3$); IR (neat) 3407 (OH), 1746 and 1722 (C=O), 1678 cm$^{-1}$ (C=C); $^1$H NMR (CDCl$_3$) δ 0.86 (distorted t, 3 H, CH$_3$(CH$_2$)$_7$CH=CH(CH$_2$)$_7$CH=C<), 1.10–1.50 (m, 22 H, CH$_3$(CH$_2$)$_6$CH$_2$CH=CHCH$_2$(CH$_2$)$_5$CH$_2$CH=C<), 2.00 (m, 4 H, CH$_3$(CH$_2$)$_6$CH$_2$CH=CHCH$_2$(CH$_2$)$_5$CH$_2$CH=C<), 2.18 (m, 2 H, CH$_3$(CH$_2$)$_6$CH$_2$CH=CHCH$_2$(CH$_2$)$_5$CH$_2$CH=C<), 2.88 (dm, J=17.9 Hz, 1 H, H-4$_a$),3.00 (m, 2 H, H-4'$_{a,b}$), 3.40 (dm, J=17.9 Hz, 1 H, H-4$_b$), 3.92 (AB q, J=12.0 Hz, 2 H, CH$_2$OH), 4.38 (m, 2 H, H-5'$_{a,b}$), 5.32 (m, 2 H, CH$_3$(CH$_2$)$_6$CH$_2$CH=CH(CH$_2$)$_7$CH=C<), 6.49 (t, J=2.4 Hz, 1 H, >C=CH—C), 6.69 (m, 1 H, C$_{17}$H$_{33}$CH=C<); $^{13}$C NMR (CDCl$_3$) δ 14.10, 22.67, 27.16, 27.21, 28.09, 29.16, 29.30, 29.51, 29.69, 29.74, 30.21, 31.89, 32.59, 34.64, 65.74, 66.75, 86.27, 126.45, 126.54, 129.71, 130.01, 141.66, 143.14, 168.33, 169.90; FAB MS m/z (relative intensity) 461 (MH$^+$, 26). Anal. Calcd for C$_{28}$H$_{44}$O$_5$: C, 73.00; H, 9.63. Found: C, 72.90; H, 9.57.

Example 14

This example compares the affinities of the chiral compounds of Examples 6 and 7 with the affinities of the compounds of Examples 9–13 for PK-C.

The affinities of the compounds of Examples 9–13 were determined as described in Example 5 and are presented in Tables III–V.

TABLE III

Apparent K$_i$ for Racemic and Chiral Ligands as Inhibitors of PDBU Binding to PK-C.

| Racemic Compound | K$_i$ (nM) | Chiral Compound | K$_i$ (nM) | Chiral Compound | K$_i$ (nM) |
|---|---|---|---|---|---|
| 3.2, R=CH$_3$(CH$_2$)$_{13}$ | 489.0 ± 87 | 3.3, R=CH$_3$(CH$_2$)$_{13}$ | 259.5 ± 40.80 | 3.5, R=CH$_3$(CH$_2$)$_{13}$ | 108.7 ± 6.68 |

TABLE III-continued

Apparent K$_i$ for Racemic and Chiral Ligands as Inhibitors of PDBU Binding to PK-C.

| Racemic Compound | K$_i$ (nM) | Chiral Compound | K$_i$ (nM) | Chiral Compound | K$_i$ (nM) |
|---|---|---|---|---|---|
| | | 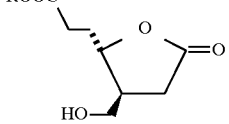<br>3.4, R=CH$_3$(CH$_2$)$_{13}$ | 27,300.0 ± 2,500 | 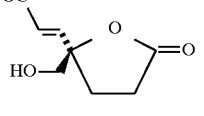<br>3.6, R=CH$_3$(CH$_2$)$_{13}$ | 27,200.0 ± 7,700 |

TABLE IV

Apparent K$_i$ for Chiral Ligands Having an α-alkylidene Chain as Inhibitors of PDBU Binding to PK-C [R=(Z)—CH$_3$(CH$_2$)$_7$CH=CH(CH$_2$)$_7$].

| Chiral Compound | K$_i$ (nM) |
|---|---|
| 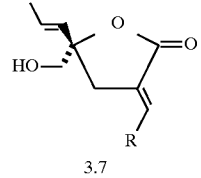<br>3.7 | 20.1 ± 2.90 |
| 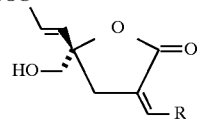<br>3.7 | 11.3 ± 0.72 |
| 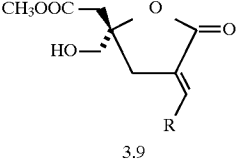<br>3.9 | 12.6 ± 1.26 |
| 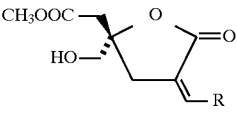<br>3.10 | 11.8 ± 0.40 |

TABLE V

Apparent K$_i$ for Chiral Ligands with Two γ-Lactone Pharmacophores as Inhibitors of PDBU Binding to PK-C [R=(Z)—CH$_3$(CH$_2$)$_7$CH=CH(CH$_2$)$_7$].

| Chiral Compound | K$_i$ (nM) |
|---|---|
| 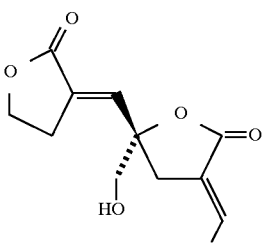<br>3.11 | 25.7 ± 4.76 |
| 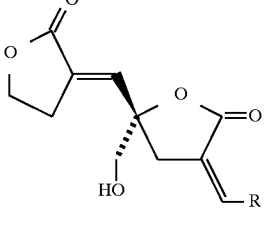<br>3.12 | 19.2 ± 1.86 |
| 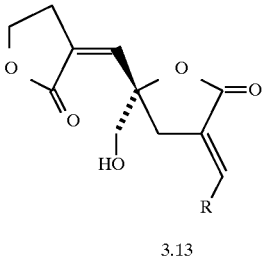<br>3.13 | 2,020.0 ± 340.00 |
| 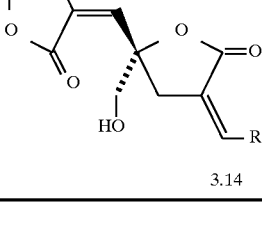<br>3.14 | 746.0 ± 25.00 |

The affinity of ligands 3.2 (racemic) and 3.3–3.14 (chiral) for PK-C α was expressed in terms of their ability to displace bound [$^3$H-20]-phorbol-12,13-dibutyrate (PDBU), and was measured in the same manner as described in Example 5. Analysis of the data indicate that the "reverse ester" racemic ligand 3.2 ($K_i$=489 nM, Table III) suffered a 3.5-fold loss in binding affinity relative to racemic 2.1 ($K_i$=138 nM). Relative to the chiral compounds (Table III), the predicted active ligands 3.3 ($K_i$=259 nM) and 3.5 ($K_i$=108 nM) showed a direct structural correspondence to the active (R)-enantiomer of 1 ($K_i$=96 nM) that was built on a 5-(acyloxymethyl)-5-(hydroxymethyl)tetrahydro-2-furanone template. The corresponding optical antipodes 3.4 and 3.6 were, respectively, 100 to 200-fold less potent. A direct comparison between 3.5 ($K_i$=108 nM) and the active enantiomer of 1 ($K_i$=96 nM) indicated that the more rigid α,β-unsaturated ester branch in 3.5 was able to recover the loss in binding affinity that resulted from the reversal of the ester function. The double bond in 3.5 appears capable of steering the ester pharmacophore in the same direction as in the "bound" gauche rotamer of 5-(acyloxymethyl)-5-(hydroxymethyl)tetrahydro-2-furanones. The same phenomenon was observed for the more potent α-alkylidene analogues 3.7 ($K_i$=20 nM) and 3.8 ($K_i$=11 nM), which proved to be equivalent to the corresponding α-alkylidenes 3.9 and 3.10 built on a chiral 5-(acyloxymethyl)-5-(hydroxymethyl) tetrahydro-2-furanone template (Table IV). Compounds 3.7 and 3.8 are to date the most potent and stable DAG mimics. Compounds 3.11 ($K_i$=25 nM) and 3.12 (19 nM) were, respectively, 30 to 100-fold more potent than their isomers 3.13 and 3.14 (Table IV).

The biological activity of compound 3.8 was evaluated further. The binding of compond 3.8 to PK-C α led to activation of the enzyme; it stimulated phosphorylation of the a-pseudosubstrate peptide (a standard substrate for assay of the enzyme) with an $ED_{50}$ of 163.3±16.7 nM. This finding demostrated that 3.8 would function in the intact cell or organism as either an agonist or as a partial antagonist. In intact cells, compound 3.8 caused inhibition of binding of epidermal growth factor with an $ED_{50}$ of 1 μM, which is a typical response to PK-C activation. In contrast to the phorbol esters, compound 3.8 did not induce acute edema (10–100 μg, 6 h) or hyperplasia (10–100 μg, 72 h) in CD-1 mouse skin. Finally, the ability of compound 3.8 to down-regulate PK-C α and PK-C δ in primary mouse keratinocytes after 24 hours was examined. The compound down-regulated the levels of PK-C α and δ with an $ED_{50}$ of 1 μM, whereas it did not down-regulate the levels of PK-Cεor PK-Cη. No loss in activity was observed, even after 24 h. The biological data indicated that the double bond in compound 3.8 was able to compensate entirely for the loss of the gauche effect in the "reverse esters" and hence the binding affinities for both 3.8 and 3.10 were identical ($K_i$=11 nM).

In view of the above, the compounds of the present invention are DAG analogues with pharmacologically useful activity levels. The compounds offer the advantages of structural stability, ease of synthesis, and resistance to degradation in vivo.

All of the references cited herein, including patents, patent applications, and publications, are hereby incorporated in their entireties by reference.

While this invention has been described with reference to preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of:

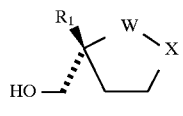

Formula A or

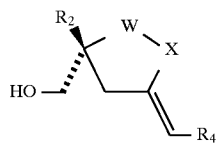

Formula B wherein W is oxygen, X is C(O), $R_1$ is CH=CHSO$_2$R$_3$, CH=CHSO$_2$NHR$_3$, CH=CHC(O)OR$_3$, CH=CHC(O)NHR$_3$ or CH=CHC(O)N(OH)R$_3$, $R_2$ is CH=CHSO$_2$R$_3$, CH=CHSO$_2$NHR$_3$, CH=CHC(O)OR$_3$, CH=CHC(O)ONHR$_3$, CH=CHC(O)N(OH)R$_3$, CH$_2$CH(OH)C(O)OR$_3$, CH$_2$CH(OH)SO$_2$R$_3$, CH$_2$CH(OH)SO$_2$NHR$_3$ or CH$_2$CH(OH)C(O)NHR$_3$, and $R_3$ and $R_4$ are the same or different and are selected from the group consisting of a $C_{1-18}$ alkyl, a $C_{2-18}$ alkenyl, a $C_{6-14}$ aryl, a $C_{1-18}$ alkyl-$C_{6-14}$ aryl, and a $C_{6-14}$ aryl-$C_{1-18}$ alkyl.

2. The compound of claim 1, wherein $R_3$ is a $C_{1-4}$ alkyl and $R_4$ is a $C_{2-18}$ alkenyl.

3. The compound of claim 2, wherein $R_3$ is methyl.

4. The compound of claim 3, wherein said compound is (S)-5-hydroxymethyl-5-[2-(methoxycarbonyl)ethenyl]-3-{(E)-[(Z)-9-octadecenoylidene]}tetrahydro-2-furanone.

5. The compound of claim 3, wherein said compound is (S)-5-hydroxymethyl-5-[2-(methoxycarbonyl)ethenyl]-3-{(Z)-[(Z)-9-octadecenoylidene]}tetrahydro-2-furanone.

6. A pharmaceutical composition comprising a compound of claim 1 and a pharmaceutically acceptable carrier.

7. A pharmaceutical composition comprising a compound of claim 2 and a pharmaceutically acceptable carrier.

8. A pharmaceutical composition comprising a compound of claim 3 and a pharmaceutically acceptable carrier.

9. A pharmaceutical composition comprising a compound of claim 4 and a pharmaceutically acceptable carrier.

10. A pharmaceutical composition comprising a compound of claim 5 and a pharmaceutically acceptable carrier.

11. A method of inhibiting a protein kinase C-mediated biological response in a mammal in need of such inhibition, which method comprises administering to said mammal a protein kinase C-antagonistic compound of claim 1 in an amount sufficient to inhibit said protein kinase C-mediated biological response.

12. A method of promoting a protein kinase C-mediated biological response in a mammal in need of such promotion, which method comprises administering to said mammal a protein kinase C-agonistic compound of claim 1 in an amount sufficient to promote said protein kinase C-mediated biological response.

* * * * *